United States Patent [19]
Claremon et al.

[11] Patent Number: 5,821,241
[45] Date of Patent: Oct. 13, 1998

[54] FIBRINOGEN RECEPTOR ANTAGONISTS

[75] Inventors: David Alan Claremon, Maple Glen; John J. Baldwin, Gwynedd Valley; Nigel Liverton, Harleysville; Ben Askew, Lansdale, all of Pa.

[73] Assignee: Merck & Co., Inc., Rahway, N.J.

[21] Appl. No.: 495,560

[22] PCT Filed: Feb. 22, 1994

[86] PCT No.: PCT/US94/01881

§ 371 Date: Aug. 1, 1995

§ 102(e) Date: Aug. 1, 1995

[87] PCT Pub. No.: WO94/18981

PCT Pub. Date: Sep. 1, 1994

[51] Int. Cl.⁶ .......... H61K 31/495; H61K 31/55; C07D 471/04; C07D 487/04
[52] U.S. Cl. .......... 514/221; 514/80; 514/81; 514/214; 514/249; 514/300; 514/303; 540/487; 540/500; 540/502; 544/337; 544/349; 544/350; 546/23; 546/120; 546/121
[58] Field of Search .......... 540/502, 500, 540/487; 544/350, 349, 337; 546/120, 121, 23; 514/214, 249, 300, 303, 80, 81, 221

[56] References Cited

U.S. PATENT DOCUMENTS

| | | | |
|---|---|---|---|
| 3,322,631 | 5/1967 | Sprague et al. | 167/65 |
| 4,010,274 | 3/1977 | Giraldi et al. | 424/274 |
| 4,122,255 | 10/1978 | Krapcho | 542/421 |
| 4,243,807 | 1/1981 | Friebe et al. | 546/232 |
| 4,313,947 | 2/1982 | Nakagawa et al. | 424/248.54 |
| 4,622,331 | 11/1986 | Jozic | 514/331 |
| 5,030,654 | 7/1991 | Barnish et al. | 514/510 |
| 5,095,018 | 3/1992 | Kelley | 514/249 |
| 5,166,154 | 11/1992 | Skiles et al. | 314/249 |
| 5,227,490 | 7/1993 | Hartman et al. | 514/317 |
| 5,260,316 | 11/1993 | Van Duzer et al. | 514/309 |
| 5,264,420 | 11/1993 | Duggan et al. | 514/19 |
| 5,272,158 | 12/1993 | Hartman et al. | 514/323 |
| 5,278,161 | 1/1994 | Branca et al. | 514/244 |
| 5,281,585 | 1/1994 | Duggan et al. | 514/79 |
| 5,292,756 | 3/1994 | Duggan et al. | 514/331 |
| 5,294,616 | 3/1994 | Duggan et al. | 514/255 |
| 5,321,034 | 6/1994 | Duggan et al. | 514/323 |

FOREIGN PATENT DOCUMENTS

| | | |
|---|---|---|
| 0 229 391 A1 | 7/1987 | European Pat. Off. . |
| 0 332 528 A1 | 9/1989 | European Pat. Off. . |
| 0 352 249 A1 | 1/1990 | European Pat. Off. . |
| 0 372 486 A2 | 6/1990 | European Pat. Off. . |
| 0 381 033 A1 | 8/1990 | European Pat. Off. . |
| 0 384 362 A2 | 8/1990 | European Pat. Off. . |
| 0 405 537 A1 | 1/1991 | European Pat. Off. . |
| 0 540 334 A1 | 5/1993 | European Pat. Off. . |
| 2 612 185 A1 | 9/1988 | France . |

OTHER PUBLICATIONS

Sugimoto et al., "7-(Ethoxycarbonyl)-6,8-dimethyl-2-phenyl-1(2H)-phthalazinone Derivatives: Synthesis and Inhibitory Effects on Platelet Aggregation", J. Med. Chem., vol. 27, pp. 1300–1305 (1984).

*Primary Examiner*—Richard L. Raymond
*Attorney, Agent, or Firm*—Richard S. Parr; Melvin Winokur

[57] ABSTRACT

Compounds of the invention have the formula

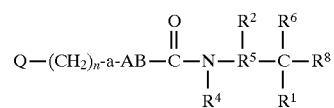

or

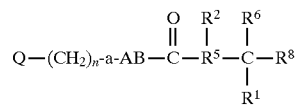

for example

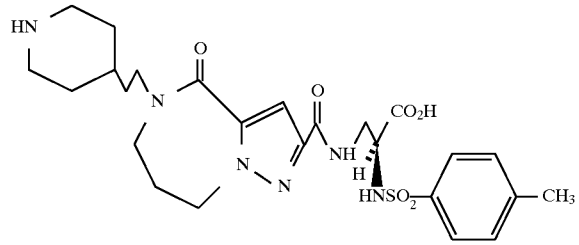

The compounds have fibrinogen receptor antagonist activity.

16 Claims, No Drawings

FIBRINOGEN RECEPTOR ANTAGONISTS

This application is a 371 of PCT/U.S. 94/01881, filed Feb. 22, 1994.

BACKGROUND OF THE INVENTION

The invention relates generally to modulating cell adhesion and to inhibiting the binding of fibrinogen and other proteins to blood platelets, and inhibiting the aggregation of blood platelets specifically to the IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothelial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science*, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A.*, 84, 6471–6475, (1987), describes an Arg-Gly-Asp directed adhesion receptor expressed by human endothelial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the stereochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In *Proc. Nat'l Acad. Sci. U.S.A.*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cellbinding domain of fibronectin have cell-attachment activity. For example, see U.S. Pat. Nos. 4,517,686, 4,661,111 and U.S. Pat. No. 4,578,079.

Ruggeri et al., *Proc. Nat'l Acad. Sci. U.S.A.*, 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.* 23, 1767–1774 (1984); Ginsberg et al., *J. Biol. Chem.* 260(7), 3931–3936 (1985); and Haverstick et al., *Blood* 66(4), 946–952 (1985). Other inhibitors are disclosed in Eur. Pat. Nos. 275,748 and 298,820.

A number of low molecular weight polypeptide factors have been isolated from snake venom. These factors apparently have high affinity for the gpIIb/IIIa complex. For example, Huang et al., *J. Biol Chem.*, 262, 16157–16163 (1987); Huang et al., *Biochemistry* 28, 661–666 (1989) describe the primary structure of the venom trigramin which is a 72 amino acid polypeptide that contains the RGD subunit. Echistatin is another venom which has high affinity for the gpIIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'l Acad. Sci. USA*, 87, 2471–2475 (1989). However, these snake venom factors also have high affinity for other members of the adhesive protein receptor family including the vitronectin and fibronectin receptors so are not selective for the gpIIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No. 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gpIIb/IIIa receptor. U.S. Pat. No. 5,037,808 discloses guanidino peptide mimetic compounds that retain an Asp residue which inhibit platelet aggregation. WO9014103 describes the use of antibody-poly-peptide conjugates wherein said polypeptides contain the Arg-Gly-Asp (RGD) sequence.

WO91114581 discloses the use of large cyclic peptides containing RGD flanked by proline residues which are platelet aggregation inhibitors. WO9101331 discloses small cyclic platelet aggregation inhibitors which are synthetic cyclic pentapeptides containing the tripeptide sequence Arg-Gly-Asp and a thioether linkage in the cycle. U.S. Pat. No. 5,051,405, also discloses the use of peptides and pseudopeptides such as N-amidino-piperidine-3-carboxylglycyl-L-aspartyl-L-valine that inhibit platelet aggregation and thrombus formation in mammalian blood. Eur. Pat. 445 796 discloses linear compounds which can include internal piperazinyl or piperidinyl derivatives. Eur. Pat. 437 367, discloses linear polypeptide fibrinogen receptor antagonists. U.S. Pat. No. 5,256,812 discloses compounds of the $R^1$-A-(W)$_a$-X-(CH$_2$)$_b$-(Y)$_c$-B-Z—COOR wherein $R^1$ is a guanidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

Compounds of the invention have the formula

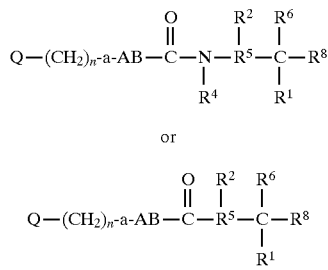

or

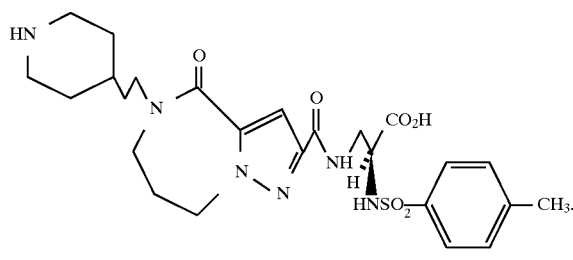

for example

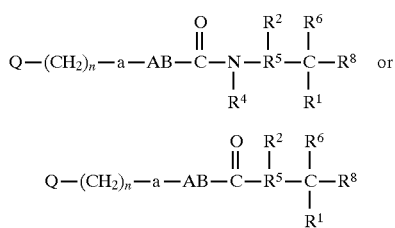

The compounds have fibrinogen receptor antagonist activity.

DETAILED DESCRIPTION OF THE INVENTION

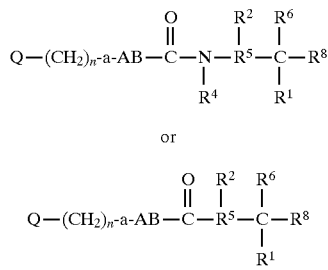

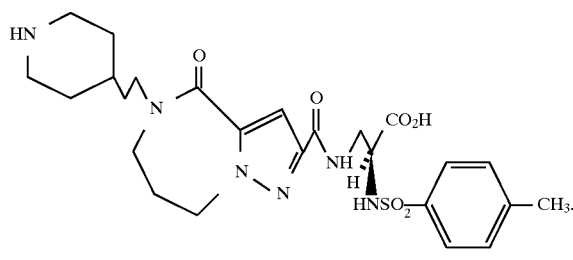

wherein
Q is

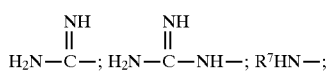

or
Q is a 4–9 membered mono- or bi-cyclic ring system containing 1, 2 or 3 heteroatoms chosen from N, O or S and either unsubstituted or substituted with $R^8$;

AB is a fused ring system sharing adjacent carbon and nitrogen atoms, wherein
  A is a 5, 6 or 7 membered saturated or unsaturated ring containing 1, 2 or 3 heteroatoms selected from O, S or N;
  B is a 5, 6 or 7 membered saturated or unsaturated ring containing 1, 2 or 3 heteroatoms selected from O, S or N;

$R^1$ is H, $C_{1-4}$ alkyl, $N(R^8)_2$, $-N(R^8)SO_2R^7$, $NR^8CO_2R^7$, $NR^8C(O)R^7$, $NR^8C(O)N(R^7)R^8$, $N(R^8)SO_2N(R^7)R^8$, $N(R^8)SO_2N(R^8)C(O)OR^7$, $C(O)N(R^7)_2$, or a cyclic group with $R^6$ as defined below;

$R^2$ is H, $C_{1-4}$ alkyl, $C_{1-4}$ branched alkyl, $C_{1-4}$ alkyl aryl, or aryl;

$R^4$ is H, $C_{1-4}$ alkyl, $C_{1-4}$ branched alkyl, cyclic $C_{1-4}$ alkyl or $C_{1-4}$ alkenyl;

$R^5$ is CH, $-CH(CH_2)_n$, a bond, or when $R^5$ is adjacent $N(R^4)$,

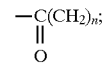

$R^6$ is COOH, $CH_2OH$, $C(O)N(R^7)_2$, $CO_2R^9$, tetrazole, acylsulfonamide, or

or a cyclic group with $R^1$ as defined below;
wherein the cyclic group of $R^1$ with $R^6$ is

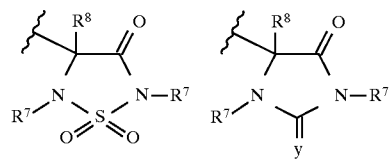

wherein y=O or S;

$R^7$ is H, branched or straight chain $C_{1-4}$ substituted or unsubstituted alkyl, branched or straight chain lower alkenyl, $C_{1-4}$ alkylaryl, substituted aryl, or 5 or 6 membered heteroaryl containing 1, 2, or 3N, S, or O heteroatoms
  wherein substituted alkyl is hydroxy substituted or $C_{1-4}$ alkoxy substituted alkyl, and wherein substituted aryl is substituted by one, two or three of the following groups: halogen, $C_{1-4}$ alkoxy, hydroxy, or $C_{1-4}$ alkyl;

$R^8$ is H, branched or straight chain $C_{1-4}$ alkyl;

$R^9$ is H, $C_{1-4}$ alkyl or aryl;

n is 0–7;

n' is 0–3; and a is

or a bond, and pharmaceutically acceptable salts.

In one embodiment, the compounds have the formula $$Q-(CH_2)_n-a-AB-\overset{O}{\underset{\|}{C}}-\overset{R^2}{\underset{R^4}{N}}-\overset{R^6}{\underset{R^1}{C}}-R^8 \text{ or}$$

$$Q-(CH_2)_n-a-AB-\overset{O}{\underset{\|}{C}}-\overset{R^2}{\underset{|}{R^5}}-\overset{R^6}{\underset{R^1}{C}}-R^8$$

wherein

Q is

[structures shown]

$n = 0–7$;

$n' = 0–3$;

$R^4 = H$, $C_{1-4}$ alkyl, $C_{1-4}$ branched alkyl, cyclic $C_{1-4}$ alkyl or $C_{1-4}$ alkenyl;

$R^5 = CH$, $-CH(CH_2)_n$, or a bond;

$R^2$ is H, $C_{1-4}$ alkyl, $C_{1-4}$ branched alkyl, $C_{1-4}$ alkyl aryl, or aryl;

$R^1 = H$, $C_{1-4}$ alkyl, $N(R^8)_2$, $-N(R^8)SO_2R^7$, $NR^8CO_2R^7$, $NR^8C(O)R^7$, $NR^8C(O)N(R^7)R_8$, $N(R^8)SO_2N(R^7)R^8$, $N(R^8)SO_2N(R^8)C(O)OR^7$, $C(O)N(R^7)_2$, or a cyclic group with $R^6$;

$R^6 = COOH$, $CH_2OH$, $C(O)N(R^7)_2$, $CO_2R^9$, tetrazole, acylsulfonamide, or $$\overset{P(OH)_2,}{\underset{O}{\|}}$$

or a cyclic group with $R^1$;

wherein the cyclic group of $R^1$ with $R^6$ is

[structures shown]

wherein $y = O$ or $S$;

$R^7 = H$, branched or straight chain $C_{1-4}$ substituted or unsubstituted alkyl, branched or straight chain lower alkenyl, $C_{1-4}$ alkylaryl, substituted aryl, or 5 or 6 membered heteroaryl containing 1, 2, or 3 N, S, or O heteroatoms wherein substituted alkyl is hydroxy substituted or $C_{1-4}$ alkoxy substituted alkyl, and wherein substituted aryl is substituted by one two or three of the following groups: halogen, $C_{1-4}$ alkoxy, hydroxy, or $C_{1-4}$ alkyl;

$R^8 = H$, branched or straight chain $C_{1-4}$ alkyl;

$R^9 = H$, $C_{1-4}$ alkyl or aryl;

a =

$$-\overset{}{\underset{R^7}{N}}-\overset{O}{\underset{}{C}}-$$

or a bond;

A = a 5, 6 or 7 membered saturated, partially saturated, or unsaturated ring containing 1, 2 or 3 heteroatoms selected from O, S or N;

B = a 5, 6 or 7 membered saturated, partially saturated, or unsaturated ring containing 1, 2 or 3 heteroatoms selected from O, S or N;

wherein A and B form a fused ring system sharing adjacent carbon and nitrogen atoms.

In the compounds of the present invention, the components having asymmetric centers occur as racemates, racemic mixtures, and as individual enantiomers and/or diastereomers. All isomeric forms are included in the present invention.

In one class of this embodiment, the compounds have the formula,

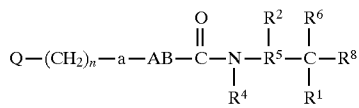

AB is selected from the group of

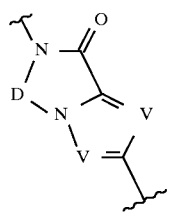

wherein V is N or $CR^7$, and D is $CH_2$, $CH_2$—$CH_2$, $CH_2C(R^7)_2CH_2$, or

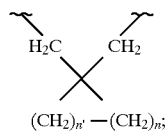

wherein X=N or $CR^3$,
wherein $R^3$=CN, $C(O)N(R^7)R^8$,

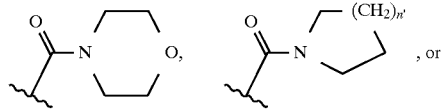

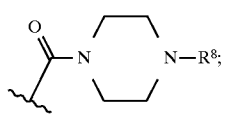 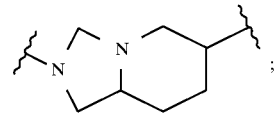

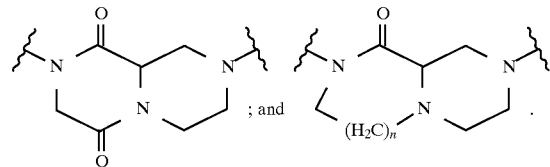

In a subclass of this class of this embodiment compounds are those having the formula

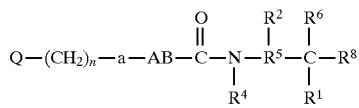

where AB is

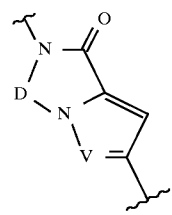

wherein V is N or CH, and D is $CH_2$—$CH_2$ or $CH_2C(R^4)_2CH_2$.

In another class of this embodiment the compounds have the formula

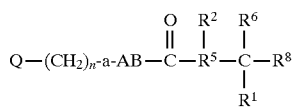

AB is selected from the group of

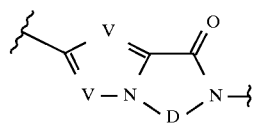

wherein V is N or $CR^7$ and D is $CH_2$, $CH_2$—$CH_2$, $CH_2C(R^7)_2CH_2$, or

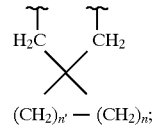

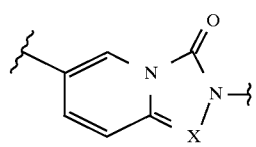

wherein X=N or $CR^3$,
wherein $R^3$=CN, $C(O)N(R^7)R^8$,

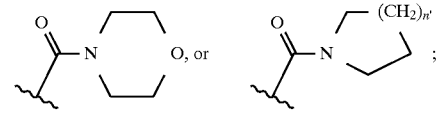

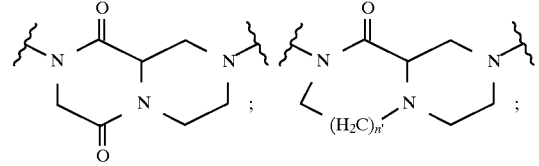

and

-continued

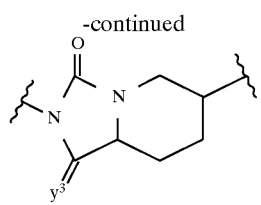

wherein $y^3$ is O or $H_2$.

In a subclass of this class of this embodiment, the compounds have the formula $$Q-(CH_2)_n\text{-a-AB}-\overset{O}{\underset{\|}{C}}-\overset{R^2}{\underset{|}{R^5}}-\overset{R^6}{\underset{|}{C}}-R^8,$$
$$\underset{R^1}{}$$

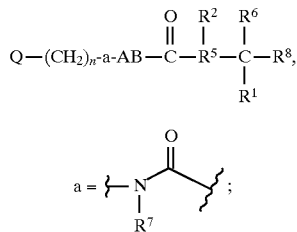

and AB is selected from

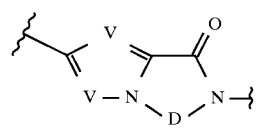

wherein V is N or $CR^7$, and D is $CH_2$, $CH_2$—$CH_2$, $CH_2C(R^7)_2CH_2$, or

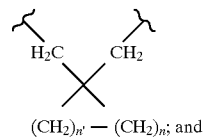

and
wherein X=N or $CR^3$, wherein $R^3$=CN, $C(O)N(R^7)R^8$,

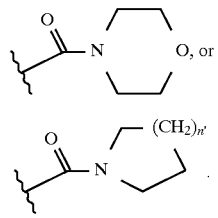

In another subclass of this class of this embodiment, the compounds have the formula $$Q-(CH_2)_n\text{-a-AB}-\overset{O}{\underset{\|}{C}}-\overset{R^2}{\underset{|}{R^5}}-\overset{R^6}{\underset{|}{C}}-R^8,$$
$$\underset{R^1}{}$$

a=a bond; and AB is selected from

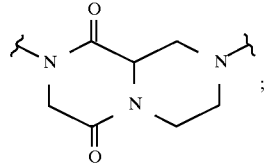

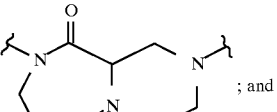
; and

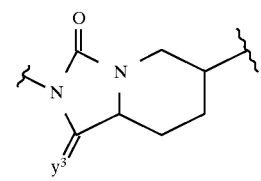

wherein $y^3$ is O or $H_2$.

Specific examples of compounds of the invention are those selected from the following group of compounds and their pharmaceutically acceptable salts:

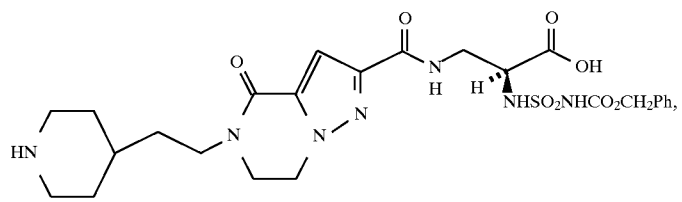

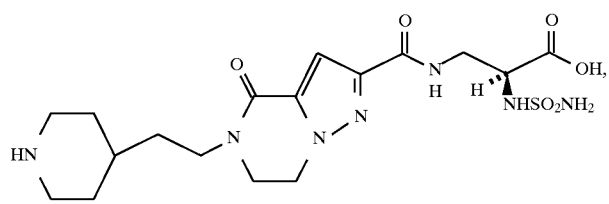

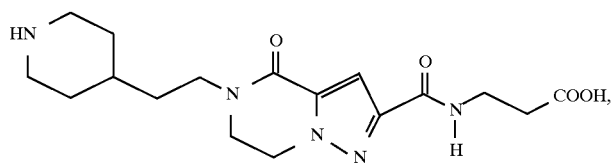
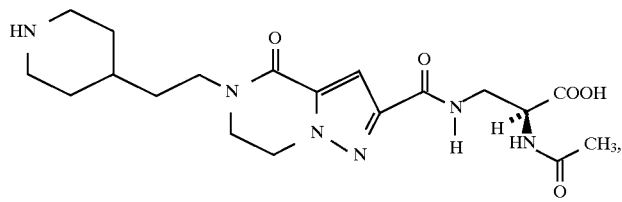
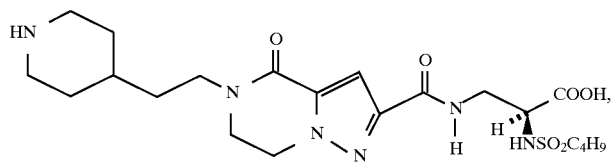
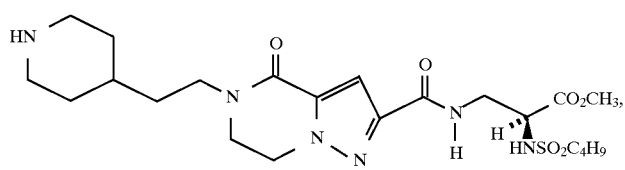
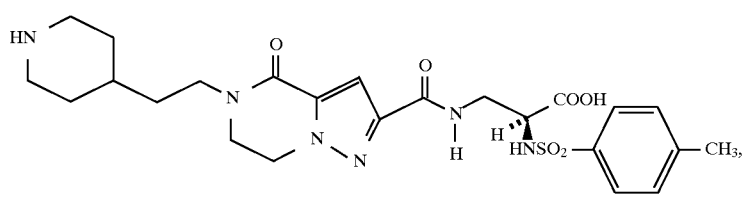
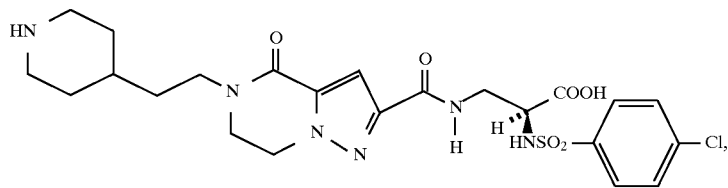
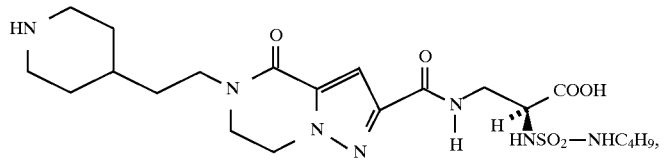
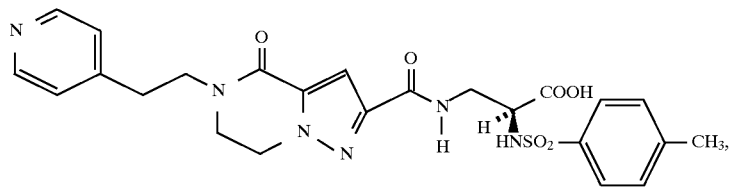

-continued
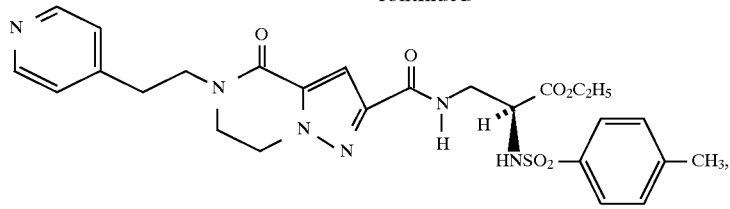
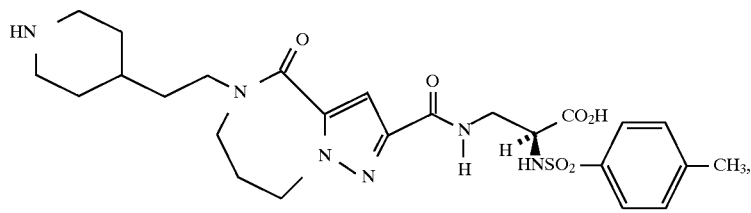
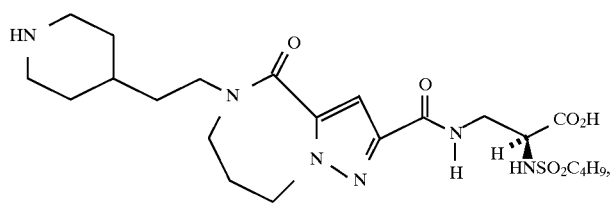
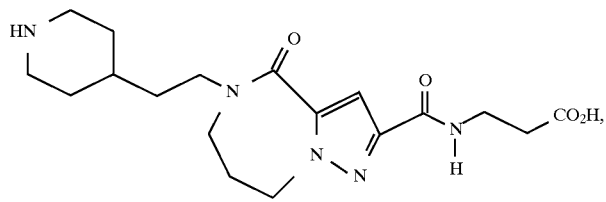
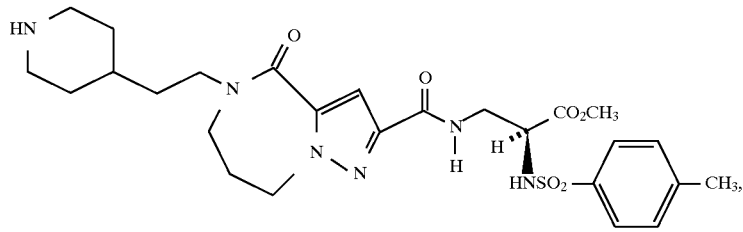
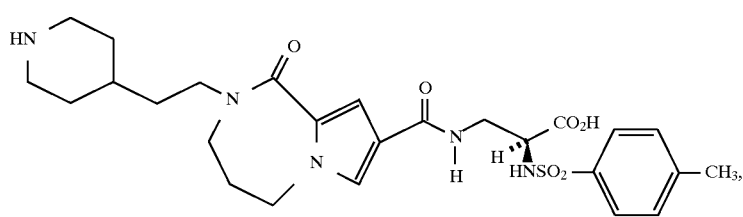
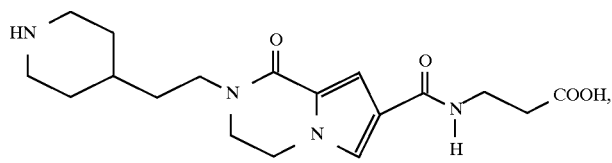
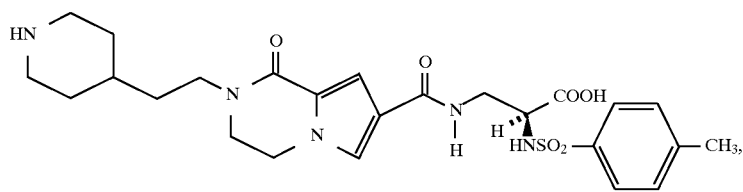

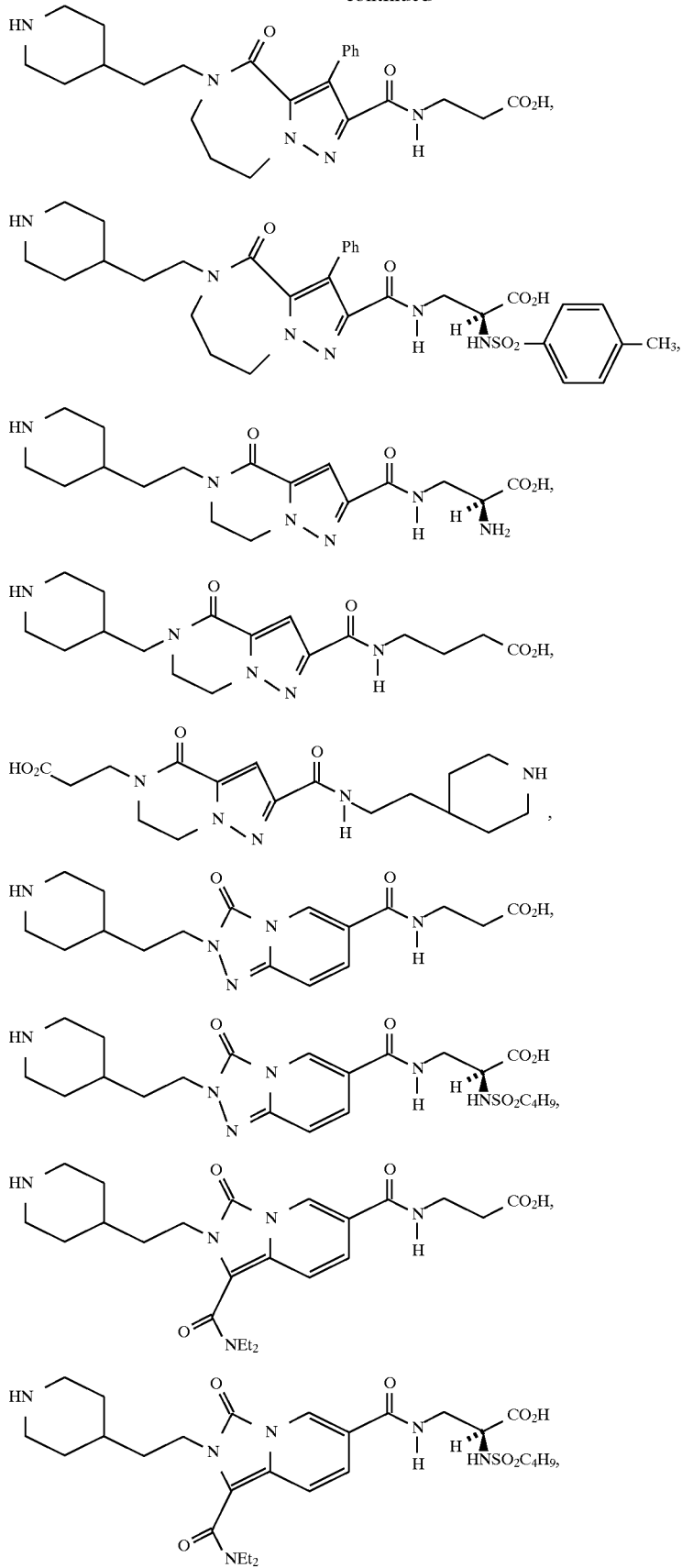

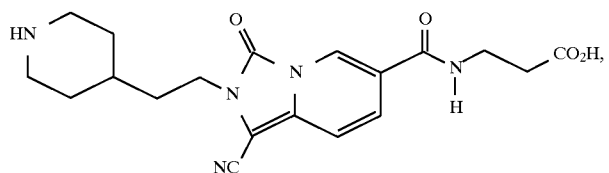
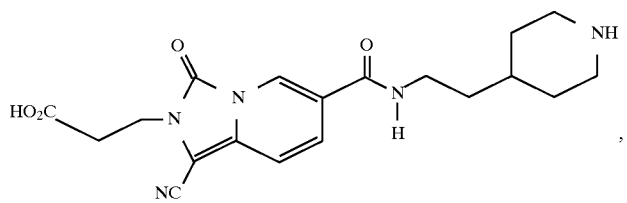
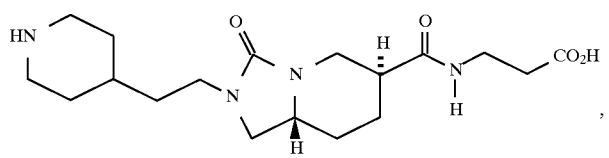
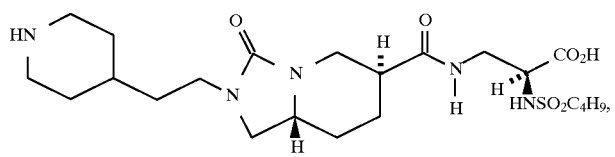
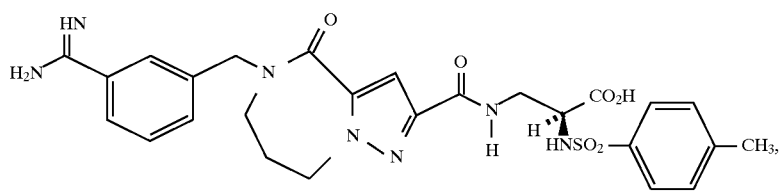
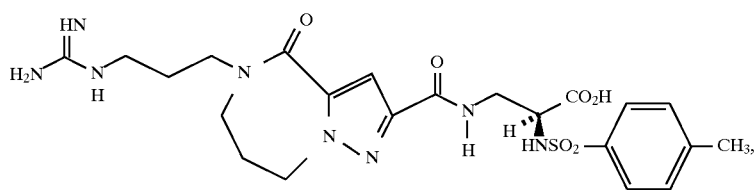
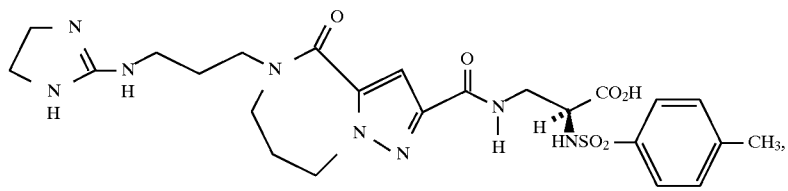
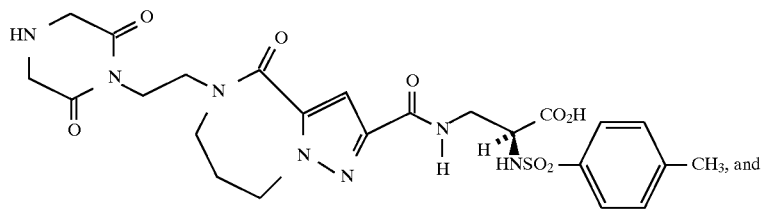

-continued

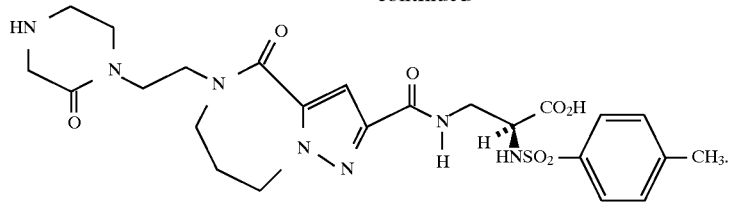

Additional examples of compounds of the invention are

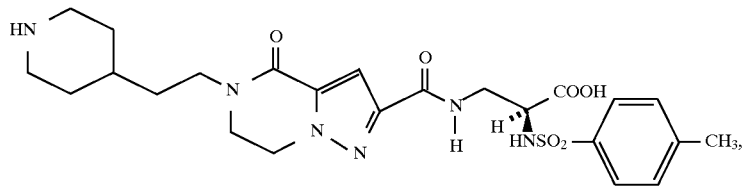

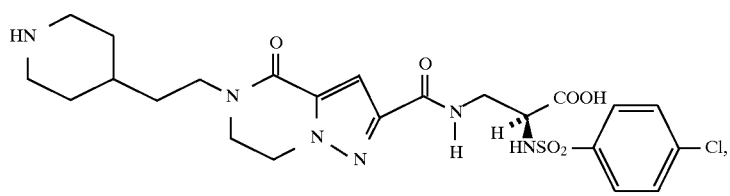

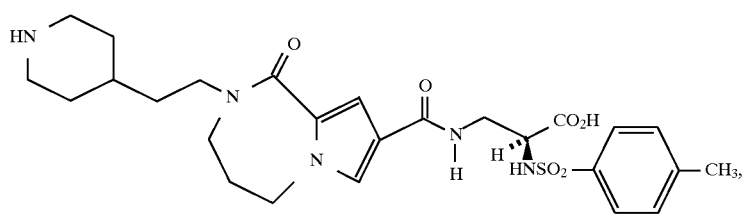

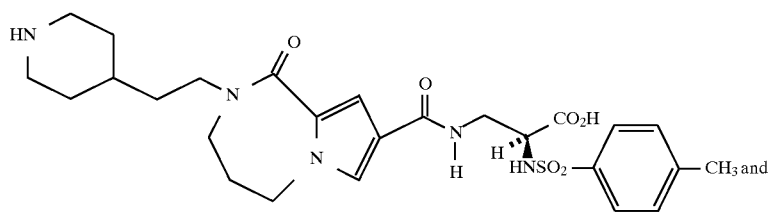

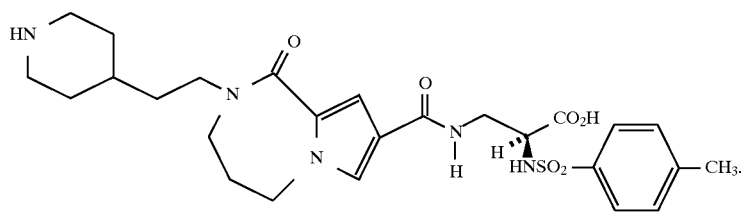

The term "pharmaceutically acceptable salts" shall mean non-toxic salts of the compounds of this invention which are generally prepared by reacting the free base with a suitable organic or inorganic acid. Representative salts include the following salts: Acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include streptokinase and tissue plasminogen activator. The term "platelet anti-aggregation agent" includes, for example, aspirin, ticlopidine, and dipyridamole.

The term "alkyl" means straight or branched alkane, alkene or alkyne.

The term "aryl" means a 5–10 membered unsaturated mono- or bicyclic ring group.

The term "heteroaryl" means aryl containing 1, 2, 3 or 4 heteroatoms.

The term "heteroatom" means N, O, or S.

The term "cyclic," unless otherwise more specifically defined, means mono- or bicyclic saturated ring groups having 5–10 members.

The term "heterocyclic" means cyclic containing 1, 2, 3 or 4 heteroatoms.

In the compounds of the invention, heteroaryl groups and heterocyclic groups contain no more than 2 O atoms or 2 S atoms.

The term "alkoxy" includes an alkyl portion where alkyl is as defined above.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit.

The term "halogen" includes fluorine, chlorine, iodine and bromine.

The term "oxy" means an oxygen (O) atom. The term "oxo" means (=O). The term "thio" means a sulfur (S) atom. Under standard nomenclature used throughout this disclosure, the terminal portion of the designated side chain is described first followed by the adjacent functionality toward the point of attachment. For example, a $C_{1-5}$ alkyl substituted with $C_{1-6}$ alkylcarbonylamino is equivalent to

In the schemes and examples below, various reagent symbols have the following meanings:
BOC(Boc): t-butyloxycarbonyl.
Pd-C: palladium on activated carbon catalyst.
DMF: dimethylformamide.
DMSO: dimethylsulfoxide.
CBZ: carbobenzyloxy.
$CH_2Cl_2$: methylene chloride.
$CHCl_3$: chloroform.
EtOH: ethanol.
MeOH: methanol.
EtOAc: ethyl acetate.
HOAc: acetic acid.
BOP: benzotriazol-1-yloxytris(dimethylamino) phosphonium, hexafluorophosphate.
EDC: 1-(3-Dimethylaminopropyl)-3-ethylcarbodiimide
Oxone: potassium peroxymonosulfate
LDA: lithium diisopropylamide
DMA: N,N-Dimethylaniline
HOBT: Hydroxybenzotriazole
Therapeutic Treatment Compounds of the invention may be used for inhibiting integrin protein-complex function relating to cell attachment activity. They may be administered to patients where inhibition of human or mammalian platelet aggregation or adhesion is desired.

Certain compounds of the invention are eliminated from circulation rapidly and are particularly useful in inhibiting platelet aggregation. Thus, these compounds may find utility in surgery on peripheral arteries (arterial grafts, carotid endaterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

The compounds of the present invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, sublingual, intranasal or intramuscular form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary and other arteries and after coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.05–100 mg/kg/day and most preferably 0.1–20 mg/kg/day. Intravenously, the most preferred doses will range from about 1 to about 10 $\mu$g/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather that intermittent throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinlypyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anticoagulants, including anti-platelet agents such as heparin, aspirin, warfarin, dipyridamole and other compounds and agents known to inhibit blood clot formation, and thrombolytic agents such as plasminogen activators or streptokinase, to achieve beneficial effects in the treatment of various vascular pathologies.

The novel compounds of the present invention were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

In addition to the following preparative procedures, several examples of in vitro bioactivity of compounds within the scope of the present invention are indicated. To illustrate, one test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$(1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

In the following examples, all temperatures are in degrees Celsius, unless otherwise indicated.

SCHEME A
Preparation of sulfonamide intermediate compounds

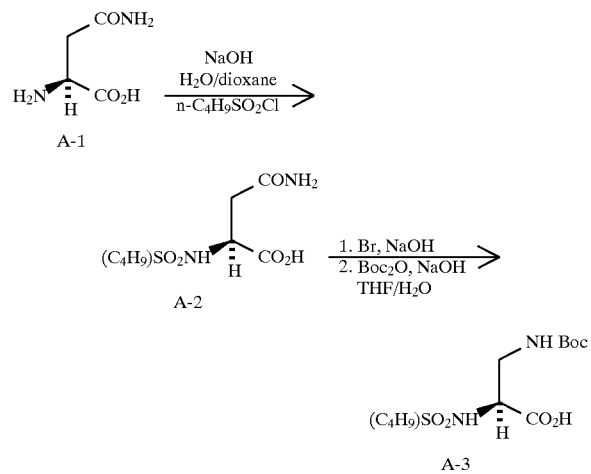

L-Asparagine-α-butanesulfonamide (also N-(n-Butylsulfonyl)-L-asparagine) A-2

A solution containing L-asparagine (6.45 g, 48.9 mmol) and NaOH (2.0 g, 50.0 mmol) in 100 ml of 50% aqueous dioxane was cooled to 0° in an ice bath. To this rapidly stirred mixture, a solution of NaOH (2.2 g, 55.0 mmol) in 50 ml of water and neat butane sulfonyl chloride (7.0 ml, 53.9 mmol) were added alternately over a period of 30 min. The reaction solution was concentrated to a volume of 50 ml at reduced pressure and aqueous residue was cooled, acidified with concentrated HCI, and extracted into ethyl acetate (3×100 ml). The organic extracts were dried over $Na_2SO_4$ and concentrated to a volume of approximately 50 ml, anhydrous ether (50 ml) was added and the resulting white precipitate was isolated by vacuum filtration yielding A-2, mp. 154°–155°.

L-βBoc-α-butane sulfonamido-βamino alanine (also 2(S)-(n-Butyl-sulfonylamino)-3-(N-Boc-aminopropionic acid) A-3

A solution containing NaOH (6.04 g, 151 mmol) in 50 ml $H_2O$ was cooled to 0° and bromine (1.40 ml, 26.9 mmol) was added. The resulting solution was stirred at 0° for 5 min. Next, a cooled solution of A-2 (5.23 g, 20.7 mmol) and NaOH (1.66 g, 41.4 mmol) in 15 ml of $H_2O$ was added at once and mixture stirred at 0° for 5 min then heated to 80° for 15 min. The solution was then cooled to 25° and acidified with 12N HCl (11 ml) and stirred until gas evolution ceased. The solution was then made basic by the addition of 2N NaOH and 20 ml of THF was added along with di-t-butyldicarbonate (9.0 g, 41.4 mmol). After stirring overnight at 25° the THF was removed at reduced pressure and the basic aqueous phase extracted with ethyl acetate (2×50 ml). The aqueous phase was then made acidic with 10% $KHSO_4$ and extracted with ethyl acetate (3×100 ml). The pooled acidic extracts were dried over $Na_2SO_4$ filtered and evaporated giving A-3 as a white solid, mp 111°–112°.

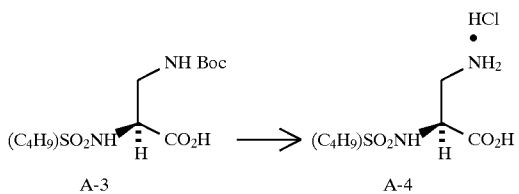

2(S)-(n-Butylsulfonylamino)-3-aminopropionic acid (A-4)

A solution of A-3 (3.83 g, 11.8 mmol) in 200 ml of ethyl acetate was cooled to 0°, HCl gas was bubbled through the solution for 5 min. The solution was then warmed to 25° and stirred for 30 min then concentrated at reduced pressure to 50% of its volume and diluted with 100 ml of ether. The resulting white solid was collected by vacuum filtration giving A-4 as a solid.

Ethyl 2(S)-(n-Butylsulfonylamino)-3-amino propionate (A-5)

A solution of A-4 (1.0 g, 3.8 mmol) in 50 ml of anhydrous ethanol was saturated with HCl gas then heated at reflux for 3.0 h. The solvent was evaporated to afford pure A-5 as a white solid.

$^1$H NMR (300 MHz, $CD_3OD$) δ 4.38 (m, 2H); 4,32 (m, 1H); 4.23 (m, 2H); 2.85 (m, 2H); 1.65–1.45 (m, 4H); 1.3 (t, 2H); 0.96 (t, 3H).

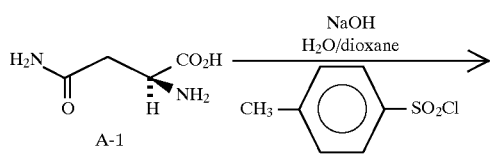

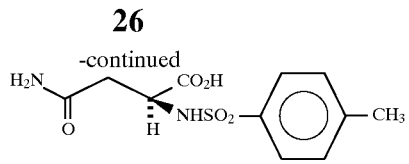

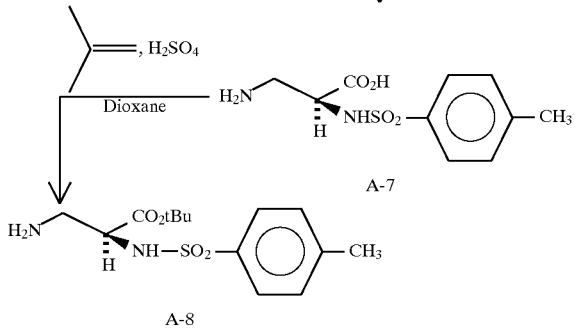

N-Tosyl-L-Asparagine (A-6): L-Asparagine (10.0 g, 75.7 mmol) was placed in a 500 ml round bottom flask equipped with a magnetic stir bar and an addition funnel. 1N Sodium hydroxide (85 ml, 1.1 eq.) was added. p-Toluenesulfonyl chloride (15.88 g, 83.27 mmol) was dissolved in ethyl acetate (100 ml). This solution was added to the reaction flask with vigorous stirring. 1N Sodium hydroxide (85 ml, 1.1 eq.) was placed in the addition funnel, then added dropwise with vigorous stirring over a 2 h period. The reaction mixture was stirred an additional 2 h, at room temperature. The organic and aqueous layers were separated and the aqueous layer was washed with ethyl acetate (2×50 ml). The aqueous liquid was cooled to 0° then acidified with hydrochloric acid (conc.). A white crystalline solid was obtained. Recrystallization from hot water yielded A-6.

$^1$H NMR (300 MHz DMSO-$d_6$) δ 7.91 (d, J=8.79 Hz, 1H); 7.64 (d, J=8.06 Hz, 2H); 7.32 (s, d (overlapping), J=8.06 Hz, 3H); 6.87 (s, br, 1H); 4.03 (m, 1H); 3.32 (s, $H_2O$); 2.49 (m, 1H); 2.43 (d, d, J=7.08, 15.38 Hz, 1H); 2.35 (s, 3H); 2.21 (d, d, J=6.11, 15.38 Hz, 1H).

2(S)-Tosylamino-3-aminopropionic acid (A-7)

A solution containing NaOH (22.0 g, 550 mmol) in 100 ml $H_2O$ was cooled to 0° and bromine (5.03 ml, 97.5 mmol) was added dropwise. The resulting solution was stirred at 0° for 10 min., then a cooled (0°) solution of A-6 (21.5 g, 75.0 mmol) and NaOH (6.68 g, 161 mmol) in $H_2O$ (50 ml) was added in a single portion. After stirring at 0° for 20 min, the reaction was heated to 80° for 30 min, then cooled. The cooled solution was adjusted to pH=7 with concentrated HCl and the resulting white solid filtered to give A-7.

$^1$H NMR (300 MHz, DMSO-$d_6$) δ 8.2–7.2 (br, 2H, (NH,COOH)); 7.70 (d, J=8.18 Hz, 2H); 7.38 (J=8.18 Hz, 2H); 3.7–3.0 (br, 2H, (NH2, $H_2O$)); 3.12 (q, J=4.76 Hz, 1 H); 2.99 (d, d, J=4.64, 11.96 Hz, 1H); 2.79 (d, d, J=9.52, 11.96 Hz, 1H); 2.36 (s, 3H).

tert-Butyl-2(S)-(Toluenesulfonylamino)-3-amino propionic acid (A-8)

A-7 (5.0 g, 19.4 mmol) was suspended in Dioxane (100 ml) in a 1 liter pressure bottle. The bottle was cooled to −15° C. and isobutylene (100 ml) was condensed into the dioxane. Concentrated $H_2SO_4$ (5 ml) was added and the bottle sealed and stirred at room temperature for 36 h. The bottle was opened, and the excess isobutylene carefully vented. The solution was diluted with ethyl acetate (200 ml) and washed with 1N NaOH, (200 ml). The organic layer was dried (Na₂SO₄), filtered and evaporated to give A-8 as a white crystaline solid.

¹H NMR (300 MHz, CDCl₃) δ 7.68 (d, J=8.18 Hz, 2H); 7.35 (d, J=8.18 Hz, 2H); 3.85 (m, H); 2.93–2.79 (m, 2H); 2.32 (s, 3H); 1.38 (s, 9H).

SCHEME 1

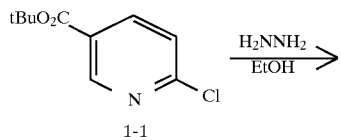

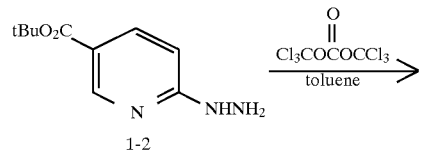

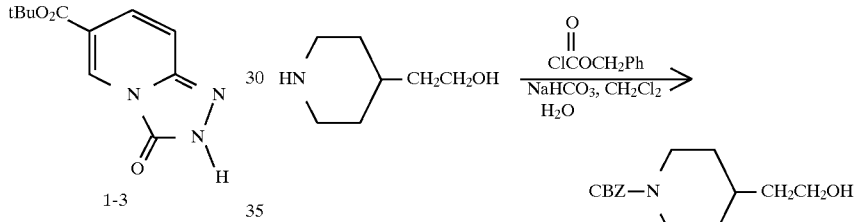

tert-Butyl 2-Hydrazinopyridine-3-carboxylate (1-2

A solution of tert-butyl 6-chloro-nicotinate (735 mg, 3.44 mmol) in ethanol (5 mL) was cooled to 0° and treated with anhydrous hydrazine (2.75 g, 86 mmol) dissolved in ethanol (5 mL). This mixture was allowed to reach 25° and stirred 20 h and then warmed to 60° for 2 h. The mixture was dissolved in water and extracted with ethyl acetate. The organic portion was washed with water and brine, dried (Na₂SO₄), and concentrated to give 1-2 as an oil that was used directly in the next step.

tert-Butyl [2,3-Dihydro-3-oxo-1,4-triazolo-[4,3-a]pyridin-6-yl]-carboxylate (1-3)

1-2 was dissolved in 35 mL of toluene and slowly added to a refluxing solution of bis(trichloromethyl)carbonate (1.15 g, 3.9 mmol) in toluene (35 mL). This was further refluxed for 1.2 h and cooled, added to water and extracted with ethyl acetate. The organic portion was dried (Na₂SO₄), concentrated, and flash chromatographed on silica gel to yield 1-3.

¹H NMR (DMSO-d₆, 300 MHz): δ=1.58 (s,9H); 7.25 (d, 1H); 7.45 (d,1H); 8.25 (s, 1H); 12.40 (s, 1H).

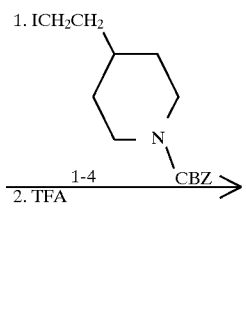

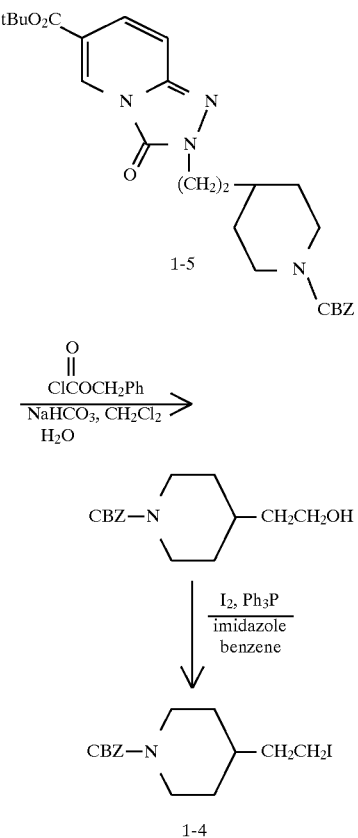

2(N-CBZ-Piperidin-4-yl)ethyl iodide (1-4)

A mixture of [4-(2-hydroxyethyl)piperidine] (Aldrich) (5.0 g, 38.7 mmol), sat. NaHCO₃ (50 ml) and CH₂Cl₂ (150 ml) was treated with benzyl chloroformate (6.05 ml, 42.5 mmol). After stirring at room temperature for 2.5 h, the organic layer was removed and washed with H₂O and brine, dried (Na₂SO₄), then filtered and concentrated to give the protected alcohol as a colorless oil.

¹H NMR (300 MHz, CDCl₃) δ 7.26 (m, 5H); 5.13 (s, 2H); 4.23 (d, 2H); 3.63 (t, 2H); 2.85 (t, 2H); 1.83 (d, 2H); 1.68 (m, 2H); 1.43 (m, 1H); 1.03 (m, 2H);

This protected alcohol (6.3 g, 23.9 mmol) was combined with Ph₃P (7.0 g, 23.9 mmol), iodine (6.06 g, 23.9 mmol), and imidazole (1.95 g, 28.7 mmol) in benzene (100 ml) and refluxed for 2.5 h. The solution was cooled, filtered and then concentrated. The residue was chromatographed on silica gel (1:1 ethyl acetate/Hexane) to give 1-4 as a white solid.

$^1$H NMR (300 MHz, CDCl$_3$) δ 7.26 (m, 5H); 5.14 (s, 2H); 4.23 (d, 2H); 3.86 (m, 4H); 1.85 (d, 2H); 1.68 (m, 2H); 1.45 (m, 1H); 1.03 (m, 2H).

3-[[(2,3-dihydro-3-oxo-[2-(N-CBZ-Piperidin-4-yl)ethyl]-1,2,4-triazolo[4,3-a] pyridin-6-yl]carboxylic acid (1-5)

1-3 (350 mg, 1.6 mmol) dissolved in 20 ml of acetonitrile was treated with powdered potassium carbonate (630 mg) and heated to 60° for 20 h. The mixture was cooled to 25° added to water and extracted with ethyl acetate. The organic portion was dried (Na$_2$SO$_4$), concentrated, and flash chromatographed on silica gel (35% ethyl acetate in hexane) to give the desired ester as a yellow oil.

The crude tert-butyl ester was converted to the acid by treating with 15 mL of methylene chloride and 15 mL of trifluoroacetic acid at 0° and then warming to 25° for 1.2 h. The mixture was concentrated to dryness under vacuum, added to water and extracted with ethyl acetate. The organic portion was dried (Na$_2$SO$_4$), concentrated, and crystallized from ethylacetate/ether (25/1) to give 1-5 as a pale yellow powder.

$^1$H NMR (DMSO-d$_6$, 300 MHz): δ=1.05 (m, 2H); 1.45 (m, 1H); 1.75 (m, 4H); 2.79 (m,2H); 3.95 (q, 4H); 5.05 (s, 2H); 7.30 (m, 6H); 7.50 (d, 1H); 8.25 (s, 1H).

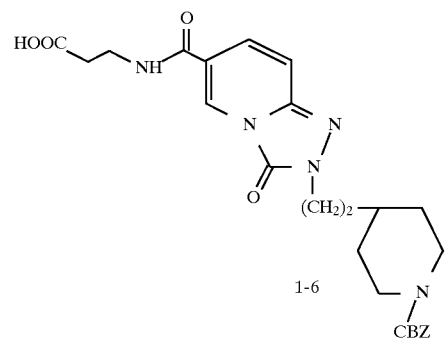

3-[[[(2,3-Dihydro-3-oxo-2[2-(N-CBZ-Piperidin-4-yl)ethyl]-1,2,4-triazolo[4,3-a]Pyridin-6-yl]carbonyl]amino]propionic acid (1-6)

A solution of 1-5 (75 mgs, 0.18 mmol) in dimethylformamide (1 mL) was treated sequentially with hydroxybenztriazole (40 mgs, 0.26 mmol), diisopropyl ethyl amine (87 μl, 0.5 mmol), ethyl 2-aminopropionate hydrochloride (40 mgs, 0.26 mmol), and EDC (50 mgs, 0.26 mmol). This mixture was stirred at 25° for 15 h. The mixture was dissolved in water and extracted with ethyl acetate. The organic portion was washed with water and brine, dried (Na$_2$SO$_4$), and concentrated to provide the desired ester.

This crude ethyl ester was dissolved in 5 mL of THF, 5 mL of water and treated with 0.37 mL of 1N aqueous LiOH solution. This was stirred 3 h at 25°. The mixture was dissolved in water and extracted with ethyl acetate. The organic portion was washed with water and brine, dried (Na$_2$SO$_4$), and concentrated to a provide 1-6, mp 201°–203° (dec).

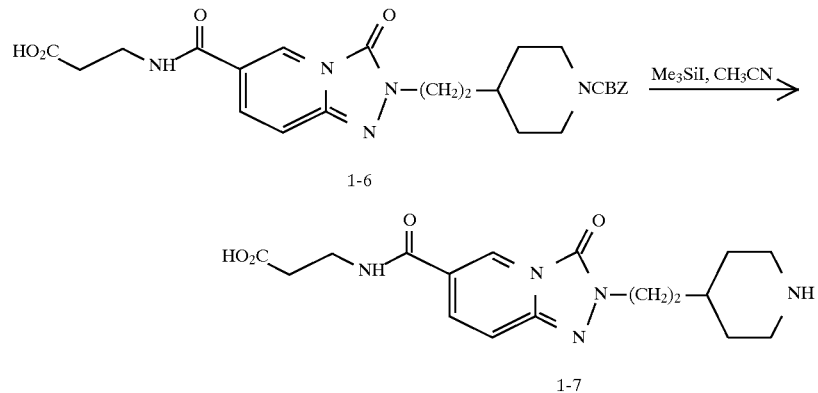

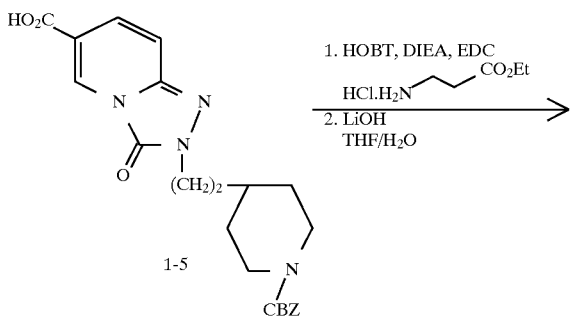

3-[[[(2,3-Dihydro-3-oxo-2-(2-(piperidin-4-yl)ethyl]-1,2,4-triazolo-[4,3-a]pyridin-6-yl]carbonyl]amino]propionic acid (1-7)

A solution of 1-6 (64 mg, 0.129 mmole) in acetonitrile (15 ml) at 0° was treated with iodotrimethylsilane (107.0 mg, 0.533 mmole) and the reaction stirred 0.5 h. The reaction was quenched into water, extracted with diethyl ether and chromatographed on silica using EtOH/NH$_4$OH/H$_2$O (10/1/1) to give upon concentration a white foam. Crystallization from ethanol gave 1-7 as a white solid, mp 267°–269°.

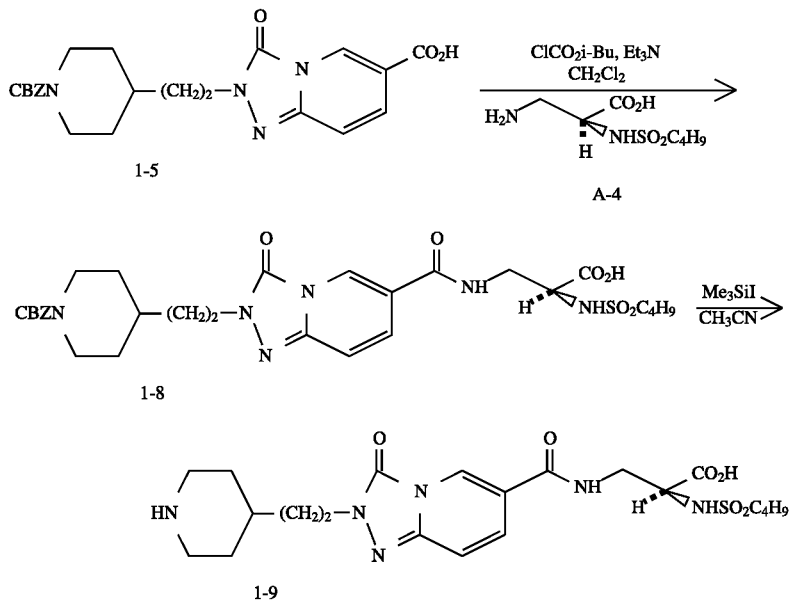

2(S)-[6-Butylsulfonyl)amino]-3[[[2,3-dihydro-3-oxo-2-[2-(N-CBZ-Piperidin-4-yl)ethyl]-1,2,4-triazolo[4,3-a]Pyridin-6-yl]carbonyl[amino Propionic acid (1-8)

1-5 was coupled to A-4 as described for 1-6 to provide 1-8.

$^1$H NMR (300 MHz, DMSO d$_6$) δ 8.26 (t, 1H), 8.50 (s, 1H); 7.63 (d, 1H); 7.54 (d, 1H); 7.4–7.31 (m, 6H); 5.01 (s, 2H); 4.10 (m, 1H); 3.96 (m, 4H); 3.60 (m, 1H); 3.46 (m, 1H); 2.95 (t, 2H); 2.73 (brm, 2H); 1.71 (m, 2H); 1.53 (m, 2H); 1.46 (m, 1H); 1.01 (m, 2H); 0.83 (t, 3H).

2(S )-[(n-Butylsulfonyl)amino]-3[[[2,3-dihydro-3-oxo-2-[2-(piperidin-4-yl)ethyl]- 1,2,4-triazolo[4,3-a]Pyridin-6-yl] carbonyl]amino propionic acid (1-9)

1-8 was treated with trimethylsilyl iodide in CH$_3$CN as described for 1-7 to afford 1-9.

$^1$H NMR (300 MHz, D$_2$O) δ 8.10 (s, 1H); 7.43 (d, 1H); 7.15 (d, 1H); 4.00 (m, 4H); 3.60 (d, 2H); 3.31 (m, 2H); 3.23 (d, 2H); 3.93 (m, 2H); 3.81 (t, 2H); 1.93 (d, 2H); 1.80 (m, 2H); 1.6–1.23 (m, 7H); 0.85 (t, 3H).

SCHEME 2

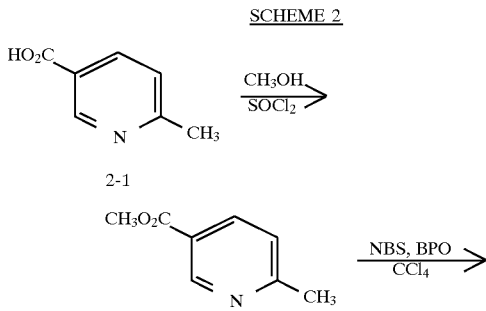

-continued
SCHEME 2

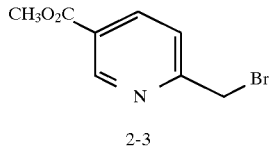

Methyl 6-methylpyridin-3-carboxylate (2-2)

A solution of 6-methyl nicotinic acid, 2-1 (5 g, 36.5 mmol) in 100 ml of anhydrous methanol was placed in a 250 ml three neck flask equipped with a dropping funnel vertical condenser and CaCl$_2$ drying tube. The reaction solution was cooled to −15° in an ice acetone bath and SOCl$_2$ (5 ml, 69.1 mmol) was added dropwise. The solution was then heated at reflux for 3 h then cooled and the solvent removed at reduced pressure. The resulting white solid was treated with 60 ml of saturated NaHCO$_3$ and extracted into CH$_2$Cl$_2$ (3×50 ml). The pooled extracts were dryed (Na$_2$SO$_4$), filtered and evaporated at reduced pressure. The resulting oil crystallized on standing giving 2-2 as a white solid.

$^1$H NMR (300 MHz, CDCl$_3$) δ 9.05 (d, J=1.4 Hz, 1H); 8.08 (dd, J=1.4 and 6.8 Hz); 7.19 (d, J=6.8 Hz, 1H); 3.98 (s, 3H); 2.63 (s, 3H).

Methyl 6-Bromoethylpyridine-3-carboxylate (2-3)

2-2 (10.6 g, 71.5 mmol) was combined with NBS (12.73 g, 71.5 mmol), 100 mg benzoyl peroxide and 200 ml CCl$_4$ and refluxed under an inert atmosphere for 18 h. The reaction solution was cooled, filtered, and concentrated to a viscous orange oil which was flash chromatographed on silica gel using 20% ethyl acetate in hexane giving the desired pyridyl bromide 2-3.

$^1$H NMR (300 MHz, CDCl$_3$) δ 9.05 (d, J=1.4 Hz, 1H); 8.08 (dd, J=1.4 and 6.8 Hz); 7.19(d, J=6.8 Hz, 1H); 5.38 (s, 2H); 3.98 (s, 3H).

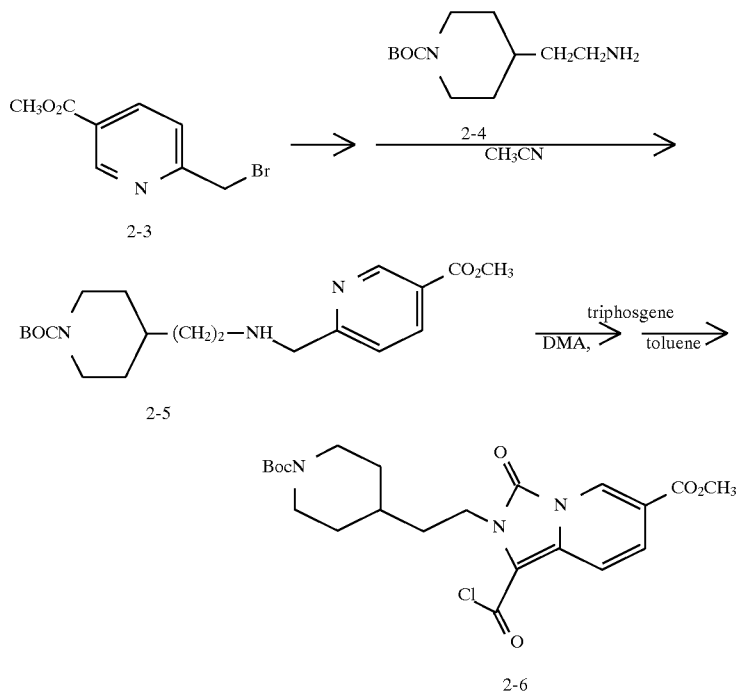

Methyl 6-[2-(N-Boc-Piperidin-4-yl)ethylamino]-methylpyridine-3-carboxylate (2-5)

A mixture of 2-3 (1.0 g, 4.34 mmol), 2-4 (2.16 g, 10.0 mmol) and K₂CO₃ (0.66 g, 4.4 mmol) in 100 ml of anhydrous CH₃CN was placed in a 250 ml flask and refluxed for 3 h then cooled and filtered. The filtrate was concentrated at reduced pressure and chromatographed on silica gel using 10% CH₃OH/EtOAc as eluent to afford 2-5 as a yellow residue.

¹H NMR (CDCl₃) δ 9.18 (d, J=1.4Hz, 1H); 8.15 (dd, J=1.4 and 6.8 Hz, 1H); 7.39 (d, J=6.8 Hz, 1H); 4.08 (br d, J=12 Hz, 2H); 3.98 (s, 2 H); 3.95 (s, 3H); 2.75 (overlapping m, 6H); 1.78 (d, J=12.Hz, 2H); 1.5 (overlapping m, 4H); 1.4 (s, 9H); 0.98 (m, 2H).

Methyl 1-(Chlorocarbonyl)-2,3-dihydro-3-oxo-2-[[2-(N-Boc-piperidin-4-yl)ethyl]imidazo[1,5-a]pyridin-6-yl] carboxylate (2-6)

2-5 (480 mg, 1.27 mmol) was dissolved in 50 ml of toluene, N,N- dimethyl aniline (645 ml, 4.08 mmol) was added and the solution cooled to 0°. To this, a solution of triphosgene (1.13 g, 3.18 mmol) in 15 ml toluene was added dropwise over 30 min. The solution was then heated to 100° for 1.5 h then cooled, washed twice with 1N HCl, water and brine (50 ml of each), dried over Na₂SO₄ and evaporated giving 515 mg of a yellow crystalline, solid 2-6.

¹H NMR (CDCl₃) δ 8.82 (d, J=1.4Hz, 1H); 8.25(d, J=6.8 Hz, 1H); 7.91 (d, J=6.8 Hz, 1H) (dd, J=1.4 and 6.8 Hz,1 H; 4.08 (br d, J=12 Hz, 2H); 3.98 (s, 2 H); 3.95 (s, 3H); 2.75 (overlapping m, 6H); 1.78 (d, J=12.Hz, 2H); 1.5 (overlapping m, 4H); 1.4(s, 9H); 0.98 (m, 2H).

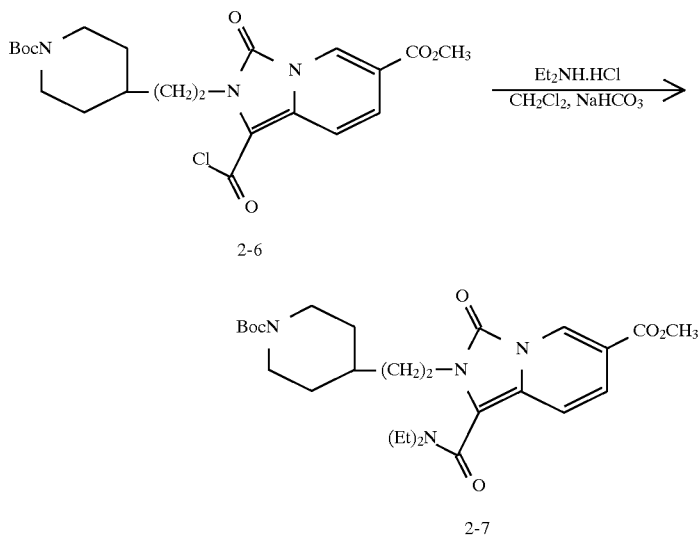

Methyl 1-[(N,N-Diethylamino)carbonyl]-2,3-dihydro-3-oxo-2-[[2-(N-Boc-piperidin-4-yl)ethyl]-imidazo[1,5-a]pyridin-6-yl]carboxylate (2-7)

2-6 (0.3 g, 0.64 mmol) was dissolved in 100 ml of $CH_2Cl_2$ and diethylamine hydrochloride (105 mg, 0.97 mmol) was added along with 50 ml of saturated $NaHCO_3$ solution. This biphasic mixture was stirred for 1 h, then the organic layer was separated and washed with 10% citric acid then brine (50 ml), dried over $Na_2SO_4$ and evaporated giving 2-7.

$^1$H NMR (CDCl$_3$) δ 8.45 (d, J=1.4Hz, 1H); 7.15 (dd, J=1.4 and 6.8 Hz, 1H); 6.78 (d, J=6.8 Hz, 1H); 4.08 (m, 4H); 3.95 (s, 3H); 3.51 (m, 4H); 2.75 (m, 3H); 1.78 (d, J=12.Hz, 2H); 1.5 (over lapping m, 4H); 1.4 (s, 9H); 1.1 (t, 6H); 0.98 (m, 2H).

tert-Butyl-1[[(N,N-diethylamino)carbonyl]-2,3-dihydro-3-oxo-2[2-(N-Boc-piperidin-4-yl)ethyl]imidazo[1,5-a]Pyridin-6-yl]carbonyl]amino propionate (2-8)

2-7 (315 mg, 0.64 mmol) was dissolved in 10 ml of $CH_3OH$, 15 ml $H_2O$ and 0.725 ml 1N NaOH added and mixture stirred at room temperature for 3.5 h. The organic solvent was removed at reduced pressure and the aqueous residue acidified with citric acid and extracted with $CH_2Cl_2$. The organic extracts were washed with $H_2O$, and brine then dried over $Na_2SO_4$ filtered and evaporated to give the desired acid.

$^1$H NMR (CDCl$_3$) δ 8.32 (d, J=1.4Hz, 1H); 7.10 (dd,=1.4 and 6.8 Hz, 1H); 6.78 (d, J=6.8 Hz, 1H); 4.08 (m, 4H); 3.51 (m, 4H); 2.75 (m, 3H); 1.78 (d, J=12.Hz, 2H); 1.5 (overlapping m, 4H); 1.4 (s, 9H); 1.1 (t, 6H); 0.98 (m, 2H).

This acid (105 mg, 0.215 mmol) was dissolved in 10 ml of $CH_2Cl_2$, $Et_3N$ (48 ml, 0.47 mmol) was added and solution cooled to −10°. Next, isobutyl chloroformate (30 ml, 2.36 mmol) was added and the mixture stirred at −10° for 30 min. To this a solution of β-alanine tert-butyl ester hydrochloride (58.7 mg, 323 mmol) and $Et_3N$ (32 ml, 0.323 mmol) in 10 ml of $CH_2Cl_2$ was added and solution warmed to room temperature. Reaction solution washed with 10% citric acid, $H_2O$ and brine (10 ml each) and dried over $Na_2SO_4$, concentrated and chromatographed giving 2-8.

$^1$H NMR (CDCl$_3$) δ 8.16 (s, 1H); 7.02 (d, J=6.8 Hz, 1H); 6.78 (d, J=6.8 Hz, 1H); 6.63 (t, 5.6Hz, 1H); 4.08 (m, 4H); 3.51 (m, 6H); 2.75 (m, 2H); 2.45 (m, 2H); 1.78 (d, J=12.Hz, 2H); 1.5 (overlapping m, 6H); 1.4 (s, 9H); 1.37 (s, 9H); 1.1 (t, 6H); 0.98 (m, 2H).

1-[(N,N-Diethylamino)carbonyl]-2,3-dihydro-3-oxo-2[2-(piperidin-4-yl)ethyl]imidazo[1,5-a]pyridin-6-yl]carbonyl] propionic acid (2-9)

2-8 (100 mg, 0.16 mmol) was dissolved in 20 ml of ethyl acetate anhydrous HCl was passed through the solution at 0° C. for 5 min then the mixture was stirred at room temperature for 1 h. The solvent was evaporated at reduced pressure and the residue triturated with ethyl acetate and filtered to give 2-9.

$^1$H NMR (DMSO-d$_6$) δ 8.90 (br s, 1H); 8.60 (br s, 1H); 8.3 (s, 1H); 7.6 (t, 3H); 7.1 (d, 1H); 6.89 (d, 1H); 4.08 (m, 4H); 3.51 (m, 6H); 2.75 (m, 2H); 2.45 (m, 2H); 1.78 (d, J=12.Hz, 2H); 1.5 (overlapping m, 6H); 1.1 (t, 6H); 0.98 (m, 2H).

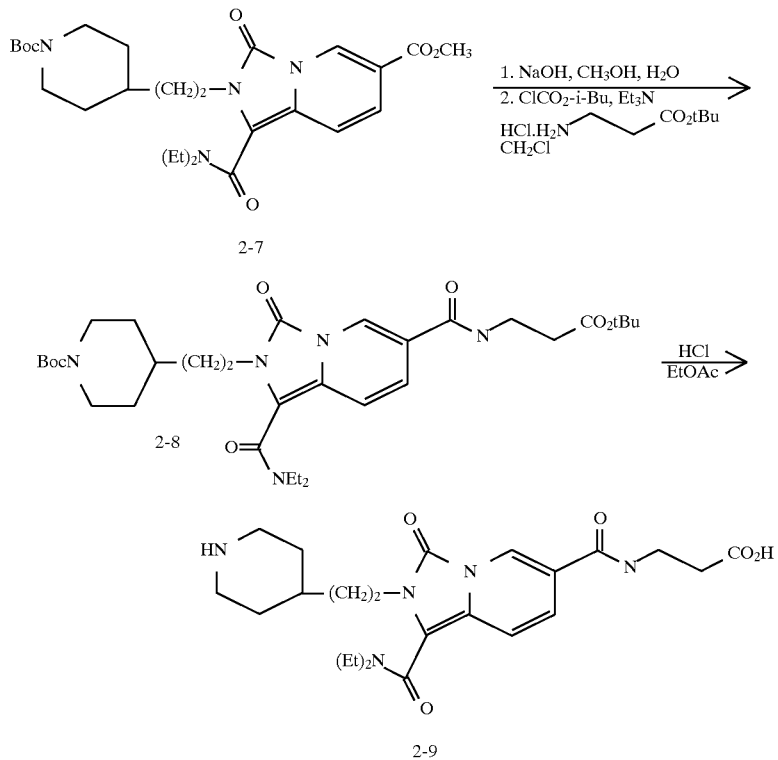

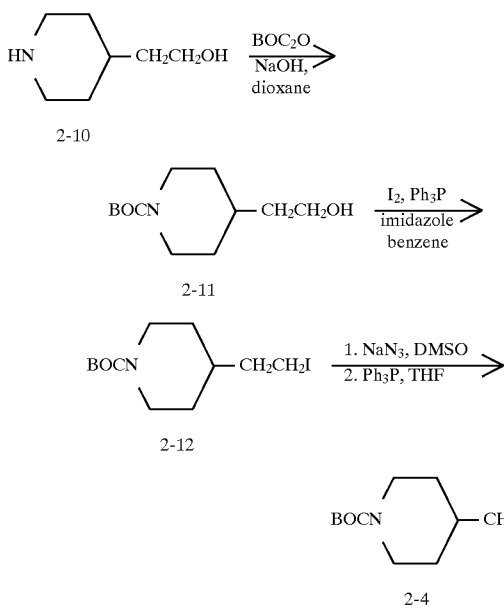

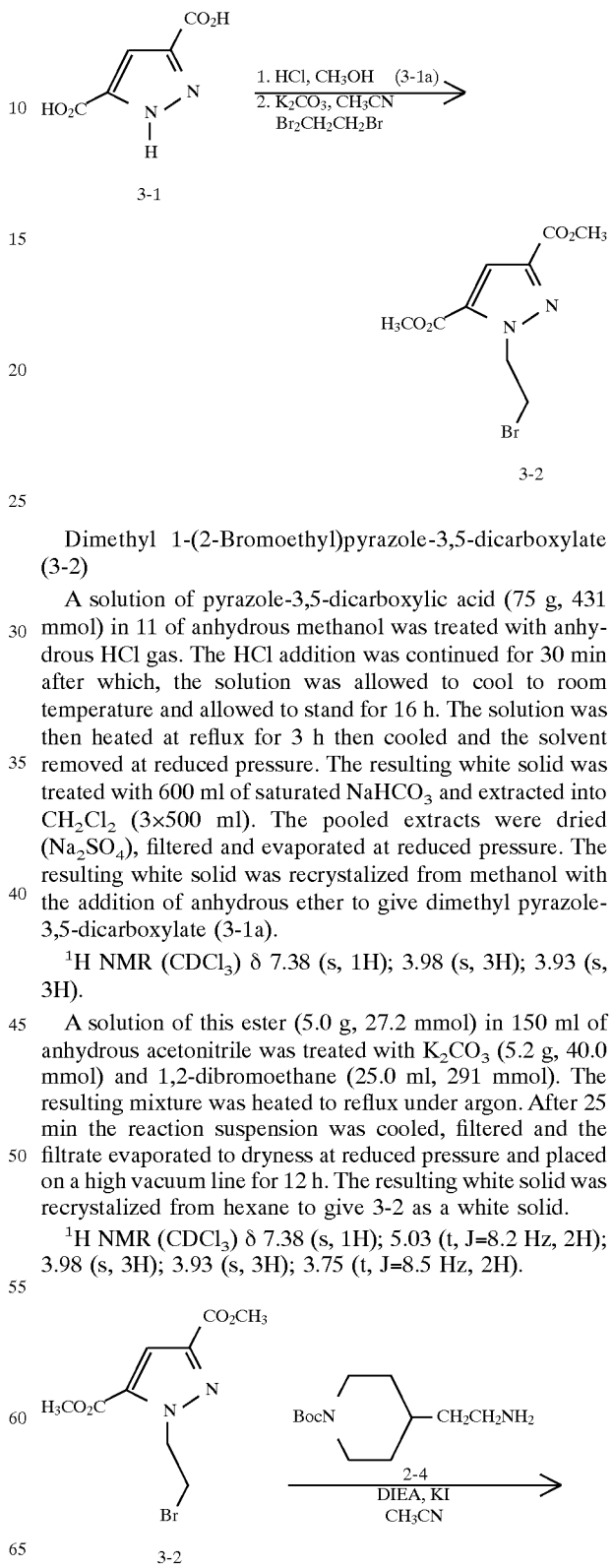

2-(N-Boc-Piperidin-4-yl)ethanol (2-11)

4-Piperidine-2-ethanol (2-10) (Aldrich) (130 g, 1.0 mole) was dissolved in 700 mL dioxane, cooled to 0° and treated with 3 N NaOH (336 mL, 1.0 mole), and di-t-butyldicarbonate (221.8 g, 1.0 mole). The ice bath was removed and the reaction stirred overnight. The reaction was concentrated, diluted with water and extracted with ether. The ether layers were combined, washed with brine, dried over $MgSO_4$, filtered and evaporated to give 2-11.

$R_f$=0.37 in 1:1 EtOAc/Hexances, ninhydrin stain.

$^1$H NMR (300 MHz, $CDCl_3$) δ 4.07 (bs, 2H); 3.7 (bs, 2H); 2.7 (t, J=12.5 Hz, 2H); 1.8–1.6 (m, 6H); 1.51 (s, 9H); 1.1 (ddd, J=4.3, 12.5, 12 Hz, 2H).

2-(N-Boc-Piperidin-4-yl)ethyl iodide (2-12)

2-11 (10.42 g, 0.048 mol) was dissolved in 400 ml benzene, imidazole (4.66 g, 0.068 mol), triphenylphosphine (15.24 g, 0.05 mol) and iodine (0.048 mol) were added at room temperature. After 6 hours the reaction mixture was filtered and the filtrate was evaporated to give a dark residue. This was purified by flash chromatography on silica gel eluting with 10% EtOAc-hexanes to give 2-12 as a yellow oil.

2-(N-Boc-Piperidin-4-yl)ethyl amine (2-4)

To 2-12 (27.9 g, 0.082 moles) dissolved in DMSO (400 ml) was added sodium azide (5.01 g, 0.086 moles) as room temperature and the resulting solution was heated at 65° for 2 h. The cooled reaction mixture was diluted with 250 ml EtOAc, extracted with 2×100 ml portions of water 2×50 ml portions of brine and then dried ($MgSO_4$). Solvent removal provided the desired azide as a pale yellow oil, $R_f$ 0.5 (silica gel, 70% acetone/hexane).

This azide (19.3 g, 0.076 moles) in THF (400 ml)/$H_2O$ (195 ml) was added triphenylphosphine (80.0 g, 0.305 moles) in one portion at room temperature. This was stirred at room temperature 3 hours and the organic solvents were then removed in vacuo. The residue was acidified to pH 2 with 10% $KHSO_4$ solution and this was extracted 4×100 ml portions of EtOAc. The organic extract was extracted with 2×100 mol portions of 10% $KHSO_4$ and the aqueous phases were combined and the pH was adjusted to 10 with 2N NaOH. This solution was extracted with 4×200 ml portions of $CH_2Cl_2$. These were combined, dried ($MgSO_4$) and the solvent was removed to give 2-4 as an oil. $R_f$ 0.3 (silica gel, eluting with 10% $CH_3OH$ in $CHCl_3/NH_3$).

$^1$H NMR (300 MHz, $CDCl_3$) δ 4.05 (broad, 2H); 2.72 (t, J=7.2 Hz, 2H); 2.62 (m, 2H); 1.64 (d, J=12.2 Hz, 2H); 1.43 (s, 9H); 1.42–1.32 (m, 5H); 1.09 (m, 2H).

SCHEME 3

Dimethyl 1-(2-Bromoethyl)pyrazole-3,5-dicarboxylate (3-2)

A solution of pyrazole-3,5-dicarboxylic acid (75 g, 431 mmol) in 1 l of anhydrous methanol was treated with anhydrous HCl gas. The HCl addition was continued for 30 min after which, the solution was allowed to cool to room temperature and allowed to stand for 16 h. The solution was then heated at reflux for 3 h then cooled and the solvent removed at reduced pressure. The resulting white solid was treated with 600 ml of saturated $NaHCO_3$ and extracted into $CH_2Cl_2$ (3×500 ml). The pooled extracts were dried ($Na_2SO_4$), filtered and evaporated at reduced pressure. The resulting white solid was recrystalized from methanol with the addition of anhydrous ether to give dimethyl pyrazole-3,5-dicarboxylate (3-1a).

$^1$H NMR ($CDCl_3$) δ 7.38 (s, 1H); 3.98 (s, 3H); 3.93 (s, 3H).

A solution of this ester (5.0 g, 27.2 mmol) in 150 ml of anhydrous acetonitrile was treated with $K_2CO_3$ (5.2 g, 40.0 mmol) and 1,2-dibromoethane (25.0 ml, 291 mmol). The resulting mixture was heated to reflux under argon. After 25 min the reaction suspension was cooled, filtered and the filtrate evaporated to dryness at reduced pressure and placed on a high vacuum line for 12 h. The resulting white solid was recrystalized from hexane to give 3-2 as a white solid.

$^1$H NMR ($CDCl_3$) δ 7.38 (s, 1H); 5.03 (t, J=8.2 Hz, 2H); 3.98 (s, 3H); 3.93 (s, 3H); 3.75 (t, J=8.5 Hz, 2H).

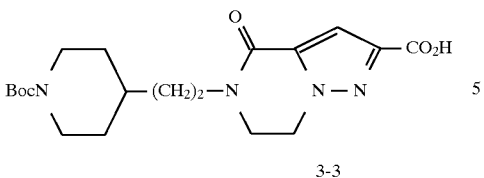

Methyl-[4,5,6,7-Tetrahydro-4-oxo-5-[2(N-Boc-Piperidin-4-yl)ethyl]-pyrazolo[1,5-a]pyrazin-2-yl]carboxylate (3-3)

A solution of 3-2 (14.0 g, 48.0 mmol), diisopropylethyl amine (25 ml, 144 mmol), Boc-4-aminoethylpiperidine (12.0 g, 52.6 mmol), and potassium iodide (2.39 g, 0.3 mmol) in 250 ml $CH_3CN$ was refluxed under $N_2$ for 4.5 h then cooled, filtered and evaporated at reduced pressure. The resulting yellow residue was chromatographed on silica gel using EtOAc as eluent to give 3-3 as an off-white crystalline solid.

$^1$H NMR (300 MHz, $CDCl_3$) δ 7.15 (s, 1H); 4.29 (t, J=7.0 Hz, 2H); 3.93 (br d, J=12 Hz, 2H); 3.76 (s, 3H); 3.61 (t, J=5.3 Hz, 2H); 3.42 (t, J=7.3 Hz, 2H); 2.65 (t, J=7.6 Hz, 2H); 1.55 (d, J=12.5 Hz, 2H); 1.38 (m, 2H); 1.33–1.25 (m, 1H); 1.27 (s, 9H); 1.01 (m, 2H).

A solution containing LiOH (14.05 mg, 0.335 mmol) in 10 ml $H_2O$ was added to a solution of 3-3 (90.81 mg, 0.223 mmol) in 10 ml $CH_3OH$ and the mixture was heated to 60° for 2.5 h then cooled, and the $CH_3OH$ removed at reduced pressure. The remaining aqueous phase was acidified with 10% aqueous citric acid and extracted with $CH_2Cl_2$ (2×50 ml). The pooled organic extracts were dried over $Na_2SO_4$ then evaporated to give the desired acid as a white solid.

$^1$H NMR (300 MHz, $CDCl_3$) δ 7.43 (s, 1H); 4.48 (t, J=7.0 Hz, 2H); 4.01 (br d, J=12 Hz, 2H); 3.77 (t, J=5.3 Hz, 2H); 3.51 (t, J=7.3 Hz, 2H); 2.71 (t, J=8.3Hz, 2H); 1.72 (d, J=12.5Hz, 2H); 1.53 (m, 2H); 1.42–1.37 (m, 1H); 1.35 (s, 9H); 1.10 (m, 2H).

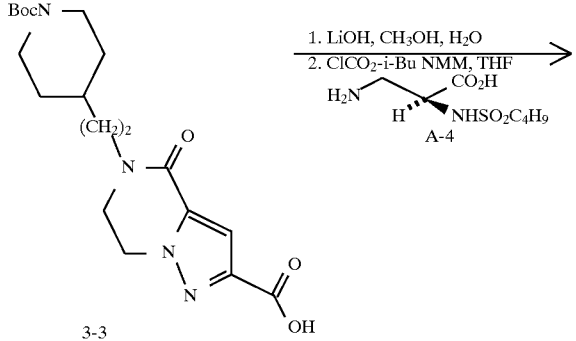

2(S)-[(n-Butylsulfonyl)amino-3[[[4,5,6,7-tetrahydro-4-oxo-5-[2-(N-Boc-piperidin-4-yl)ethyl]pyrazolo-[1,5-a]pyrazin-2-yl]carbonyl]amino propionic acid (3-4)

Isobutyl chloroformate (1.75 ml, 13.35 mmol) was added to a cooled solution (0°) containing this acid (4.98 g, 12.72 mmol) and N-methyl morpholine (1.53 ml, 14.00 mmol) in 100 ml THF. This mixture was stirred under an atmosphere of dry nitrogen. After reacting for 1 h, HPLC analysis of an aliquot indicated that the reaction was >90% complete. The N-methyl morpholine-HCl was removed by filtration and the filtrate poured into a solution containing A-4 (4.30 g, 16.54 mmol), diisopropylethylamine (4.27 ml, 33.10 mmol) THF (60 ml) and $H_2O$ (20 ml). The THF was then removed from the reaction solution at reduced pressure and the remaining aqueous portion acidified with sat. $KHSO_4$ and extracted with ethyl acetate (3×200 ml). Pooled extracts were dried over $Na_2SO_4$, filtered, and concentrated giving a red colored oil from which 3-4 formed as a white solid.

$^1$H NMR (DMSO-$d_6$) δ 8.31 (t, J=6Hz, 1H); 7.62 (d, J=8.5 Hz, 1H); 7.01 (s, 1H); 4.43 (t, J=6.6 Hz, 2H); 4.11 (m, 1H); 3.92 (d, J=12 Hz, 2H); 3.80 (t, J=6.6 Hz, 2H); 3.51 (t, J=7.3 Hz, 2H); 3.65 (m, 2H); 3.51 (t, J 6.8 Hz, 2H); 2.96 (t, J=7.2 Hz, 2H); 1.70 (d, J=11 Hz, 2H); 1.53 (m, 2H); 1.60–1.49 (overlapping m, 5H); 1.40 (s, 9H); 1.28 (q, J=7.1 Hz, 2H); 1.05 (m, 2H); 0.79 (t, J=7.1Hz, 3H).

2(S)-[(n-Butylsulfonyl)amino]-3-[[[4,5,6,7-tetrahydro-4-oxo-5-[2-(piperidin-4-yl)ethyl]pyrazolo[1,5-a]pyrazin-2-yl]carbonyl]amino propionic acid monohydrochloride (3-5)

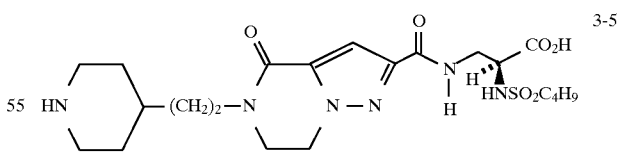

A solution of 3-4 (278 mg, 0.437 mmol) in 30 ml ethyl acetate was cooled to 0° and HCl gas bubbled through for 3 min. The reaction mixture was warmed to room temperature, stirred for 30 min then taken to dryness on a rotary evaporator. The remaining white solid was recrystalized from ethanol/water (90:10) filtered and vacuum dried over $P_2O_5$ giving 3-5 as a white solid.

$^1$H NMR (DMSO-d$_6$) δ 8.95 (br s, 1H); 8.33 (t, J=5.7 Hz, 1H); 7.64 (d, J=9 Hz, 1H); 7.02 (s, 1H); 4.35 (t, J=5.1 Hz, 2H); 4.10 (m, 1H); 3.81 (t, J=5.2 Hz, 2H); 3.6–3.4 (m, 4H); 3.21 (d, J=10.5 Hz, 2H); 2.95 (t, J=7.8 Hz, 2H); 2.81 (br m, 2H); 1.96 (d, J=11Hz, 2H); 1.62–1.2 (overlapping multiplets, 9H); 0.80 (t, J=7.3Hz, 2H).

SCHEME 4

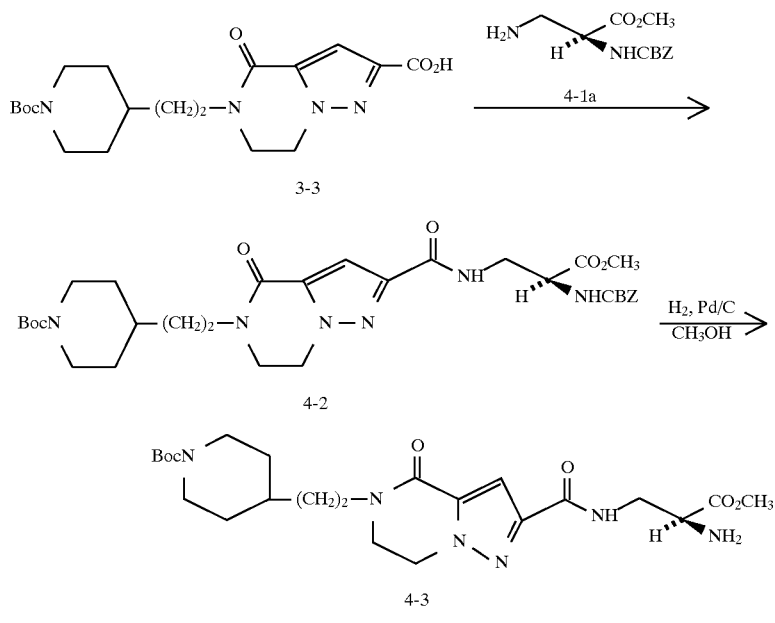

Methyl 2(S)-N-Benzyloxycarbonylamino-3-aminopropionate hydrochloride (4-1a)

Commercially available 2(S)-N-benzyloxycarbonylamino-3-aminopropionic acid (Fluka) was refluxed in methanolic HCl for 2.5 h then evaporated and the residue crystalized from methanol/ether to give 4-1a as a white solid.

$^1$H NMR (300 MHz, DMSO-d$_6$) δ 7.63 (m, 5H); 5.93 (d, 1H); 5.15 (s, 2H); 4.56 (m, 1H); 3.95–3.83 (m, 2H); 3.73 (s, 2H).

Methyl-2(S)-[(CBZ)amino]-3-[[[4,5,6,7-tetrahydro-4-oxo-5-[2(N-Boc-piperidin-4-yl)ethyl]pyrazolo[1,5-a]pyrazin-2-yl]carbonyl]amino]-propionate (4-2)

A solution of 3-3 (5.6 g, 14.0 mmol), N$_α$-Cbz-L-2,3-diaminopropionic acid methyl ester hydrochloride (4-1a) (4.5 g, 15.5 mmol), HOBT (2.37 g, 15.5 mmol), and Et$_3$N (4.1 ml, 29.5 mmol) in 65 ml anhydrous DMF was stirred under N$_2$ for 48 h at room temperature. The DMF removed at reduced pressure and the residue dissolved in 700 ml ethyl acetate and washed successively with saturated NaHCO$_3$ solution, H$_2$O, 10% citric acid, H$_2$O and brine (1×100 ml each), dried over Na$_2$SO$_4$, filtered and evaporated. The resulting clear glass was chromatographed on silica gel using 3% CH$_3$OH/CH$_2$Cl$_2$ as eluent to yield pure 4-2 as a white solid.

$^1$H NMR (CDCl$_3$) δ 7.43 (m, 5H); 7.35 (s, 1H); 7.18 (t, J=6.5 Hz, 1H); 5.98 (d, J=6.8 Hz, 1H); 5.09 (s, 2H); 4.59 (m, 1H); 4.38 (m, 2H); 4.10 (br d, J=12 Hz, 2H); 3.8 (s, 3H); 3.73 (t, J=5.3 Hz, 2H); 2.71 (t, J=8.3 Hz, 2H); 1.72 (d, J=12.5 Hz, 2H); 1.53 (m, 2H); 1.42–1.37 (m, 1H); 1.35 (s, 9H); 1.10 (m, 2H).

Methyl-2(S)amino-3-[[[4,5,6,7-tetrahydro-4-oxo-5-[2(N-Boc-piperidin-4-yl)ethyl]pyrazolo[1,5-a]pyrazin-2-yl]carbonyl]amino]propionate (4-3)

To 4-2 (6.3 g, 10.26 mmol) in 700 ml CH$_3$OH was added 650 mg 10% Pd on C and the resulting mixture stirred under 1 atm of H$_2$ for 48 h. The catalyst was removed by filtration through celite and the filtrate concentrated to give a colorless glass which was triturated with Et$_2$O and filtered to afford 4-3 as a white solid.

$^1$H NMR (300 MHz, CDCl$_3$) δ 7.43 (m, 5H); 7.35 (s, 1H); 7.18 (t, J=6.5 Hz, 1H); 5.98 (d, J=6.8 Hz, 1H); 5.09 (s, 2H); 4.59 (m, 1H); 4.38 (m, 2H); 4.10 (br d, J=12 Hz, 2H); 3.81 (s, 3H); 3.73 (t, J=5.3 Hz, 2H); 2.71 (t, J=8.3 Hz, 2H); 1.72 (d, J=12.5 Hz, 2H); 1.53 (m, 2H); 1.42–1.37 (m, 1H); 1.35 (s, 9H); 1.10 (m, 2H).

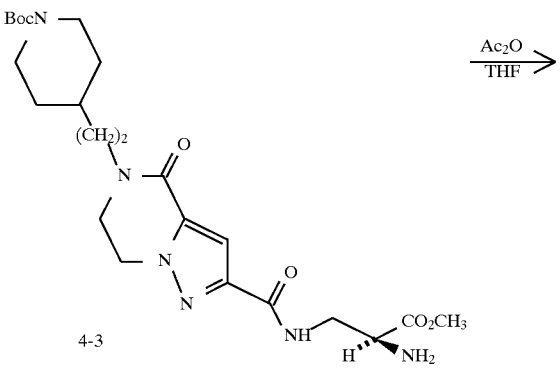

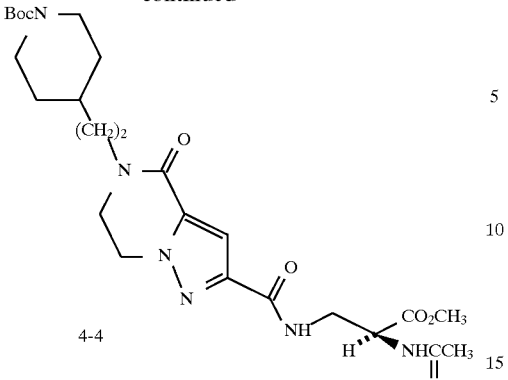

4-4

Methyl-2(S)-(Acetylamino)-3-[[[4,5,6,7-tetrahydro-4-oxo-5-[2-(N-Boc-piperidin-4-yl)ethyl]pyrazolo[1,5-a]pyrazin-2-yl]carbonyl]amino]-propionate (4-4)

Acetic anhydride (70 ml, 0.76 mmol), was added to a cooled (0°) solution of 4-3 (350 mg, 0.69 mmol) in 10 ml THF. The resulting solution was allowed to warm to room temperature and stirred for 18 h, then concentrated, and the residue was dissolved in 50 ml ethyl acetate and washed successively with $NaHCO_3$, $H_2O$, 10% $KHSO_4$, $H_2O$, and brine (25 ml each). The organic layer was dried over $Na_2SO_4$ and evaporated giving a colorless residue which was chromatographed on silica gel with 3% $CH_3OH/CH_2Cl_2$ to yield 4-4 as a white solid.

$^1$H NMR (CDCl$_3$) δ 7.29 (s, 1H) 7.24 (t, J=6.4 Hz, 1H); 6.81 (d, J=7.6 Hz, 1H); 4.79 (m, 1H); 4.38 (m, 2H); 4.10 (br d, J=12 Hz, 2H); 3.81 (s, 3H); 3.80 (m, 2H); 3.73 (t, J=5.3 Hz, 2H); 2.71 (t, J=8.3Hz, 2H); 2.01 (.s, 3H); 1.72 (d, J=12.5 Hz, 2H); 1.57 (m, 2H); 1.42–1.37 (m, 1H); 1.37 (s, 9H); 1.09 (m, 2H).

2-(S)-(Acetylamino)-3-[[[4,5,6,7-tetrahydro-4-oxo-5-[2-(piperidin-4-yl)ethyl]pyrazolo[1,5-a]pyrazin-2-yl]carbonyl]amino propionic acid (4-5)

A solution of 4-4 (203 mg, 0.38 mmol), 1 N LiOH (0.76 ml, 0.76 mmol), $H_2O$, $CH_3OH$, and THF (5 ml each) was stirred overnight at room temperature. The organic solvents were removed at reduced pressure and the remaining solution was diluted with 25 ml $H_2O$, made acidic with 10% $KHSO_4$, and extracted into ethyl acetate. The ethyl acetate was washed with $H_2O$ and brine, dried over $Na_2SO_4$, filtered and evaporated to provide the desired acid.

$^1$H NMR (CDCl$_3$) δ 7.93 (br, 1 H); 7.81 (br, 1 H); 7.29 (s, 1H); 4.79 (m, 1H); 4.348 (m, 2H); 4.10 (br d, J=12 Hz, 2H); 3.80 (br m, 2H); 3.73 (br, t, 2H); 2.71 (t, J=8.3Hz, 2H); 2.11 (s, 3H); 1.72 (d, J=12.5 Hz, 2H); 1.57 (m, 2H); 1.42–1.37 (m, 1H); 1.37 (s, 9H); 1.12 (m, 2H).

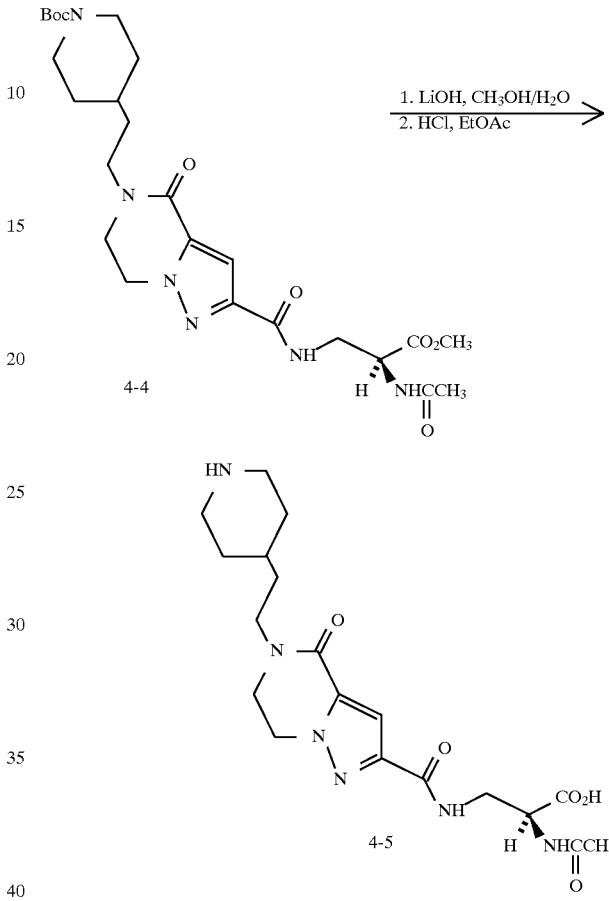

This acid (169 mg, 32.8 mmol) was dissolved in 50 ml ethyl acetate was cooled to 0° and treated with dry HCl for 30 min. The solvent was removed in vacuo and the residue triturated with anhydrous ether, filtered and dried over $P_2O_5$, to give 4-5 as a white solid, mp 150°–156°.

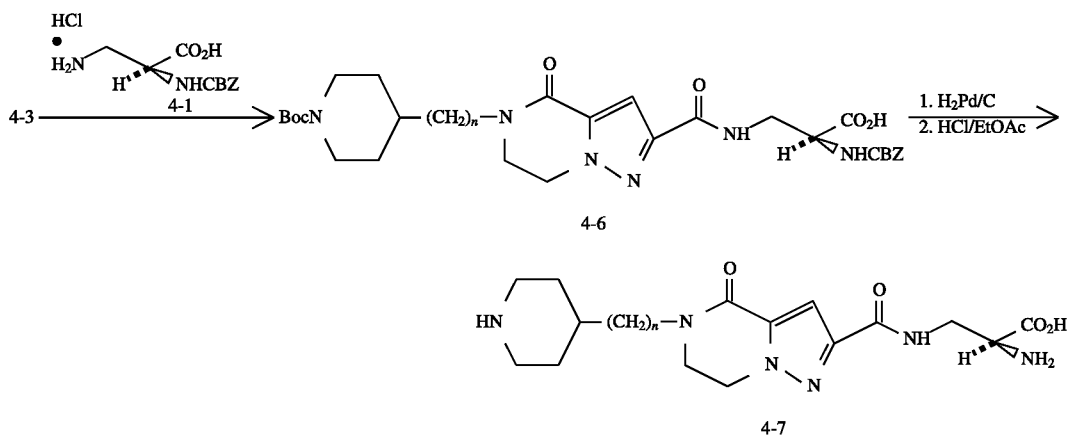

2(S)-[(Cbz-Amino)]-3-[[[4,5,6,7-tetrahydro-4-oxo-5-[2(N-Cbz-piperidin-4-yl)ethyl]pyrazolo[1,5-a]pyrazin-2-yl]carbonyl]amino propionic acid (4-6)

4-3 was coupled to Nα-CBZ-L-2,3-diamino-propionic acid (Fluka) (4-1) using the procedure described for 3-4 to provide 4-6, the doubly protected adduct.

2(S)-Amino-3-[[[4,5,6,7-tetrahydro-4-oxo-5-[2-(piperidin-4-yl)ethyl]pyrazolo[1,5-a]pyrazin-2-yl]carbonyl]amino propionic acid Treatment of 4-6 with $H_2$ in the presence of Pd/C gave the desired acid, mp. 157°. The Boc group was then removed with HCl/EtOAc in standard fashion to give pure 4-7, mp. 195°–198°.

A solution of 4-3 (0.30 g, 0.61 mmol), n-butyl sulfonyl chloride (0.16 g, 0.91 mmol), and N-methyl morpholine in 50 ml of THF was stirred at room temperature for 12 h. The solvent was evaporated at reduced pressure and the resulting oil was dissolved in $CH_2Cl_2$ (50 ml) washed with 10% $KHSO_3$ (50 ml) then dried over $Na_2SO_4$, filtered and evaporated. The resulting residue was chromatographed on silica gel giving 4-8 as a colorless glass.

$^1$H NMR (CDCl$_3$) δ 8.31 (t, J=6Hz, 1H); 7.62 (d, J=8.5 Hz, 1H); 7.01 (s, 1H); 4.43 (t, J=6.6 Hz, 2H); 4.11 (m, 1H); 3.92 (d, J=12 Hz, 2H); 3.83 (s, 3H); 3.80 (t, J=6.6 Hz, 2H);

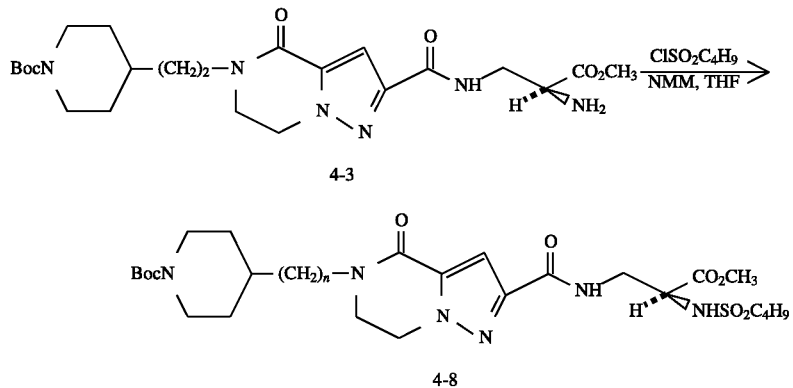

Methyl 2(S)-[(n-Butylsulfonylamino)]-3-[[[4,5,6,7-tetrahydro-4-oxo-5-[2-(N-CBZ-piperidin-4-yl)ethyl]pyrazolo[1,5-a]pyrazin-2-yl]carbonyl]-aminopropionate (4-8)

3.51 (t, J=7.3 Hz, 2H); 3.65 (m, 2H); 3.51 (t, J=6.8 Hz, 2H); 2.96 (t, J=7.2 Hz, 2H); 1.70 (d, J=11 Hz, 2H); 1.53 (m, 2H); 1.60–1.49 (overlapping m, 5H); 1.40 (s, 9H); 1.28 (q, J=7.1 Hz, 2H); 1.05 (m, 2H); 0.79 (t, J=7.1 Hz, 3H).

SCHEME 5

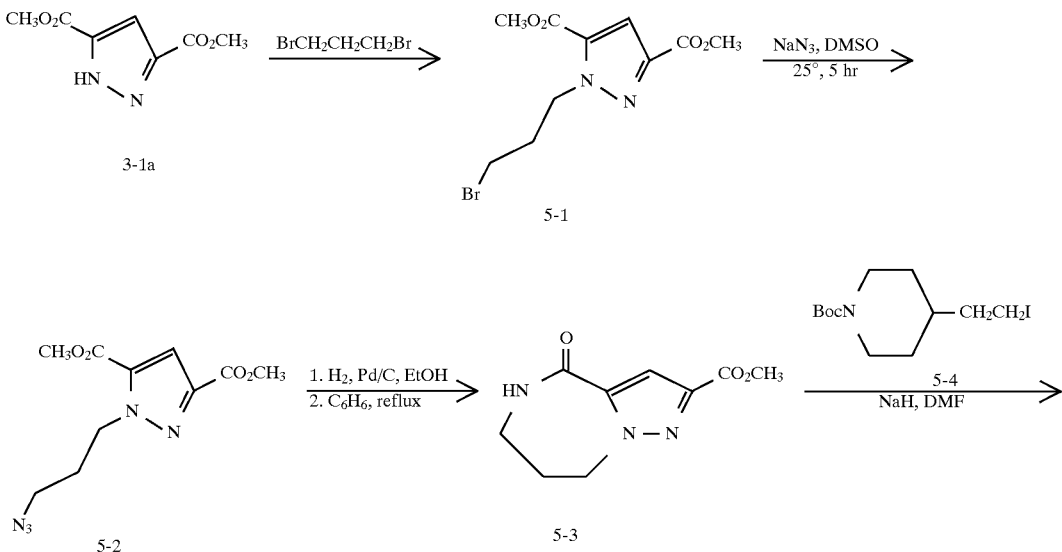

SCHEME 5 -continued

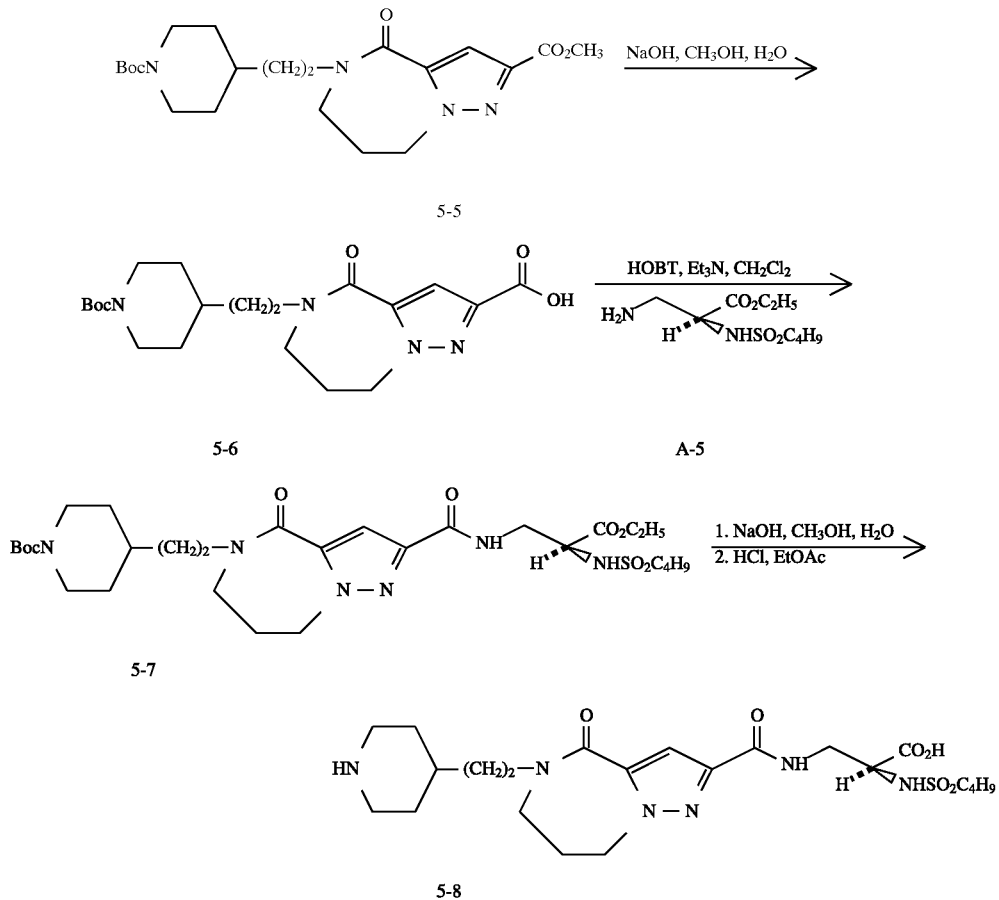

Dimethyl 1-(3-Bromopropyl)pyrazole-3,5-dicarboxylate (5-1)

Compound 5-1 was obtained as a white crystalline solid using 1,3-dibromopropane in the procedure described for 3-2.

$^1$H NMR (CDCl$_3$) δ 7.38 (s, 1H); 4.95 (t, J=8.2Hz, 2H); 3.95 (s, 3H); 3.92 (s, 3H); 3.75 (t, J=8.5 Hz, 2H) 2.51 (m, 2H).

Dimethyl 1-(3-Azidopropyl)pyrazole-3,5-dicarboxylate (5-2)

A solution of 5-1 (1.0 g, 3.45 mmol) in 10 ml DMSO was treated with NaN$_3$ (0.883 g, 13.8 mmol) and mixture stirred at 25° C. for 5 h. Next, the reaction mixture was diluted with 100 ml of H$_2$O and then extracted with ethyl acetate (3×100 ml). The combined organic extracts were washed with water (2×100 ml) and brine (1×100 ml), dried over Na$_2$SO$_4$ and evaporated to give 5-2 as a colorless oil.

Methyl-5,6,7,8-tetrahydro-4-oxo-4H-pyrazolo[1,5-a][1,4]diazepin-2-yl]-carboxylate (5-3)

A solution of 5-2 (851 mg, 3.25 mmol) in 100 ml absolute EtOH was treated with 100 mg 10% Pd on C and the mixture was shaken on a Parr hydrogenator at 45 Psi for 5 h. The catalyst was removed by filtration through celite and the filtrate was evaporated to give 800 mg of a colorless oil. NMR analysis showed this material to a mixture of 1-(3-aminopropyl) Dimethylpyrazole-3,5-dicarboxylate and the cyclic diazapineone. This mixture was dissolved in 50 ml of benzene and refluxed for 15 h then evaporated. The resulting tan solid was recrystalized from CH$_2$Cl$_2$/hexane to afford 5-3 as a white solid.

m.p.=220°–221° C. $^1$H NMR (CDCl$_3$) δ 7.36 (s,1H); 6.42 (br t, 1H); 4.58 (t, J=8.0 Hz, 2H); 3.95 (s, 3H); 3.39 (dt, J=7.2 Hz, 2H); 2.31 (m, 2H).

Methyl-5,6,7,8-tetrahydro-4-oxo-5-[2-(N-Boc-piperidin-4-yl)ethyl]-4H-pyrazolo[1,5-a][1,4]diazepin-2-yl]carboxylate (5-5)

To a solution of 5-3 (175 mg, 0.83 mmol), in 50 ml DMF was, added 60% NaH (36 mg, 0.91 mmol), the mixture was stirred under N$_2$ at −15° for 30 min. To this mixture a solution of 2-(N-Boc-Piperidin-4-yl)ethyl iodide (5-4) (283 mg, 083 mmol) in 25 ml DMF was added dropwise over 20 min. The resulting solution was stirred for 30 min at −15° then warmed to room temperature and allowed to stir overnight. The DMF was evaporated at reduced pressure and the residue redissolved in ethyl acetate, filtered and chromatographed on silica gel using ethyl acetate as eluent to afford pure 5-5 as a glass.

$^1$H NMR (CDCl$_3$) δ 7.24 (s, 1H); 4.50 (t, J=7.0 Hz, 2H); 3.93 (br d, J=12 Hz, 2H); 3.94 (s, 3H); 3.61 (t, J=5.3 Hz, 2H); 3.42 (t, J=7.3 Hz, 2H); 2.7 (br t, J=6.3 Hz, 2H); 2.3 (m, 2H); 1.55 (d, J=12.5 Hz, 2H); 1.38 (m, 2H); 1.33–1.25 (m, 1H); 1.27 (s, 9H); 1.01 (m, 2H).

5,6,7,8-Tetrahydro-4-oxo-5-[2-(N-Boc-piperidin-4-yl)ethyl-4H-pyrazolo[1,5-a][1,4]diazepin-2-yl]-carboxylic acid (5-6)

A solution of 5-5 (166 mg, 0.395 mmol) in 10 ml CH$_3$OH, was treated with 1N NaOH (0.435 ml, 0.43 mmol). The resulting solution was stirred at room temperature for 18 h and then CH$_3$OH removed at reduced pressure. The remaining aqueous phase was acidified with 10% aqueous citric acid and extracted with CH₂Cl₂ (2×50 ml). The pooled organic extracts were dried over Na₂SO₄ then concentrated to give 5-6 as a white solid.

¹H NMR (CDCl₃) δ 7.29 (s, 1H); 4.52 (t, J=7.0 Hz, 2H); 4.12 (br d, J=12 Hz, 2H); 3.94 (s, 3H); 3.61 (t, J=5.3 Hz, 2H); 3.42 (t, J=7.3 Hz, 2H); 2.7 (br t, J=6.3 Hz, 2H); 2.3 (m, 2H); 1.55 (d, J=12.5 Hz, 2H); 1.38 (m, 2H); 1.33–1.25 (m, 1H); 1.27 (s, 9H); 1.01 (m, 2H).

Ethyl-2(S)-[(n-Butylsulfonyl)amino]-3-[[[5,6,7,8-tetrahydro-4-oxo-5-[2-(N-Boc-piperidin-4-yl)ethyl]-4H-pyrazolo[1,5-a][1,4]-diazepin-2-yl]carbonyl]amino propionate (5-7)

5-6 (147 mg, 0.36 mmol) in CH₂Cl₂/5 ml was treated with ethyl 2(S)-n-butanesulfonamido-3-amino-propionate (A-5) (115 mg, 0.40 mmol), HOBT (49 mg, 0.36 mmol), and Et₃N (0.10 ml, 0.724 mmol) in 50 ml CH₂Cl₂ and this solution was stirred under N₂ for 18 h at room temperature. The reaction solution was washed successively with sat. NaHCO₃, H₂O, 10% citric acid, H₂O and brine (1×20 ml each), dried over Na₂SO₄, filtered and evaporated. The resulting clear glass was chromatographed on silica gel using 5% CH₃OH/EtOAc as eluent giving pure 5-7.

¹H NMR (CDCl₃) δ 7.32 (s, 1H); 7.24 (t, J=6.8 Hz, 1H); 5.54 (t, J=7.2 Hz, 1H; 4.43(t J=7.8 Hz, 2H); 4.32 (m, 1H); 4.28 (q, J=7.1 Hz, 2H); 4.10 (br d, J=12 Hz, 2H); 3.85 (m, 2H); 3.61 (t, J=5.3 Hz, 2H); 3.42 (t, J=7.3 Hz, 2H); 3.03 (t, J=7.1 Hz, 2H); 2.7 (br t, J=6.3 Hz, 2H); 2.3 (m, 2H); 1.65–1.45 (overlapping m, 7H); 1.38 (m, 2H); 1.33–1.25 (m, 1H); 1.37 (s, 9H); 1.30 (t, J=7.4 Hz, 3H); 1.01 (m, 2H); 0.96 (t, J=7.3 Hz, 3H).

2(S)-[(n-Butylsulfonyl)amino]-3-[[[5,6,7,8-tetrahydro-4-oxo-5-[2-(piperidin-4-yl)ethyl]-4H-pyrazolo[1,5-a][1,4] diazepin-2-carbonyl]-amino propionic acid (5-8)

To a solution of 5-7 (100 mg, 0.156 mmol) in 10 ml CH₃OH, was added 1N NaOH (160 ml, 0.16 mmol) and H₂O, 10 ml. The resulting solution was stirred at room temperature for 3.5 h then CH₃OH removed at reduced pressure. The remaining aqueous phase was acidified with 10% aqueous citric acid and extracted with CH₂Cl₂ (2×50 ml). The pooled organic extracts were dried over Na₂SO₄ then evaporated to give the desired acid.

¹H NMR (CDCl₃) δ 17.24 (t, J=6.8 Hz,1H); 7.28 (s, 1H); 6.0 (d, J=7.2 Hz, 1H); 4.43 (t, J=7.8 Hz, 2H); 4.32 (m, 1H); 4.10 (br d, J=12 Hz, 2H); 3.85 (m, 2H); 3.61 (t, J=5.3 Hz, 2H); 3.42 (t, J=7.3 Hz, 2H); 3.03 (t, J=7.1 Hz, 2H); 2.7 (br t, J=6.3 Hz, 2H); 2.3 (m, 2H); 1.65–1.45 (overlapping m, 7H); 1.38 (m, 2H); 1.33–1.25 (m, 1H); 1.37 (s, 9H); 1.01 (m, 2H); 0.96 (t, J=7.3 Hz, 3H).

This acid (89 mg) in 15 ml ethyl acetate was cooled to 0° and HCl; gas bubbled through for 3 min. The reaction mixture was warmed to room temperature, stirred for 30 min then taken to dryness on a rotary evaporator. The remaining white solid was triturated with ether, filtered and vacuum dried over P₂O₅ to give 5-8 as a white solid.

¹H NMR (DMSO-d₆) δ 8.95 (br s, 1H); 8.33 (t, J=5.7 Hz, 1H); 7.64 (d, J=9 Hz, 1H); 7.02 (s, 1H); 4.35 (t, J=5.1 Hz, 2H); 4.10 (m, 1H); 3.81 (t, J=5.2 Hz, 2H); 3.6–3.4 (m, 4H); 3.21 (d, J=10.5 Hz, 2H); 2.95 (t, J=7.8 Hz, 2H); 2.81 (br m, 2H); 1.96 (d, J=11Hz, 2H); 1.62–1.2 (overlapping multiplets, 9H); 0.80 (t, J=7.3Hz, 2H).

SCHEME 6

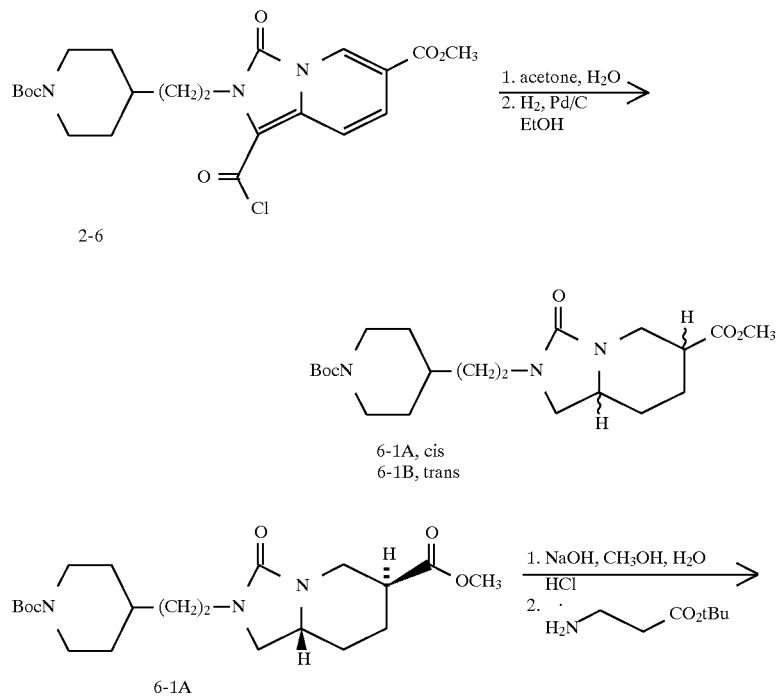

SCHEME 6 -continued

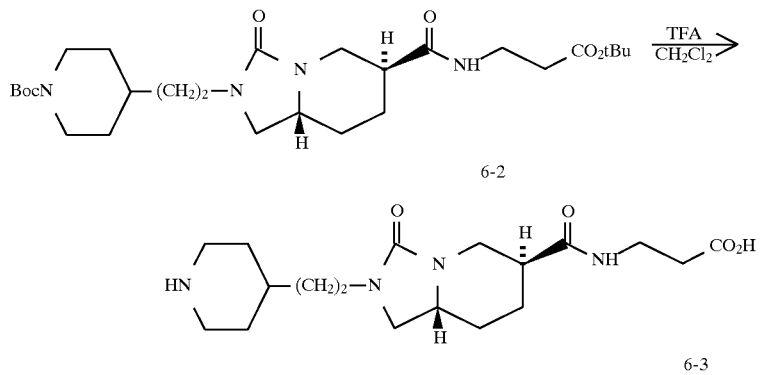

Ethyl-3-oxo-2[2-(N-Boc-piperidin-4-yl)ethyl]octahydroimidazo-1,5-a]pyridin-6-yl]carboxylate (6-1A, 6-1B)

2-6, (514 mg, 1.1 mmol) was dissolved in 25 ml of acetone 10 ml of $H_2O$ was added and the mixture heated to 60° C. for 3.5 h. The acetone was removed at reduced pressure and the resulting yellow precipitate filtered. This crude material was dissolved in 100 ml of toluene and refluxed for 3 h. The toluene was evaporated giving a yellow solid.

This solid (500 mg, 1.11 mmol) was dissolved in 100 ml of ethanol 75 mg of 10% Pd on C was added and mixture shaken on Parr hydrogenator at 55 psi for 13 h. The catalyst was removed by filtration through celite and the solvent evaporated. The resulting colorless oil was chromatographed on silica gel using 70% ethyl acetate/30% hexane to give 268 mg of the cis reduction product 6-1 A along with 132 mg of the trans product 6-1B.

Isomer 6-1A $^1$H NMR (CDCl$_3$) δ 4.15 (m, 1H); 4.06 (m, 2H); 3.68 (s, 3H); 3.41 (m, 2H); 3.22 (m, 1H); 2.90 (m, 1H); 2.80 (m, 2H); 2.68 (m, 2H); 2.43 (m, 1H); 2.16 (m, 1H); 1.81 (m, 1H); 1.69 (m, 2H); 1.60 (m, 1H); 1.45 (s, 9H); 1.43 (m, 3H); 1.39 (m, 1H); 1.11 (m, 2H).

Isomer 6-1B $^1$H NMR (CDCl$_3$) δ 4.34 (m, 1H); 4.06 (m, 2H); 3.69 (s, 3H); 3.40 (m, 3H); 3.36 (m, 1H); 3.30 (m, 1H); 3.11 (m, 1H); 2.89 (m, 1H); 2.84 (m, 1H); 2.67 (m, 2H); 2.63 (m, 1H); 2.30 (m, 1H); 1.69 (m, 2H); 1.67 (m, 2H); 1.60 (m, 1H); 1.45 (s, 9H); 1.41 (m, 1H); 1.09 (m, 2H).

tert-Butyl (±)-cis-[[3-oxo-2[2(N-Boc-piperidin-4-yl)ethyl]octahydroimidazo[1,5-a]pyridin-6-yl]carbonyl]amino]propionate (6-2)

6-1A was hydrolyzed with 1N NaOH in $CH_3OH/H_2O$ as described for 1-6 to give the desired acid. This acid was coupled with β-alanine t-butyl ester as described for 2-8 to provide 6-2.

$^1$H NMR (CDCl$_3$) δ 6.32 (t, 1H); 4.06 (m, 2H); 3.98 (m, 1H); 3.56 (m, 5H); 3.21 (m, 2H); 2.91 (m, 1H); 2.92 (m, 1H); 2.80 (m, 2H); 2.40 (t, 2H); 2.23 (m, 1H); 2.09 (m, 1H); 1.81 (m, 3H); 1.69 (m, 2H); 1.60 (m, 1H); 1.45 (s, 18H); 1.43 (m, 3H); 1.11 (m, 2H).

(±)cis-3-Oxo-2[2-(piperidin-4-yl)ethyl]octahydroimidazo[1,5-a]pyridin-6-yl]carbonyl]aminopropionic acid (6-3)

6-2 (65.3 mg, 0.13 mmol) was dissolved in 10 ml of anhydrous $CH_2Cl_2$ and cooled to 0° C. Trifluoroacetic acid (0.200 ml) was added and solution stirred for 1 h then evaporated at reduced pressure to give pure 6-3.

$^1$H NMR (CD$_3$OD) δ 4.06 (m, 2H); 3.91 (m, 1H); 3.56 (m, 5H); 3.21 (m, 2H); 2.91 (m, 1H); 2.92 (m, 1H); 2.80 (m, 2H); 2.40 (t, 2H); 2.23 (m, 1H); 2.09 (m, 1H); 1.81 (m, 3H); 1.68 (m, 2H); 1.60 (m, 1H); 1.28 (m, 3H); 0.91 (m, 2H).

SCHEME 7

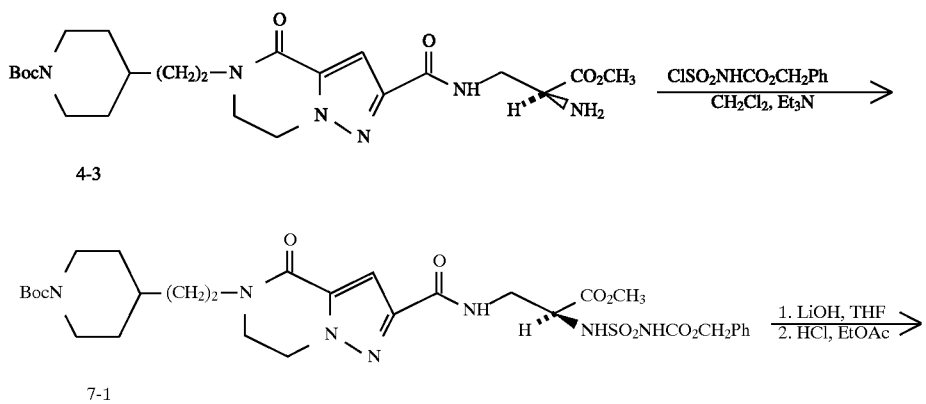

SCHEME 7 -continued

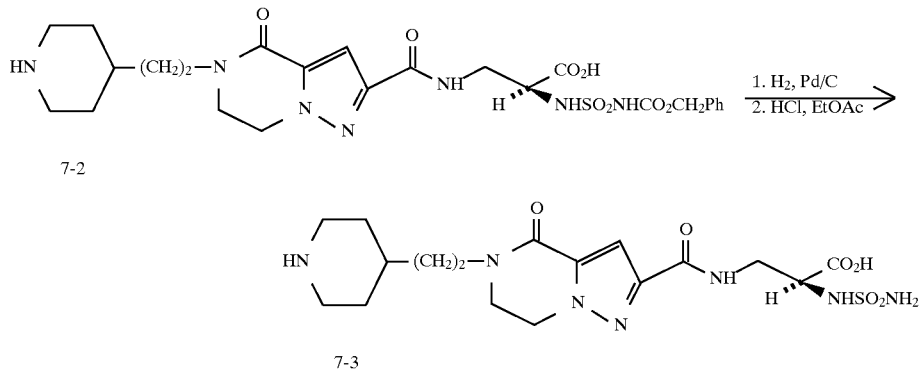

Methyl-2(S)-[(N-CBZ-Aminosulfonyl)amino]-3-[[[4,5,6,7-tetrahydro-4-oxo-5-[2(N-BOC-piperidin-4-yl)ethyl]pyrazolo[1,5-a]pyrizine-2-yl]carbonyl]amino]propionate (7-1)

To a 0° solution of chlorosulfamylisocyanate (45.1 μl, 0.508 mmol) in methylene chloride was added benzyl alcohol (53 ml, 0.508 mmol). The reaction was aged 90 min at 0° and a solution of 4-3 (250 mg., 0.508 mmol) in methylene chloride containing triethylamine (142 ml, 1.02 mmol) added. The reaction was allowed to warm to room temperature and stirred overnight (18 hr). The reaction was adjusted to a pH=3.0 with aqueous sodium bisulfate and the product was extracted with methylene chloride(3×10 ml). The organic extracts were combined, concentrated and chromatographed on silica (eluent 95% methylene chloride, 5% methanol) to give 7-1.

$^1$H NMR (300 MHz, CDCl$_3$) δ 1.40 (s, 9H), 2.65 (t, 2H), 3.65 (s, 3H), 5.10 (s, 2H), 6.65 (d, 1H), 7.2–7.5 (m, 6H), 8.90 (s, 1H)

2(S)-[(N-CBZ-Aminosulfonyl)amino]-3-[[[4,5,6,7-tetrahydro-4-oxo-5-[2-(N-Boc-piperidin-4-yl)ethyl)pyrazolo[1,5-a]pyrazine-2-yl]carboxyl]-amino propionic acid (7-2)

To a solution of 7-1 (100 mg) in THF (5 ml) was added 1N LiOH (0.6 ml) and the mixture stirred at room temperature for 18 h. The reaction was quenched by addition of aq. sodium bisulfate (pH=3.0) and product extracted into ethyl acetate (2×15 ml). Concentration of the extracts gave the desired acid.

$^1$NMR 1.4 (s, 9H), 2.6 (br, t, 2H), 7.1–7.2 (br.m, 5H), 7.3 (s, 1H).

This acid was dissolved in EtOAc, cooled to −5°, and treated with HCl (gas). The reaction mixture was concentrated and flushed with ethyl acetate to give 7-2, mp >200° (dec.)

CHN analysis Calc. C, 44.86; H, 5.92; N, 14.20

Found: C, 44.50, H, 6.09; N, 13.80

2(S)-(Aminosulfonyl)amino-3-[[[4,5,6,7-tetrahydro-4-oxo-5-[2-(piperidin-4-yl)ethyl]pyrazolo[1,5-a]Pyrazin-2-yl]carbonyl]amino-propionic acid (7-3)

A solution of 7-2 (70 mg) in methanol (20 ml) was treated with 10%Pd/C (35 mg) and the mixture hydrogenated (1 atm.) overnight (18 hrs). The mixture was filtered and concentrated to give 46 mg of an oil. The oil was dissolved in ethyl acetate, cooled to 0° and HCl gas bubbled in over 30 min. Concentration of the reaction gave 7-3 as a white solid, mp >200°, FAB MS, M+1=458.

SCHEME 8

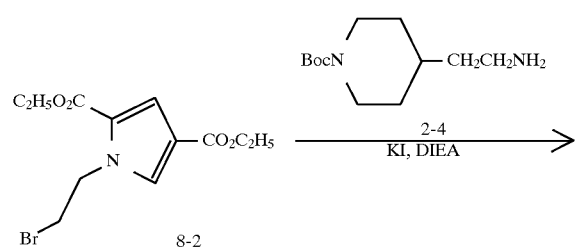

SCHEME 8 -continued

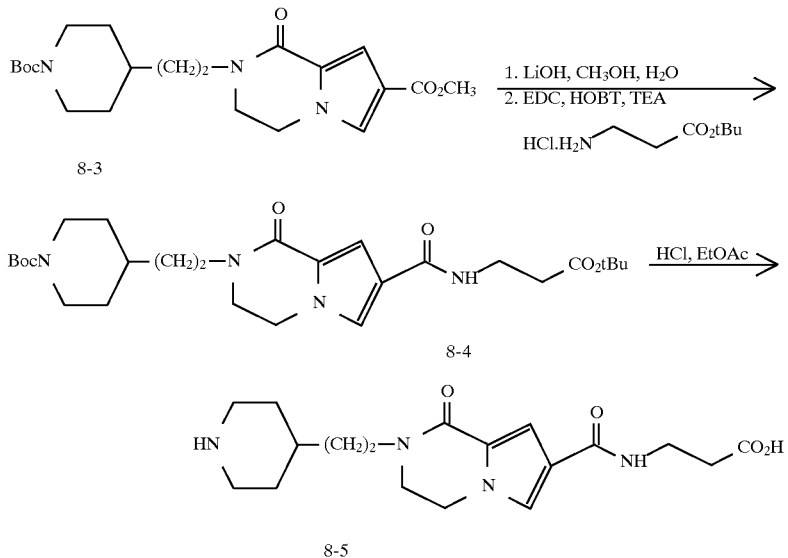

Diethyl 1-(2-Bromoethyl)pyrrole-2,4-dicarboxylate (8-2)

A solution of diethyl pyrrole-2,4-dicarboxylate (5.50 g, 29.4 mmol) in tetrahydrofuran (200 ml) was cooled in an ice bath and a suspension of NaH (60%) (6.5 g, 68.6 mmol) in tetrahydro-furan (50 ml) was added in a stream. The reaction flask was warmed to room temperature. After stirring 1 h at room temperature 1,2-dibromoethane (25.2 ml, 294 mmol) was added and the mixture was refluxed for 24 h. Water (50 ml) was added to the reaction flask. The mixture was rotary evaporated to remove tetrahydrofuran. Saturated sodium bicarbonate solution (100 ml) was added to the residue and the resulting solution was extracted with methylene chloride (4×50 ml). The combined organic extracts were dried with anhydrous sodium sulfate. The drying agent was removed by filtration, and the filtrate was rotary evaporated to give a yellow solid. This material was recrystalized from hexane ethyl acetate 80:20 to give 8-2 as a yellow solid.

$^1$H NMR (DMSO-$d_6$) δ 7.83 (d, 1H); 7.15 (d, 1H); 4.69 (t, 2H); 4.25 (m, 4H); 3.78 (t, 2H); 3.31 (H$_2$O); 1.29–1.22 (m, 6H).

Ethyl [4,5,6,7]-Tetrahydro-4-oxo-5-[2-(N-Boc-Piperidin-4-yl)ethyl]-pyrrolo[1,5-a]pyrazin-2-yl]carboxylate (8-3)

The alkyl bromide 8-2 (3.30 g, 10.4 mmol., 1.0 eq.), 2-4 (3.52 g, 15.5 mmol., 1.5 eq.), potassium iodide (5.18 g, 31.2 mmol), diisopropylethylamine (5.42 ml, 31.2 mmol., 3.0 eq.), and acetonitrile (50 ml) were combined. The suspension was heated to reflux for 24 h, and then rotary evaporated to remove acetonitrile. Saturated sodium bicarbonate solution (100 ml) was added, and the solution was extracted with ethyl acetate (5×50 ml). The combined organic extracts were dried with anhydrous sodium sulfate and concentrated to a brown oil. The crude product was subjected to column chromatography using silica. The column was eluted with methylene chloride then methylene chloride containing 1 % methanol to give pure 8-3 as a white solid.

$^1$H NMR (CDCl$_3$) δ 7.32 (d, 1H); 7.29 (d, 1H); 4.28 (q, 2H); 4.19–4.00 (m, 4H); 3.7–3.6 (t, 2H); 3.6–3.5 (t, 2H); 2.68 (t, 2H); 1.8–1.7 (m, br, 2H, H$_2$O); 1.6–1.4 (s, m, 1H); 1.33 (t, 3H); 1.2–1.1 (m, 2H).

tert-Butyl [4,5,6,7]-tetrahydro-4-oxo-5[2-(N-Boc-piperidin-4-yl)ethyl]pyrrolo[1,5-a]pyrazin-2-yl]amino propionate (8-4)

8-3 (620 mg, 1.54 mmol) lithium hydroxide monohydrate (160 mg, 4.00 mmol., 2.6 eq.), water (15 ml), and methanol (10 ml) were combined in a 50 ml round bottom flask equipped with a magnetic stir bar. The solution was stirred for 4 h at room temperature then heated to 90° for 1 h. Any remaining methanol was removed by rotary evaporation and the aqueous residue was acidified with 10% K$_2$SO$_4$ then extracted with ethyl acetate (4×50 ml). The combined organic extracts were dried with anhydrous sodium sulfate, filtered, and evaporated giving the desired acid as a white solid.

$^1$H NMR (DMSO-$d_6$) δ 7.51 (d, 2H); 6.84 (d, 1H); 4.19 (m, 2H); 3.90 (d, br, 2H); 3.63 (m, 2H); 3.43 (m, 2H); 3.4–3.2 (H$_2$O); 2.6–2.8 (br, 2H); 1.66 (d, 2H); 1.43 (m, 2H); 1.36 (s, 9H); 1.1–0.9 (m, 2H).

This acid (150 mg, 554 mmol), EDC (117 mg, 0.609 mmol), 1-hydroxybenzotriazole (82.2 mg, 0.609 mmol), triethylamine (0.300 ml, 1.11 mmol., 4.0 eq.), β-alanine-t-butyl ester (111 mg, 0.609 mmol), and methylene chloride (10 ml) were combined in a 100 ml round bottom flask equipped with a magnetic stir bar. The resulting solution was stirred at room temperature overnight. Solvent was rotary evaporated from the reaction flask and the resulting residue was subjected to column chromatography using silica. The column was eluted with methylene chloride, methylene chloride with 2% methanol then 4% methanol. Fractions containing product were pooled to provide 8-4 as a white solid.

$^1$H NMR (CDCl$_3$) δ 7.32 (d, 1H); 7.04 (d, 1H); 6.58 (m, 1H); 4.2–4.0 (m, 4H); 3.7–3.5 (m, 6H); 2.68 (t, 2H); 2.51 (t, 2H); 1.70 (m, 3H, H$_2$O); 1.53 (m, 2H); 1.45 (s, 9H); 1.21–1.0 (m, 2H).

4,5,6,7-Tetrahydro-4-oxo-5-[2-(piperidin-4-yl)ethyl][1,5-a]pyrazine-2-yl]carbonyl]amino propionic acid (8-5)

The ester 8-4 (180 mg, 0.347 mmol) and ethyl acetate (10 ml) were combined in a 50 ml round bottom flask. The suspension was cooled in an ice bath. Hydrogen chloride was bubbled through the suspension for 1.5 min. The reaction flask was warmed to room temperature, then solvent was removed by vacuum filtration giving 8-5 as a white solid, mp 248°–249°.

$^1$H NMR (DMSO-$d_6$) δ 9.0–8.5 (br, 2H); 8.05 (m, 1H); 7.42 (d, 1H); 7.05 (d, 1H); 4.15 (m, 2H); 3.62 (m, 2H); 3.5–3.3 (m, 4H, H$_2$O); 3.25–3.15 (d, br, 2H); 2.85–2.7 (br, 2H); 2.5–2.4 (m, 4H); 1.81 (d, 2H); 1.6–1.4 (m, 3H); 1.4–1.2 (m, 2H).

SCHEME 9

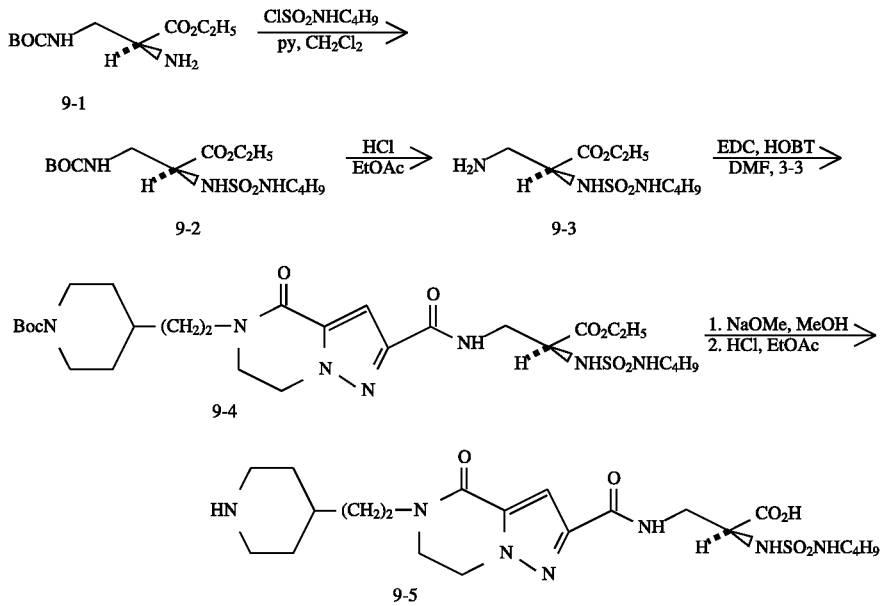

Ethyl 2(S)-Amino-3-(N-Boc-amino)propionate (9-1)

Commerically available 2(S)-3-diaminopropanoic acid (Fluka) (10 g, 96.2 mmol) was dissolved in absolute ethanol (200 ml) and the solution was saturated with anhydrous HCl gas then heated at reflux for 2.5 h. The solvent was removed and the residue recrystallized from EtOH/Et$_2$O to afford the ethyl/ester dihydrochloride as a hygroscopic white solid.

This material (5 g, 24.3 mmol) was suspended in CH$_2$Cl$_2$ (200 ml) cooled to −50°. Next, triethylamine (7.0 ml, 51 mmol) was added and the mixture stirred for 5 min. A solution of di-tert-butyl dicarbonate (5.30 g, 24.3 mmol) in 100 ml CH$_2$Cl$_2$ was added dropwise over a 30 min period and the mixture stirred at −50° for 1.5 h, then warmed to room temperature. The solution was washed with water (2×100 ml), then dried (Na$_2$SO$_4$) and evaporated. The resulting residue was chromatographed silica gel (80:20 CH$_2$Cl$_2$/CH$_3$OH) to afford pure 9-1.

$^1$H NMR (300 MHz, CDCl$_3$) 6.03 (brt, 1H); 4.35 (m, 1H); 3.85 (m, 2H); 3.23 (m, 2H); 1.21 (t, 3H).

Ethyl 2(S)-n-Butylaminosulfonylamino-3-(N-BOC-amino)propionate (9-2)

A solution of 9-1 (500 mg, 2.15 mmol) in CH$_2$Cl$_2$ (10 ml) was treated with pyridine (261 ml, 3.23 mmol) and n-butylsulfoamoyl chloride (406 mg, 2.37 mmol). The solution was stirred at room temperature for 3 h, then poured onto silica gel and eluted with 30% acetone/hexane to give pure 9-2 as a white solid.

$^1$H NMR (300 MHz, CDCl$_3$) δ 5.43 (d, 1H); 4.98 (t, 1H); 4.40 (brs, 1H); 4.10 (q, 2H); 4.05 (m, 1H); 3.56 (m, 2H); 3.08 (m, 2H); 1.8–1.2 (overlaping multipets, 16H); 0.90 (t, 3H).

Ethyl 2(S)-(n-Butylaminosulfonylamino)-3-aminopropionate (9-3)

A solution of 9-2 (612 mg, 1.65 mmol) in ethyl acetate (50 ml) was cooled to −5° and anhydrous HCl was bubbled in for 30 min. The reaction was concentrated and the product isolated by filtration to give 9-3 as a white solid.

$^1$H NMR (300 MHz, DMSO-d$_6$) δ 5.82 (d, 1H); 4.56 (brs, 1H); 4.20 (q, 2H); 4.02 (m, 1H); 3.45 (m, 2H); 3.01 (m, 2H); 1.9–1.36 (m, 7H); 0.93 (t, 3H).

Ethyl 2(S)-[(n-Butylaminosulfonyl)amino]-3-[[4,5,6,7-tetrahydro-4-oxo-5-[2-(piperidin-4-yl)ethyl]pyrazolo[1,5-a]pyrazin-2-yl]carbonyl]amine propionate (9-4)

Coupling or 9-3 with 3-3 with EDC and HOBT in DMF as described for 1-6 provided 9-4.

$^1$H NMR (300 MHz, CDCl$_3$) δ 7.29 (s, 1H); 7.19 (t, 1H); 5.43 (d, 1H); 4.41 (t, 2H); 4.26 (q, 2H); 4.20 (m, 1H); 4.08 (d, 2H); 3.86 (m, 2H); 3.76 (m, 2H); 3.60 (t, 2H); 3.08 (t, 2H); 2.68 (t, 2H); 1.78 (d, 2H); 1.6–1.08 (m, 8H); 1.43 (s, 9H); 0.92 (t, 3H).

2(S)-[(n-Butylaminosulfonylamino]-3-[(4,5,6,7-tetrahydro-4-oxo-5-(piperidin-4-yl)ethyl)pyrazolo[1,5-a]pyrazin-2-yl]carbonyl]-aminopropionic acid (9-5)

Hydrolysis of 9-4 with NaOMe, isolation of the crude acid, and subsequent treatment with HCl in EtOAc as described for 5-7 provided 9-5 as a white solid, mp. 155°–160°.

SCHEME 10

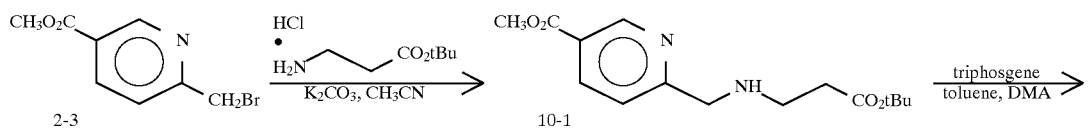

-continued
SCHEME 10

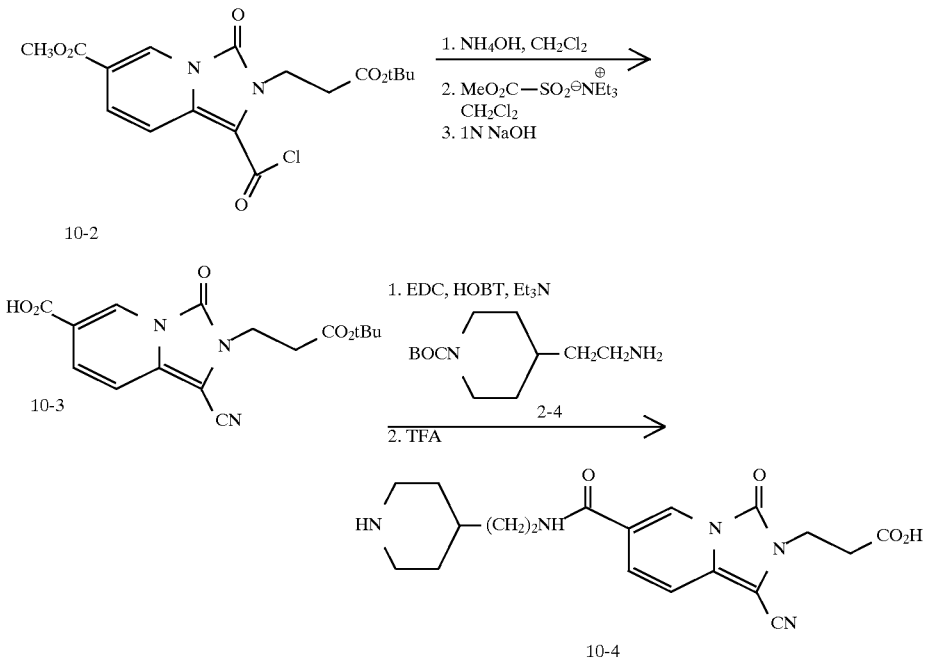

N-[2-(5-Carbomethoxy)pyridylmethyl]-β-alanine tert-butyl ester (10-1)

A mixture of 2-3 (871 mg, 3.79 mmol), β-alanine tert-butyl ester·HCl (2.7 g, 15 mmol), and K$_2$CO$_3$ (4.5 g, 30 mmol) in 100 ml of anhydrous CH$_3$CN was placed in a 250 ml flask and refluxed for 3 h, then cooled and filtered. The filtrate was concentrated at reduced pressure and chromatographed on silica gel using EtOAc as eluent to afford 10-1 as a colorless glass.

$^1$H NMR (CDCl$_3$) δ 9.18 (d, J=1.4Hz, 1H); 8.1(dd, J=1.4 and 6.8 Hz, 1H); 7.39 (d, J=6.8 Hz, 1H); 4.08 (s, 2 H); 3.95 (s, 3H); 3.04 (t, 2H); 2.60 (t, 2H); 1.4 (s, 9H).

tert-Butyl-2-(2-carboxyethyl)-1-chlorocarbonyl-3-oxo-2,3-dihydroimidazo[1,5-a]pyridine-6-carboxylate (10-2)

10-1 (800 mg, 2.71 mmol) was dissolved in 50 ml of toluene. N,N-dimethyl aniline (2.0 ml, 16.7 mmol) was added an solution cooled to 0°. To this, a solution of triphosgene (1.7 g, 5.7 mmol) in 15 ml toluene was added dropwise over 30 min. The solution was then warmed to 25° and stirred for 3.0 h then washed twice with 1N HCl, water and brine (50 ml of each), dried over Na$_2$SO$_4$ and evaporated giving 10-2 as a yellow crystalline solid.

$^1$H NMR (CDCl$_3$) δ 8.83 (d, J=1.4Hz, 1H); 8.25 (d, J=6.8 Hz, 1H); 7.82 (dd, J=1.4 and 6.8 Hz,1H); 4.43 (t, J=7.2 Hz, 2H); 3.98 (s, 3 H); 2.75 (t, J=7.2 Hz, 2H); 1.4 (s, 9H).

tert-Butyl-2-(2-carboxyethyl)-1-cyano-3-oxo-2,3-dihydroimidazo-[1,5-a]pyridine-6-carboxylate (10-3)

10-2 (250 mg, 0.65 mmol) was dissolved in 100 ml of CH$_2$Cl$_2$ 10 ml of ammonium hydroxide was added and this biphasic mixture was stirred for 1 h then the organic layer separated and washed with 10% citric acid then brine (50 ml), dried over Na$_2$SO$_4$ and evaporated.

This residue (150 mg, 0.42 mmol) was dissolved in 100 ml of CH$_2$Cl$_2$, 355.7 mg of Methoxycarbonylsulfamoyl-triethylammonium hydroxide, inner salt (Burgess reagent, 1.48 mmol) was added in three portions over a 2 h period. The resulting solution was stirred at room temperature for an additional hour and then concentrated and chromatographed on silica gel using 1:1 hexane/ethyl acetate as eluent giving the nitrile in quantitative yield. This material was subjected to saponification using 1N LiOH to give the desired carboxylic acid 10-3.

$^1$H NMR (CDCl$_3$) δ 8.75 (s, 1H); 7.43 (d, 1H); 7.18 (d, 1H); 4.21 (t, 2H); 2.85 (t, 3H); 1.4 (s, 9H).

3-[1-cyano-3-oxo-6-2-(piperidin-4-yl)ethylcarbamoyl)-2,3-dihydroimidazo[1,5-a]pyridin-2-yl]propionic acid (10-4)

10-3 (170 mg, 0.51 mmol) was dissolved in 10 ml of CH$_2$Cl$_2$, Et$_3$N (71 ml, 0.51 mmol) was added along with HOBT (69.3 mg, 0.51 mmol), EDC (98.6 mg, 0.52 mmol) and 2-4 (117.2 mg, 0.51 mmol). The mixture was stirred under N$_2$ for 18 h then washed with 10% citric acid, H$_2$O and brine (10 ml each) and dried over Na$_2$SO$_4$, concentrated and chromatographed giving a yellow solid (215 mg, 0.43 mmol). This material was deprotected using trifluoroacetic acid in CH$_2$Cl$_2$ to give the 10-4.TFA salt as a yellow solid, m.p.=173°.

$^1$H NMR (300 MHz, DMSO d$_6$) δ 1.75 (s, 1H); 7.43 (t, 1H); 7.31 (d, 1H); 7.15 (d, 1H); 4.23 (t, 2H); 3.41 (t, 2H); 3.23 (d, 2H); 2.83 (m, 2H); 1.85 (d, 2H); 1.53 (m, 2H); 1.41 (m, 1H); 1.32 (m, 2H).

SCHEME 11

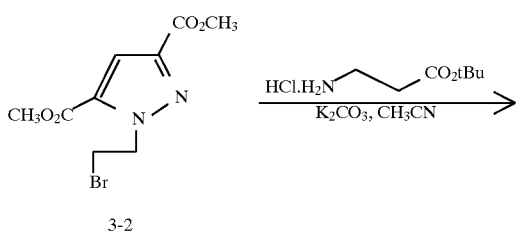

-continued
SCHEME 11

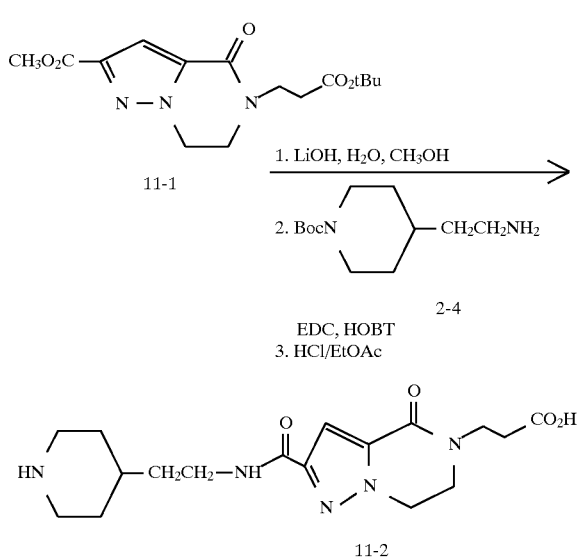

Methyl [4,5,6,7-tetrahydro-4-oxo-5-[3(tertbutyl propionyl)]pyrazolo [1,5-a]pyrazin-2-yl]carboxylate (11-1)

3-2 (1.4 g, 4.8 mmol), β-alanine tert-butyl ester.HCl (0.90 g, 5 mmol), and potassium carbonate (0.78 g, 5.28 mmol) in 150 ml $CH_3CN$ was refluxed under $N_2$ for 4.5 h then cooled, filtered and evaporated at reduced pressure. The resulting yellow residue was chromatographed on silica gel using 2% $CH_3OH/CH_2Cl_2$ giving the diester 11-1 as a colorless glass.

$^1$H NMR ($CDCl_3$) δ 7.31 (s, 1H); 4.48 (t, 2H); 3.93 (s, 3H); 3.61 (t, 2H); 2.71 (t, 2H); 2.35 (t, 2H); 1.23 (s, 9H).

3-[4,5,6,7-Tetrahydro-4-oxo-2-(2-(piperidin-4-yl)ethylcarbamoyl)-pyrazolo[1,5-a]pyrazin-5-yl]propionic acid (11-2)

A solution containing LiOH (145 mg, 3.41 mmol) in 10 ml $H_2O$ was added to a solution of the ester 11-1 (1.0 g, 3.1 mmol) in 10 ml $CH_3OH$ and the mixture was heated to 60° C. for 2.5 h then cooled and the solvent removed at reduced pressure. The remaining residue was acidified with 10% citric acid and extracted $CH_2Cl_2$ (2×100 ml). The pooled organic extracts were washed with $H_2O$, dried and evaporated to afford the desired acid as a colorless glass.

$^1$H NMR ($CDCl_3$) δ 7.21 (s, 1H); 4.48 (t, 2H); 3.63 (t, 2H); 2.71 (t, 2H); 2.32 (t, 2H); 1.23 (s, 9H).

This acid (500 mg, 1.62 mmol) was dissolved in 10 ml of $CH_2Cl_2$, HOBt (220 mg, 1.62 mmol) was added along with EDC (309 mg, 1.62 mmol), and 2-4 (356 mg, 1.63 mmol). The mixture was stirred under $N_2$ for 16 h then washed with 10% citric acid, $H_2O$ and brine (10 ml each) and dried over $Na_2SO_4$, concentrated and chromatographed giving a colorless foam. This material was deprotected using HCl in ethyl acetate, to give the HCl salt of 11-2 as a white solid. MP=192°–194° C.

$^1$H NMR (300 MHz, DMSO $d_6$) δ 9.0 (br, s, 1H); 8.35 (m, 1H); 6.99 (s, 1H); 4.38 (t, J=6.0 Hz, 2H); 3.83 (t, J=5.5 Ht, 2H); 3.64 (t, J=7.1 Hz, 2H); 3.30–3.1 (m, 4H); 2.85–2.65 (q, 2H); 2.54 (t, J=7.1 Hz, 2H); 1.85–1.75 (s, br, 2H); 1.60–1.20 (overlapping m, 5H).

SCHEME 12

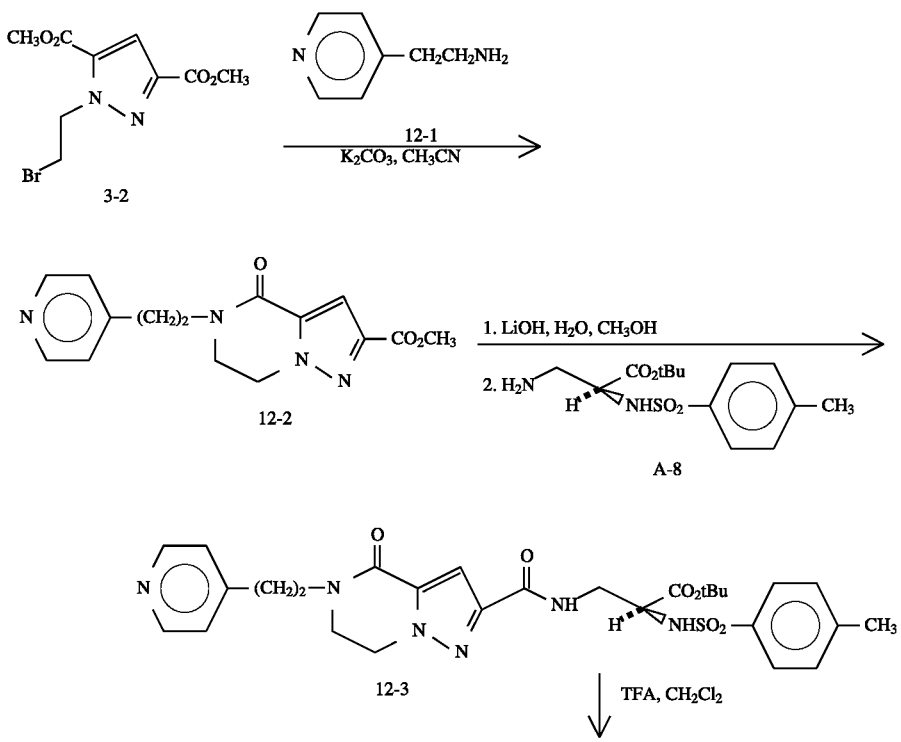

-continued
SCHEME 12

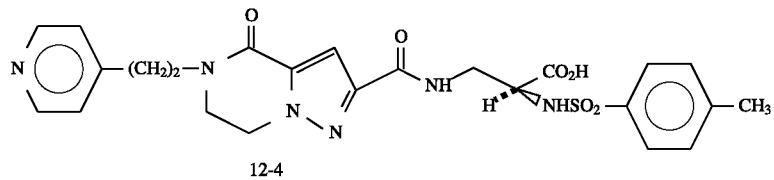

12-4

2-(4-Pyridyl)ethylamine (12-1)

A solution of NH₄Cl in 200 ml of H₂O was placed in a 1L Flask. 4-Vinyl pyridine (56.4 ml, 0.52 mol) was added along with 150 ml CH₃OH and on the mixture heated at 60° for 18 h. The reaction solution was cooled to 0° in an ice bath and made basic by the addition of 30% NaOH. The basic solution was extracted with CH₂Cl₂ (5×100 ml) and the pooled extracts dried, then evaporated. Vacuum distillation of the residue afforded 12-1 as a colorless liquid.

¹H NMR (300 MHz, CDCl₃) δ 8.53 (d, 3=6.1 Hz, 2H); 7.25 (d, J=6.1 H2, 2H); 3.02 (t, 2H); 2.77 (t, 2H); 1.4 (brs, 2H).

Methyl [4,5,6,7-tetrahydro-4-oxo-5-[2-(pyridin-4-yl)ethyl] pyrazolo-[1,5-a]pyrazin-2-yl]carboxylate (12-2)

A solution of 3-2 (1.4 g, 4.8 mmol), 4-(2-aminoethylpyridine) (0.645 g, 5.28 mmol), and potassium carbonate (0.78 g, 5.28 mmol) in 150 ml CH₃CN was refluxed under N₂ for 4.5 h then cooled, filtered and evaporated at reduced pressure. The resulting yellow residue was redissolved in 50 ml of DMF and treated with NaH (200 mg of a 60% oil dispersion) and heated at 90° for 3 h then concentrated at reduced pressure and chromatographed on silica gel using 20% CH₃OH/CH₂Cl₂ giving the ester a 12-2 as a pale yellow glass (0.91 g, 3.0 mmol, 68%).

¹H NMR (CDCl₃) δ 8.32 (d, 2H); 7.52 (d, 2H); 7.34 (s, 1H); 4.48 (t, 2H); 3.91 (s, 3H); 3.61 (t, 2H); 2.71 (t, 2H) 2.35 (t, 2H).

tert-Butyl 2(S)-[(p-toluenesulfonyl)amino]-3-[[[4,5,6,7-tetrahydro-4-oxo-5-[2-(4-pyridyl)ethyl]pyrazolo[1,5-a]pyrazin-2-yl]carboxylate (12-3)

A solution containing LiOH (130 mg, 3.05 mmol) in 10 ml H₂O was added to a solution of 12-2 (910 mg, 3.0 mmol) in 10 ml CH₃OH and the mixture was heated to 60° for 2.5 h then cooled and the solvent removed at reduced pressure. The remaining residue purified by ion exchange chromatography on Dowex-50W resin to affording the desired acid as an off-white solid, mp 187°.

This acid (300 mg, 0.78 mmol) was suspended in 50 ml of anhydrous DMF, A-8 (293 mg, 81 mmol), EDC (150 mg, 0.78 mmol), HOBt (105 mg, 0.78 mmol) and N-methyl morpholine (87 ml, 0.78 mmol) were added and the resulting clear solution was stirred at 25° C. for 19 h. The solution was diluted with 100 ml of EtOAc, washed successively with sat. NaHCO₃, H₂O, and brine (25 ml), dried over Na₂SO₄ and evaporated to provide 12-3.

¹H NMR (300 MHz, DMSO-d₆) δ 8.63 (d, 2H); 7.80 (d, 2H); 7.58 (d, 2H); 7.29 (t, 1H); 6.93 (s, 1H); 5.95 (d, 2H); 4.40 (t, 2H); 4.08 (m, 1H); 3.86–3.74 (m, 4H); 3.35–3.20 (m, 2H); 3.10 (t, 2H); 1.30 (s, 9H);

2(S)-[(p-Toluenesulfonyl)amino]-3-[[[4,5,6,7-tetrahydro-4-oxo-5-[2-(4-pyridyl)ethyl]pyrazolo[1,5-a]pyrazin-2-yl] carboxylic acid.TFA salt (12-4)

12-3 was deprotected using TFA in CH₂Cl₂ and purified by reverse phase chromatography to give 12-4 as its TFA salt, mp 182°–185°.

¹H NMR (300 MHz, DMSO-d₆) δ 8.72 (br d, 2H); 8.19 (t, 1H); 8.00 (d, 1H); 7.81 (d, 2H); 7.58 (d, 2H); 7.19 (d, 2H); 6.85 (s, 1H); 4.40 (t, 2H); 4.01 (m, 1H); 3.83–3.76 (m, 4H); 3.48 (m, 1H); 3.26 (m, 1H); 3.10 (t, 2H).

SCHEME 13

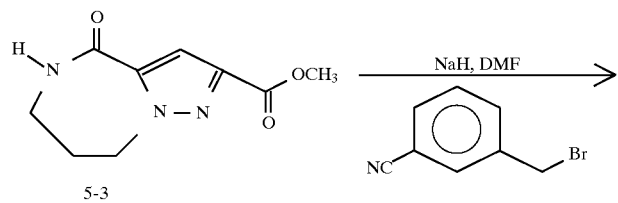

5-3

-continued
SCHEME 13

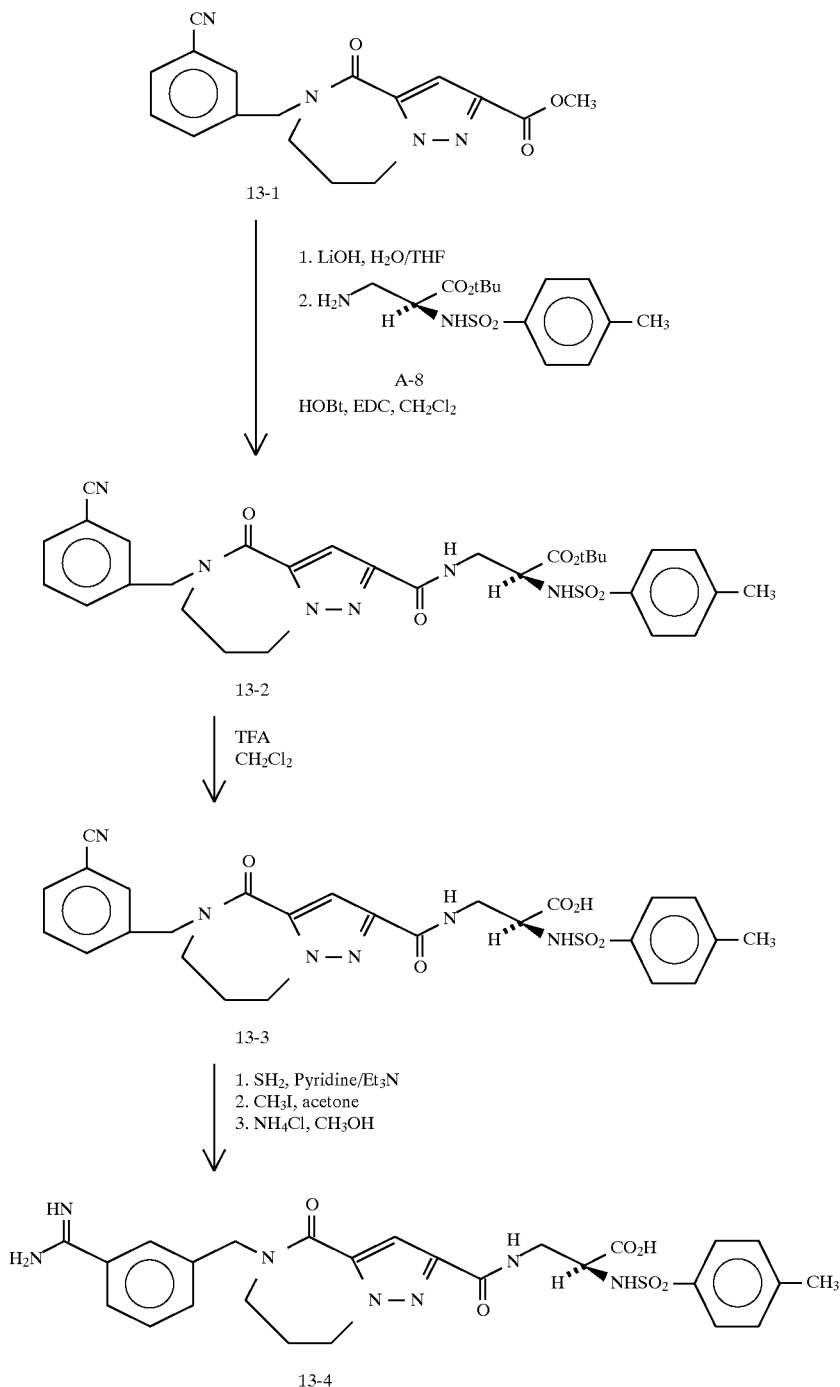

Methyl-5,6,7,8-tetrahydro-4-oxo-5-[3(cyanophenyl)methyl-4-H-pyrazolo[1,5-a][1,4]diazepin-2-yl]carboxylate (13-1)

A solution of 5-3 (3.02 g, 14.5 mmol) in 60 ml anhydrous DMF was cooled to 0° C. and treated with NaH (60% in oil) (636 mg, 15.98 mmol). The resulting mixture was stirred at 0° for 1.5 h, then a solution of 3-cyanobenzyl bromide (3.11 g, 15.89 mmol) in 50 ml of DMF was added dropwise. The resulting mixture was stirred at 25° for 18 h then diluted with 200 ml EtOAc and washed with $H_2O$ (3×100 ml) and brine (100 ml). The organic layer was dried ($NaSO_4$), filtered and evaporated. The resulting solid was recrystallized from $CH_2Cl_2/CH_3OH$ to give 13-1 as a white solid.

$^1$H NMR ($CDCl_3$) δ 7.85 (s, 1H); 7.78 (d, J=8 Hz, 1H); 7.59 (d, J=8 Hz, 1H); 7.46 (m, 1H); 7.30 (s, 1H); 4.80 (s, 1H); 4.43 (t, J=8 Hz, 2H); 3.89 (s, 3H); 3.38 (t, J=8 Hz, 2H); 2.09 (m, 2H).

tert-Butyl 2(S)-[(p-Toluenesulfonyl)amino]-3-[[[5,6,7,8-tetrahydro-4-oxo-5-[(3-cyanophenyl)methyl]-4H-pyrazolo[1,5-a][1,4]diazapin-2-yl]-carbonyl]amino]propanoate (13-2)

A solution of ester 13-1 (1.5 g, 4.04 mmol) in 100 ml THF was treated with 1N LiOH (5.1 ml, 5.1 mmol) and 100 ml H₂O and stirred at 25° for 1.5 h. The THF was removed at reduced pressure and the aqueous residue acidified with 1N HCl. The resulting precipitate was filtered and dried in vacuo to give the desired product as a white solid.

¹H NMR (CDCl₃) δ 7.95 (s, 1H); 7.73 (d, 1H); 7.53 (d, 1H); 7.43 (m, 1H); 7.30 (s, 1H); 4.85 (s, 2H); 4.43 (t, 2H); 3.31 (t, 2H); 2.08 (m, 2H).

The above acid (1.0 g, 3.23 mmol) was combined with A-9 (1.24 g, 3.54 mmol), HOBt (480 mg, 3.54 mmol); EDC (641 mg, 3.54 mmol) in 100 ml CH₂Cl₂. N-methyl morpholine (403 μl, 3.83 mmol) was added and the resulting solution stirred at room temperature for 16 h, then was washed successively with sat. NaHCO₃, 10% KHSO₃ and brine (100 ml each), then dried over Na₂SO₄, filtered and evaporated. The residue was chromatographed on silica gel (EtOAc) to give 13-2 as a white solid.

¹H NMR (300 MHz, CDCl₃) δ 7.73 (d, J=6.8 Hz, 2H); 7.68 (s, 1H); 7.65 (d, 1H); 7.51 (m, 1H); 7.37 (d, J=6.8 Hz, 2H); 7.20 (d, 1H); 7.18 (t, 1H); 5.63 (d, J=6.5 Hz, 1H); 4.80 (s, 2H); 4.78 (m, 1H); 4.45 (t, 2H); 3.85 (m, 1H); 3.08 (m, 1H); 3.40 (t, 2H); 2.43 (s, 3H); 2.19 (m, 2H); 1.65 (s, 9H). 2(S)-[(p-toluensulfonyl)amino]-3-[[[5,6,7,8-tetrahydro-4-oxo-5-[(3-cyanophenyl)methyl]-4H-pyrazolo[1,5-a][1,4]diazapin-2-yl]carbonyl]-amino]propanoate (13-3)

A solution of 13-2 in CH₂Cl₂ (15 ml) was treated with 5 ml of TFA. The solution was stirred at 0° for 2.5 h then evaporated giving 13-3 as a colorless solid.

¹H NMR (300 MHz, CDCl₃) δ 7.73 (d, J=6.8 Hz, 12H); 7.65 (s, 1H); 7.65 (d, 1H); 7.50 (m, 1H); 7.31 (d, J=6.8 Hz, 2H); 7.3 (d, 1H); 7.28 (t, 1H); 6.15 (d, J=6.5 Hz, 1H); 4.80 (s, 2H); 4.63 (m, 1H); 4.43 (t, 2H); 3.82 (m, 1H); 3.65 (m, 1H); 3.48 (m, 2H); 2.43 (s, 3H); 2.19 (m, 2H).

2(S)-[(p-Toluenesulfonyl)amino]-3-[[[5,6,7,8-tetrahydro-4-oxo-5-[(3-amidinophenyl)methyl]-4H-pyrazolo[1,5-a][1,4]diazapin-2-yl]-carbonyl]amino]propanoic acid (13-4)

13-3 (400 mg, 0.73 mmol) was dissolved in 10 ml of a 4:1 mixture of pyridine and Et₃N. The solution was saturated with SH₂ and stirred until the nitrile could no longer be detected by HPLC (2.5h). The excess SH₂ was removed by passing a stream of nitrogen through the solution. The remaining solution was then evaporated and the residue triturated with 1N HCl and filtered giving a yellow solid. This material was dissolved in 15 ml of acetone and treated with CH₃I (250 μl) and then heated to 50° until the thioamide could no longer be detected by HPLC (2 h). The solvent and excess CH₃I were evaporated and the residue redissolved in CH₃OH containing (NH₄)₂CO₃ (144 mg, 1.14 mmol). The solution was heated at 50° for 12.5 h then evaporated, and 13-4 was isolated by preparative reverse phase chromatography.

¹H NMR (300 MHz, DMSO-d₆) δ 9.38 (s, 2H); 9.17 (s, 2H); 8.19 (t, 1H); 8.16 (d, 2H); 7.78 (s, 1H); 7.75 (m, 2H); 7.63 (m, 1H); 7.60 (d, 2H); 7.21 (d, 2H); 6.93 (s, 1H); 4.81 (s, 2H); 4.40 (t, 2H); 3.93 (m, 1H); 3.40 (m, 2H); 3.35 (m, 2H); 2.23 (s, 3H); 2.13 (m, 2H).

SCHEME 14

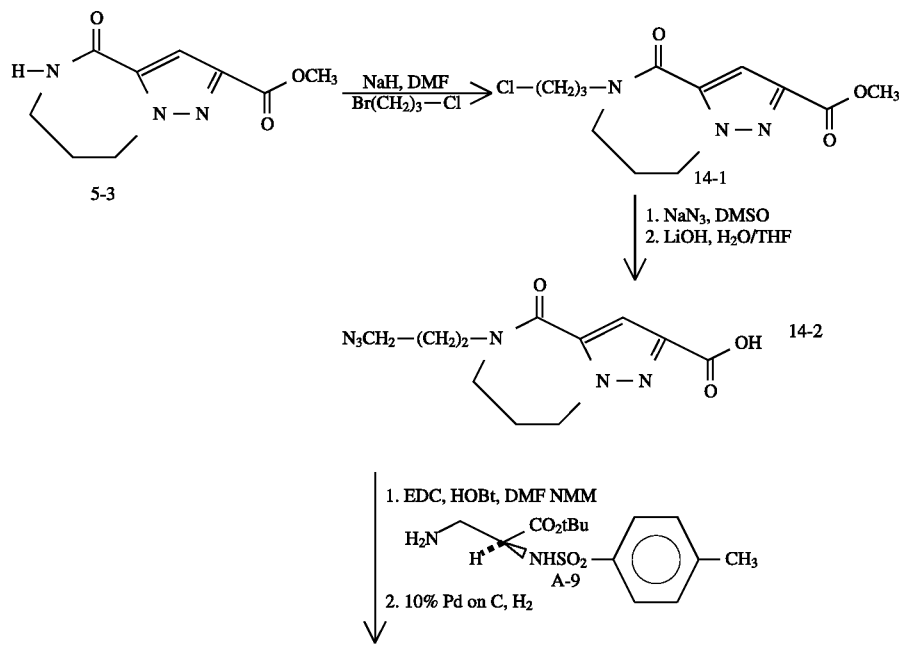

SCHEME 14 (continued)

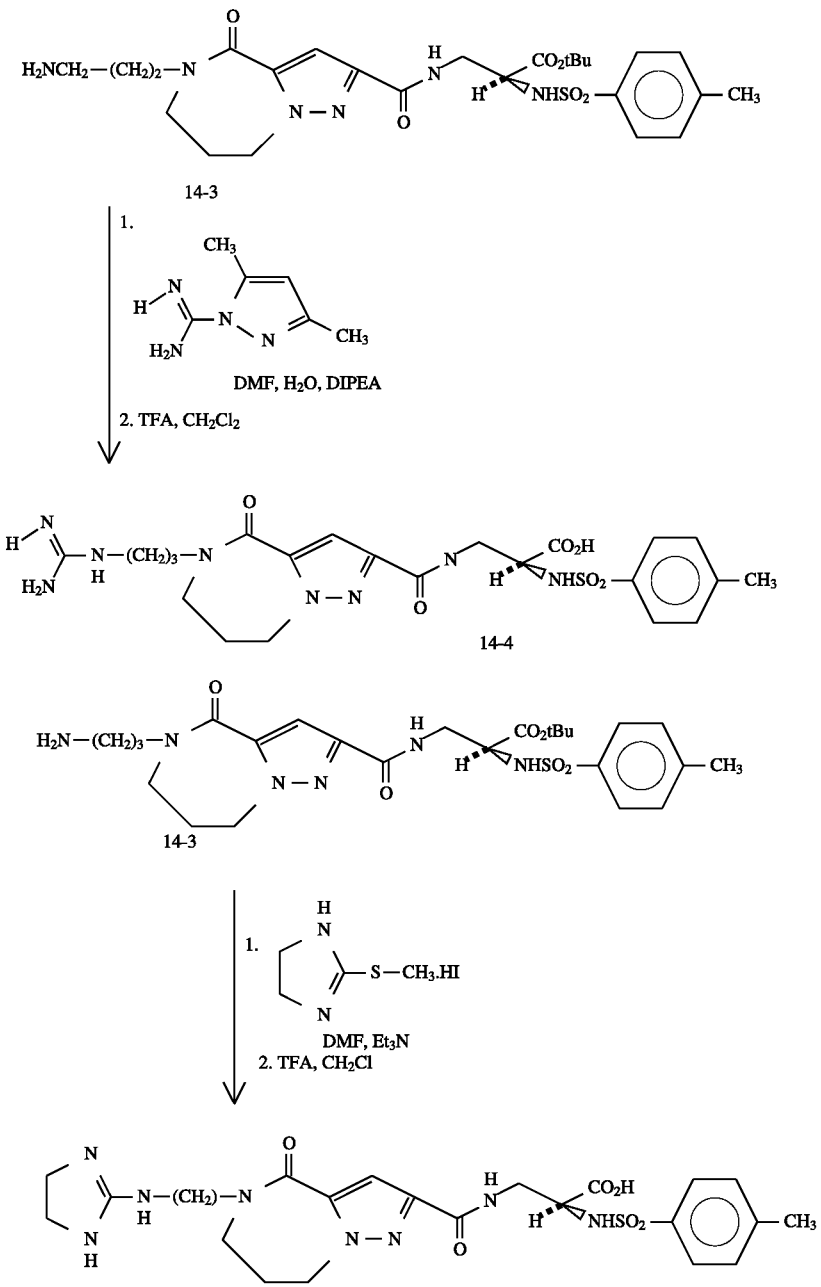

Methyl -5,6,7,8-tetrahydro-4-oxo-5-(3-chloropropyl)-4H-pyrazolo-[1,5-a][1,4]diazepin-2-yl]carboxylate (14-1)

5-3 (2.0 g, 9.5 mmol) was alkylated with 1-chloro-3-bromo propane (1.5 ml, 10.5 mmol) was described for 13-1 to give 14-1 as a white solid.

$^1$H NMR (300 MHz, CDCl$_3$) δ 7.28 (s, 1H); 4.58 (t, 2H); 3.93 (s, 3H); 2.78 (t, 2H); 2.68 (t, 2H); 2.46 (t, 2H); 3.27 (m, 2H); 2.18 (m, 2H).

5,6,7,8-Tetrahydro-4-oxo-5-(3-azidopropyl)-4H-pyrazolo[1,5-a][1,4]-diazepin-2-yl]carboxylic acid (14-2)

A solution of this chloride (909 mg, 3.2 mmol) and NaN$_3$ (620 mg, 9.5 mmol) in DMF (15 ml) was stirred at room temperature for 36 h. The solution was diluted with ethyl acetate (50 ml) the washed with H$_2$O (3×50 ml), then dried (Na$_2$SO$_4$), filtered and evaporated to give the azide as a white solid. This material was hydrolyzed in the usual manner to afford 14-2 as a white solid.

$^1$H NMR (300 MHz, DMSO-d$_6$) δ 7.00 (s, 1H); 4.41 (t, 2H); 3.52 (t, 2H); 3.41 (t, 2H); 3.26 (t, 2H); 2.20 (m, 2H); 1.80 (m, 2H).

tert-Butyl 2(S)-(p-Toluenesulfonylamino)-3-[5,6.7,8-tetrahydro-4-oxo-5-(3-aminopropyl)-4H-pyrazolo[1,5-a][1,4]diazepin-2-yl]carboxyl)amino)propionate (14-3)

The acid 14-2 was coupled with A-9 as described for 13-2 to give the desired product as a white solid. This material was dissolved in ethanol and residual over 10% Pd on C under a H$_2$ atmosphere to give 14-3 as a white solid.

$^1$H NMR (300 MHz, DMSO -d$_6$) 8.18 (t, 1H); 7.68 (d, 2H); 7.23 (d, 2H); 6.98 (s, 1H); 4.4 (m, 3H); 3.93 (t, 2H);

3.48–3.2 (m, 6H); 2.78 (t, 2H); 2.43 (s, 3H); 2.69 (m, 2H); 1.86 (m, 2H); 1.08 (s, 9H).

2(S)-(p-Toluenesulfonylamino)-3-[5,6,7,8-tetrahydro-4-oxo-5-(3-guanidinopropyl)-4H-pyrazolo[1,5-a][1,4]diazepin-2-yl]carbonyl)amino)propionic acid (14-4)

A solution of 14-3 (60 mg, 0.1 mmol) in DMF (5 ml) was treated with DIPEA (90 μl, 0.5 ml) and 3,5-dimethylpyrazole-1-carboxamidine (30 mg, 0.5 mmol) and heated at 80° C. for 12 h. The solution was evaporated and the residue purified by chromatography on neutral aluminia ($CH_2Cl_2/CH_3OH/NH_4OH$, 80/20/1) to give the desired product as a white solid. This material was deprotected with TFA in the usual manner and purified by preperative reverse-phase chromatography to give (14-4) as a white solid.

$^1$H NMR (300 MHz, $D_2O$) δ 8.2 (t, 1H); 7.58 (s, 2H); 7.18 (d, 2H); 4.38 (t, 2H); 3.51 (m, 5H); 3.45 (t, 2H); 3.2 (m, 1H); 3.18 (m, 2H); 2.10 (s, 3H); 2.08 (m, 2H); 1.8 (m, 2H).

2(S)-(p-Toluenesulfonylamino)-3-[5,6,7,8-tetrahydro-4-oxo-5-[3[N-(imidazolin-2-yl)amino]propyl]-4H-pyrazolo[1,5-a][1-4]diazepin-2-yl]carboxyl]amino]propionic acid (14-5)

A solution of 14-3 was reacted with 2-methylthio-2-imidazoline hydroiodide using the procedure described in 14-4. The crude material was deprotected with TFA and 14-5 isolated by preperative reverse-phase chromatography.

$^1$H NMR (300 MHz, DMSO-$d_6$) 8.20 (t, 1H); 8.10 (d, 2H); 7.60 (d, 2H); 7.21 (d, 3H); 6.86 (s, 1H); 4.46 (t, 2H); 4.01 (m, 2H); 3.8–3.5 (overlapping m, 8H); 2.23 (s, 3H); 2.10 (t, 2H); 1.80 (t, 2H).

syringe, and the resulting solution was stirred for 0.5 h to afford the desired mixed anhydride.

A-7 (7.00 g, 27.1 mmol), THF (125 ml), and diisopropylethylamine (4.71 ml, 27.1 mmol) were combined in a 500 ml round bottom flask with a magnetic stir bar. Water was added in small portions until a clear solution resulted. The resulting solution was cooled in an ice bath. The mixed anhydride suspension was added in a single portion to the solution of 9 with vigorous mixing. After 20 min. stirring the reaction solution was concentrated to remove THF. The remaining aqueous material was acidified with 10% potassium bisulfate and the resulting precipitate was filtered to give white solid.

This material was subjected to flash column chromatography using silica (EM Science, 230–400 mesh, 10×20 cm). The column was eluted with methylene chloride:methanol:ammonium hydroxide 98:2:0.2, 95:5:0.5, 90:10:1, then 85:15:1.5 to give the pure 15-1 as a white solid.

$^1$H NMR (DMSO-$d_6$) δ 8.23 (q, J=3.40 Hz, 1H); 7.64 (d, J=8.20 Hz, 2H); 7.32 (d, J=8.20 Hz); 7.2–7.0 (br, 1H); 6.86 (s, 1H); 4.36 (t, J=6.70 Hz, 2H); 3.89 (d, br, J=12.21 Hz, 2H); 3.59 (m, 1H); 3.47 (t, J=7.08 Hz, 2H); 3.5–3.1 (m, br, 5H, $H_2O$); 2.8–2.6 (br, 2H); 2.33 (s, 3H); 2.17 (t, J=6.47 Hz, 2H); 1.66 (d, br, J=11.97 Hz, 2H); 1.55–1.45 (m, br, 3H); 1.37 (s, 9H); 1.1–0.9 (m, br, 2H).

2(S)-[(p-Toluenesulfonyl)amino]-3-[[[5,6,7,8-tetrahydro-4-oxo-5-[2-(piperidin-4-yl)ethyl]-4H-pyrazolo-[1,5 -a][1,4]diazepin-2-yl]carbonyl]-amino]propionic acid (15-2)

15-1 (7.42 g, 11.48 mmol) was placed in a 1L round bottom flask equipped with a magnetic stir bar. Methylene

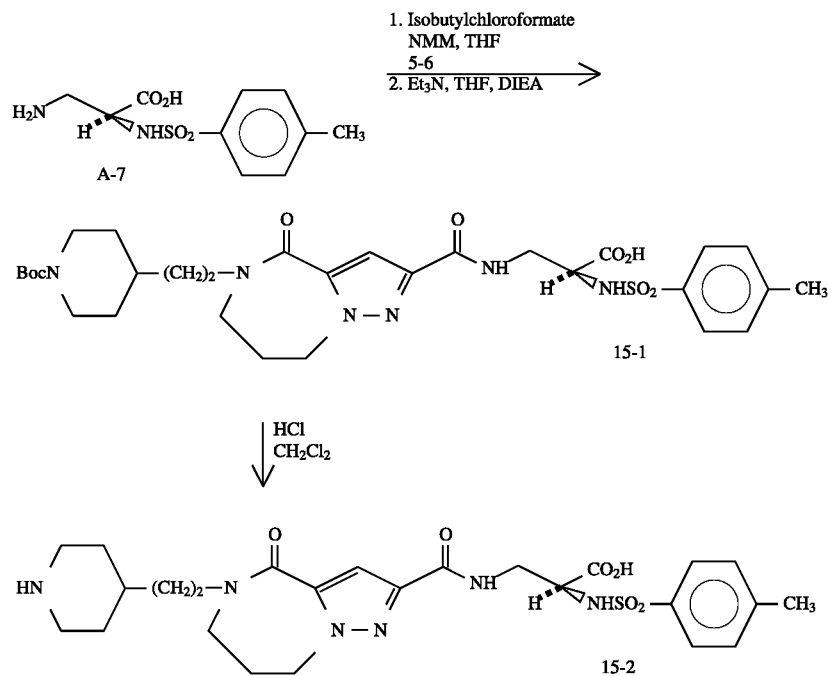

SCHEME 15

2(S)-[(p-Toluenesulfonyl)amino]-3-[[[5,6,7,8-tetrahydro-4-oxo-5- [2-(N-BOC-piperidin-4-yl)ethyl]-4H-pyrazolo[1,5-a]-[1,4]diazepin-2-yl]-carbonyl]amino]propionic acid (15-1)

A solution of 5-6 (5.0 g, 12.3 mmol) in THF (150 ml) was cooled to 0°–10° and N-methylmorpholine (2.11 ml, 19.2 mmol) was added via syringe. After mixing 20 min., isobutyl chloroformate (2.38 ml, 18.2 mmol) was added dropwise via chloride was added and the reaction mixture was cooled to 0°–5°. Hydrogen chloride was bubbled through the suspension with stirring. After about 2 min. the solid went into solution, and soon afterward a second precipitate formed. After bubbling gas through the suspension for an additional 5 min. the reaction flask was warmed to room temperature. After 30 min. the contents of the reaction flask were concentrated. The resulting white solid was the hydrochloride salt of 15-2 and by HPLC analysis was of >99% purity.

This hydrochloride salt of 15-2 was subjected to ion exchange chromatography using Dowex 50X8-200 ion exchange resin (110 g, 4.11 meq/g). The resin was prepared by washing with water, methanol, water, 6N hydrochloric acid, and water (500 ml each). At this time the eluent was pH 7. The hydrochloride was dissolved in water (30 ml) and then applied to the top of the column. The column was eluted with water. The pH of the eluant became strongly acidic. When the pH of eluant returned to 7, the column was eluted with ammonium hydroxide:acetonitrile:water 50:25:25 (1.5 L). Portions containing U.V. active material were combined then concentrated at high vacuum. The resulting white foam was dried for 8 h on the high vacuum to provide 15-2.

$^1$H NMR (DMSO-d$_6$) δ 9.0–8.5 (br, 1H); 8.19–8.16 (m, 1H); 7.67 (d, J=8.18 Hz, 2H); 7.32 (d, J=8.18 Hz, 2H); 6.89 (s, 1H); 4.38 (t, J=6.84 Hz, 2H); 3.75–3.65 (m, br, 1H); 3.46 (t, br, 2H); 3.5–3.1 (m, br, 8H, H$_2$O); 2.77 (t, br, J=11.36, 2H); 2.35 (s, 3H); 2.17 (t, J=6.47 Hz, 2H); 1.80 (d, br, J=12.7 Hz, 2H); 1.53–1.42 (m, br, 3H); 1.33–1.24 (m, br, 2H).

Using the methods set forth previously, particularly in Schemes 3 and 4, the following compounds of Table 1 were prepared.

TABLE 1

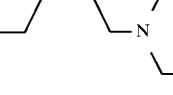

| R | mp (°C.) | salt form |
|---|---|---|
| 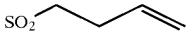 | 115–120 | TFA |
| 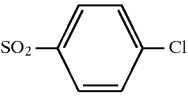 | 110–120 | TFA |
| 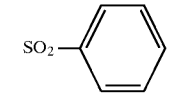 | 160–165 | zwiterion |
| H | 195–198 | zwiterion |
| 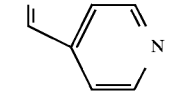 | 150–155 | HCl |
|  | 180–188 | HCl |
|  | 195–200 | zwiterion |
| 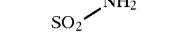 | 121–124 | TFA |

TABLE 1-continued

| R | mp (°C.) | salt form |
|---|---|---|
| SO$_2$–CH$_2$CH$_2$CH=CH$_2$ | 210–212 | TFA |
| SO$_2$–CH$_3$ | 85–95 | TFA |
| SO$_2$–C$_6$H$_4$–Cl | 175–180 | TFA |
| SO$_2$–C$_6$H$_5$ | 115-120 | HCl |
| pyridyl-C(O)– | 78-80 | TFA |
| SO$_2$–NH–C$_4$H$_9$ | | HCl |
| SO$_2$–NH–C(O)O–CH$_2$Ph | 200 (dec) | HCl |
| SO$_2$–NH$_2$ | 210 (dec) | HCl |

Additional compounds, prepared according to procedures analogous to those of the exemplary procedures described above, are shown in the following tables:

TABLE 2

| R | A | B | mp(°C.) |
|---|---|---|---|
| –C(O)N(C$_2$H$_5$)$_2$ | H | H | 145–152 |
| –C(O)N(C$_2$H$_5$)H | H | H | 168–170 |
| –C(O)N(C$_2$H$_5$)H | H | H | 164–167 |

TABLE 2-continued

[Structure: HN-piperidine-CH2CH2-N(C(=O))-pyridine(R)-C(=O)-NH-CH(H^A)(CH2H^B)-CO2H]

| R | A | B | mp(°C.) |
|---|---|---|---|
| HC(=O)NH2 (formamide) | H | H | 110–135 |
| —CN | H | H | 180–188 |
| HC(=O)N(C2H5)2 | H | NHSO2C4H9 | 156–160 |
| HC(=O)NHCH3 | H | NHSO2C4H9 | 134–140 |
| HC(=O)N(CH3)2 | H | NHSO2C4H9 | 110–125 |
| HC(=O)-morpholino | H | NHSO2C4H9 | 130–135 |
| HC(=O)-pyrrolidino | H | NHSO2C4H9 | 128–135 |
| HC(=O)N(C2H5)2 | H | SO2-C6H4-CH3 | 185–190 |

TABLE 3

[Structure: HN-piperidine-(CH2)n-N(pyrazole N—N ring)-C(=O)...C(=O)-NH-(CH2)m-CH2CO2H]

| n | m | mp (°C.) |
|---|---|---|
| 2 | 0 | 110–115 |
| 2 | 1 | 115–120 |
| 1 | 1 | 121–123 |
| 0 | 2 | 135–141 |
| 0 | 1 | 140–145 |

TABLE 4

[Structure: HN-piperidine-CH2CH2-N-bicyclic(urea)-C(=O)-NH-CH(H)(R)-CO2H, H6 position marked]

| R | amide stereochemistry relative to H6 | NH* chemical shift (PPM) |
|---|---|---|
| H | cis | 6.35 |
| H | trans | 7.38 |
| NHSO2C4H9 | cis | 6.31 |
| NHSO2C4H9 | trans | 7.29 |

"H6" refers the hydrogen group at position 6 of the bicyclic structure

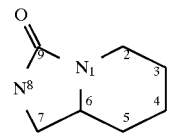

TABLE 5

[Structure: HN-piperidine-CH2CH2-N(with ring)-CH2-pyrazole(N—N)-C(=O)-N(R1)-CH(H)(CH2-NHR2)-CO2H]

| R1 | R2 | MP (°C.) |
|---|---|---|
| H | SO2C4H9 | 110–116 |
| H | SO2-C6H4-CH3 (para) | 186 |
| CH3 | SO2-C6H4-CH3 (para) | 164–171 |
| H | SO2-C6H4-Cl (para) | 164–170 |
| H | C(=O)CH2OH | 135–140 |
| H | SO2-CH2CH=CH2 | not determined |
| H | SO2-C6H3(Br)(CH3) | 173–174 |

TABLE 5-continued

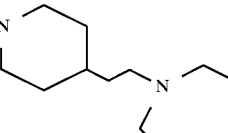

| $R_1$ | $R_2$ | MP (°C.) |
|---|---|---|
| H | (4-pyridyl-CO-) | 185–189 |
| H | H | 178–179 |

TABLE 6

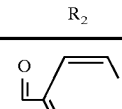

| n | $R_1$ | $R_2$ | MP (°C.) |
|---|---|---|---|
| 1 | H | H | 248–249 |
| 1 | H | $NHSO_2$-C$_6$H$_4$-CH$_3$ | 175–180 |
| 1 | $CH_3$ | H | 118–122 |
| 1 | CH | $NHSO_2$-C$_6$H$_4$-CH$_3$ | 155–160 |
| 2 | Ph | H | 137–139 |
| 2 | Ph | $NHSO_2$-C$_6$H$_4$-CH$_3$ | 185–188 |
| 2 | H | $NHSO_2$-C$_6$H$_4$-CH$_3$ | 192–194 |
| 2 | H | $NHCO_2$-Ph | 176–178 |
| 2 | H | $NHSO_2C_3H_7$ | 168–170 |
| 2 | H | $NHSO_2C_2H_5$ | 173–174 |

What is claimed is:

1. A compound having the formula

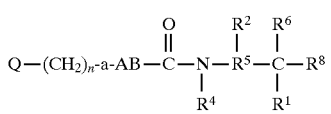

wherein Q is

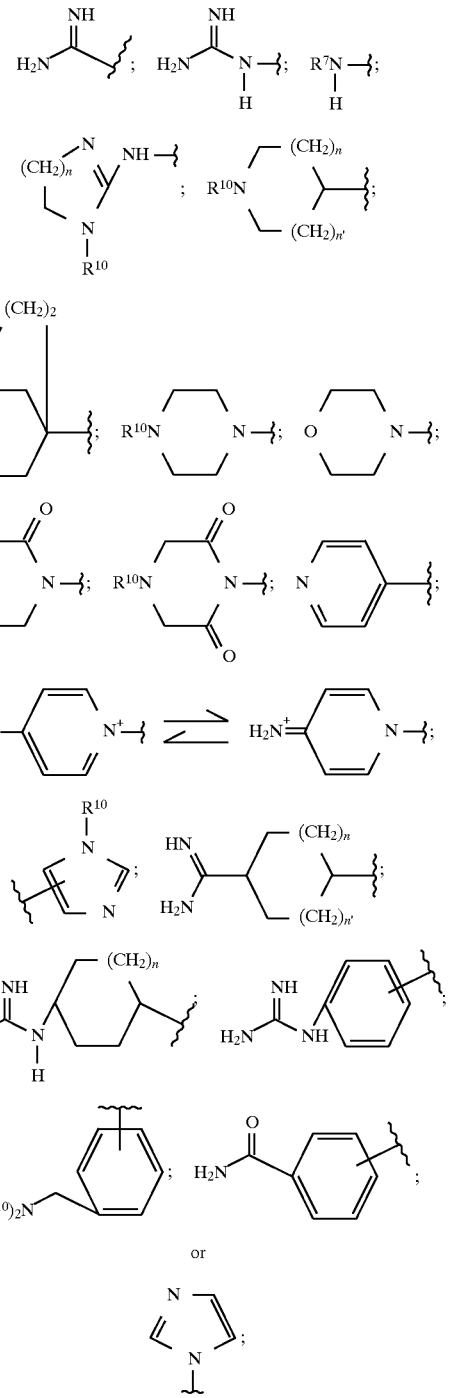

$n = 0–7$;
$n' = 0–3$;
$R^4 =$ H, $C_{3-4}$ alkyl, $C_{1-4}$ branched or straight chain alkyl, cyclic $C_{3-4}$ alkyl or $C_{1-4}$ alkenyl;
$R^5 =$ —CH(CH$_2$)$_n$, or a bond;
$R^2$ is H, or $C_{1-4}$ branched or straight chain alkyl;
$R^1 =$ H, $C_{1-4}$ alkyl, $N(R^{11})_2$, —$N(R^{11})SO_2R^{12}$, $NR^{11}CO_2R^{12}$, $NR^{11}C(O)R^{12}$, $NR^{11}C(O)N(R^{12})R^{13}$, $N(R^{11})SO_2N(R^{12})R^{13}$, $N(R^{11})SO_2N(R^{13})C(O)OR^{12}$, or $C(O)N(R^{12})_2$;

$R^6$=COOH, CH$_2$OH, C(O)N(R$^{14}$)$_2$, CO$_2$R$^9$, tetrazole, or

$R^7$, $R^{12}$, $R^{14}$, $R^{17}$, $R^{18}$, and $R^{19}$, are independently selected from H, branched or straight chain C$_{1-4}$ substituted or unsubstituted alkyl, branched or straight chain lower alkenyl, phenyl or substituted phenyl wherein substituted alkyl is hydroxy substituted or C$_{1-4}$ alkoxy substituted alkyl, and wherein substituted aryl is substituted by one two or three of the following groups: halogen, C$_{1-4}$ alkoxy, hydroxy, or C$_{1-4}$ alkyl;

$R^8$, $R^{10}$, $R^{11}$, $R^{13}$, $R^{20}$=H, branched or straight chain C$_{1-4}$ alkyl;

$R^9$=H or C$_{1-4}$ alkyl;

a=

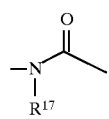

or a bond;

AB is

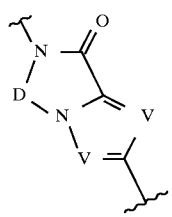

wherein V is N or CR$^{18}$, and D is CH$_2$, CH$_2$—CH$_2$, CH$_2$C(R$^{19}$)$_2$CH$_2$, or

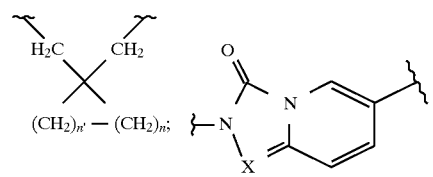

wherein X=N or CR$^3$, wherein R$^3$=CN, C(O)N(R$^{18}$)R$^{20}$

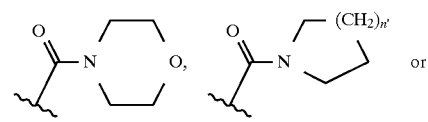

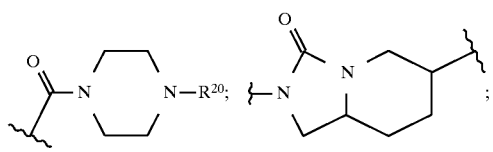

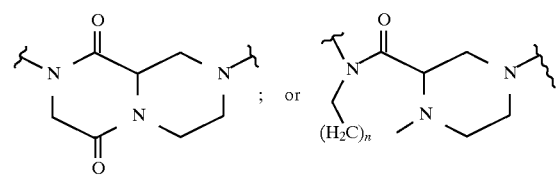

and pharmaceutically acceptable salts thereof.

2. A compound of claim 1 which is selected from

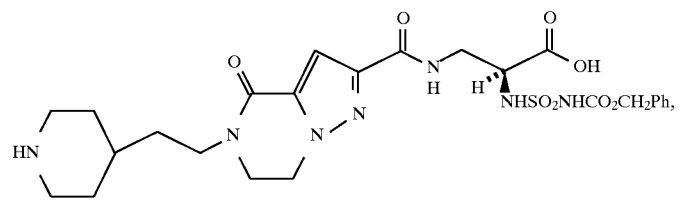

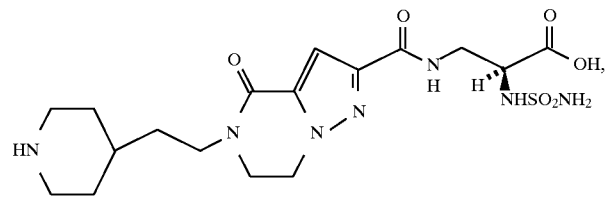

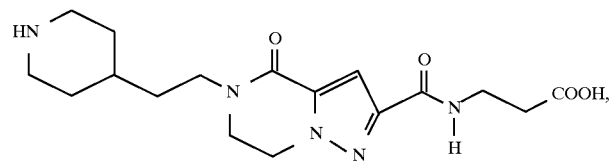

-continued
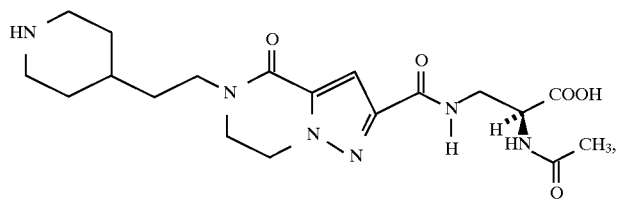
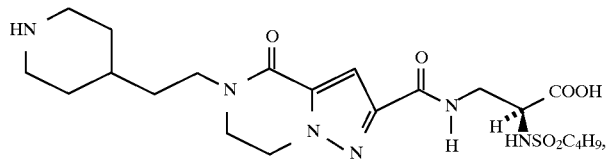
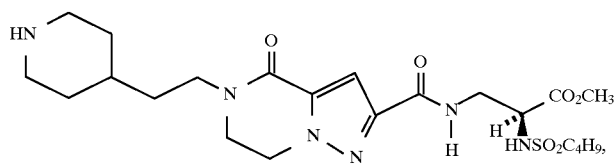
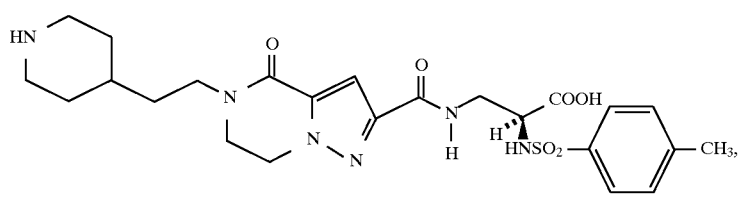
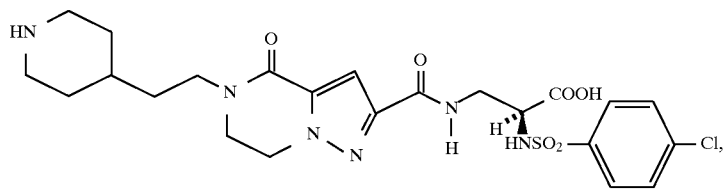
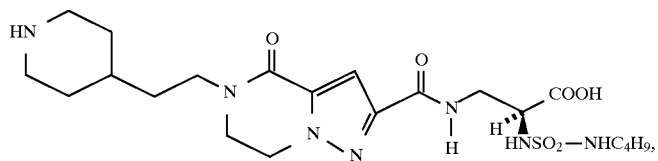
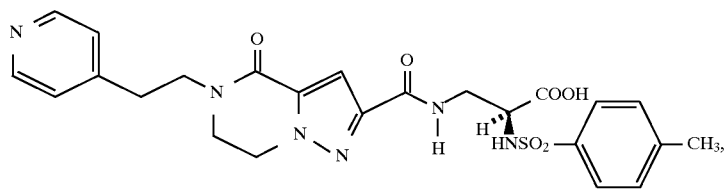
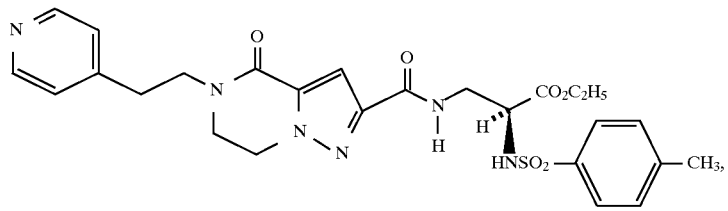

-continued
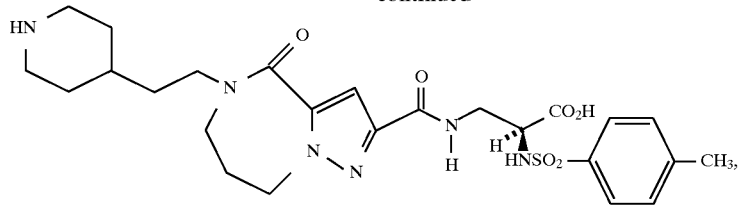
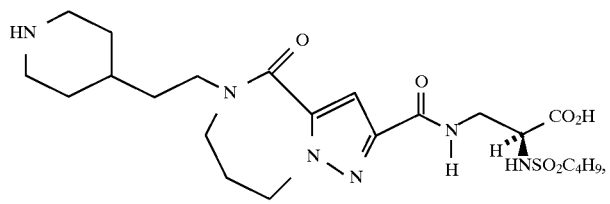
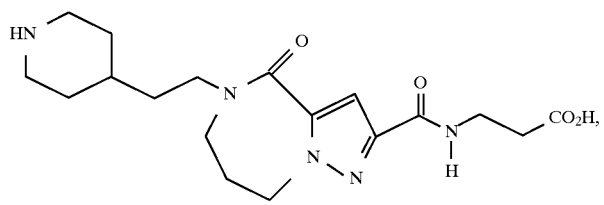
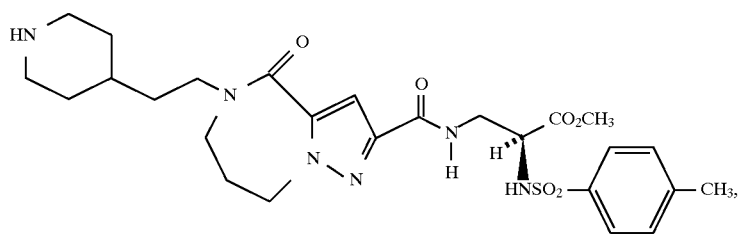
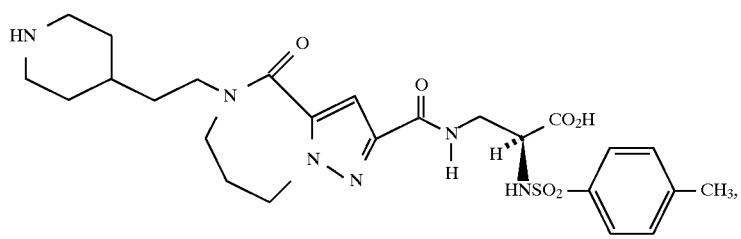
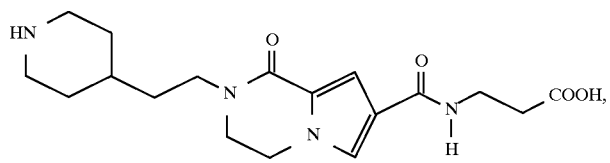
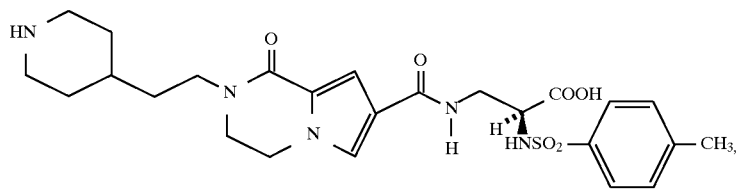
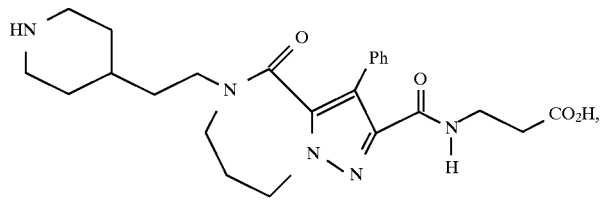

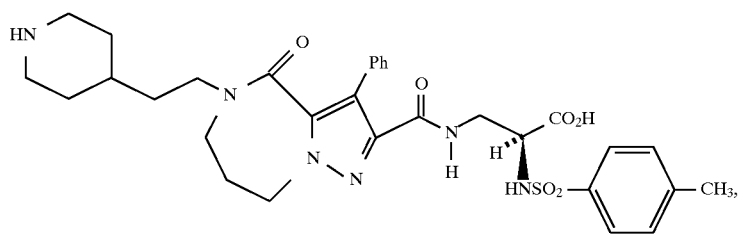
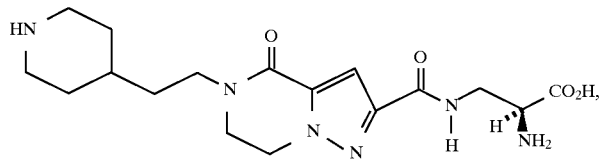
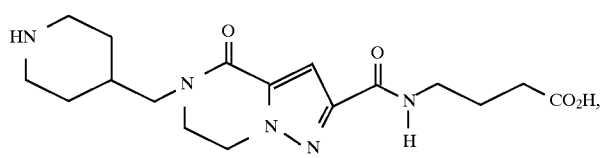
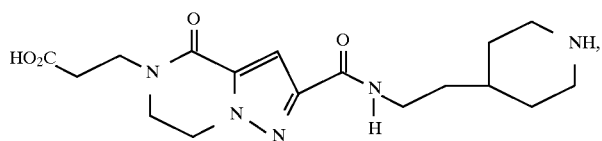
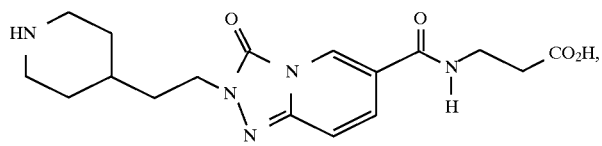
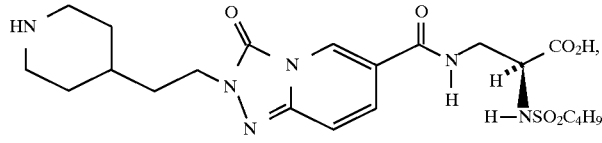
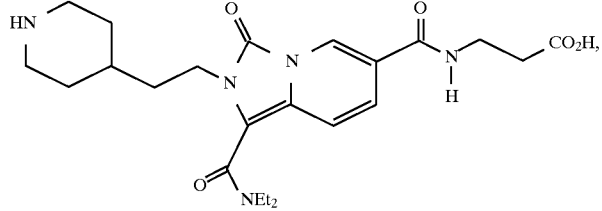
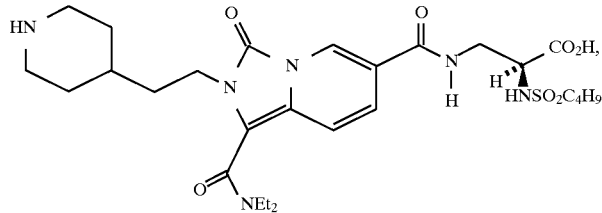
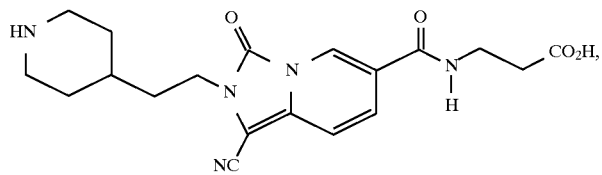

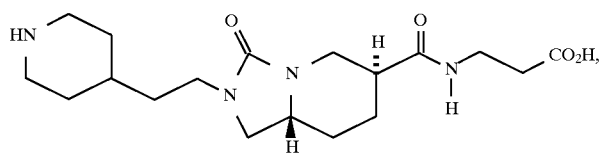
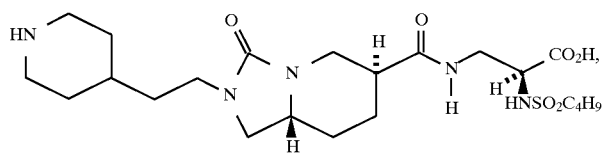
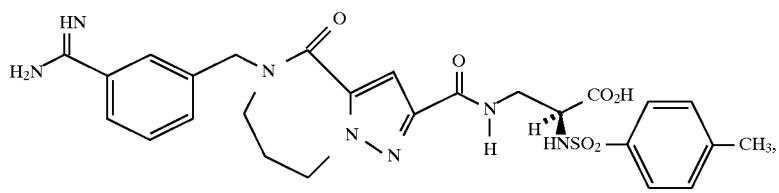
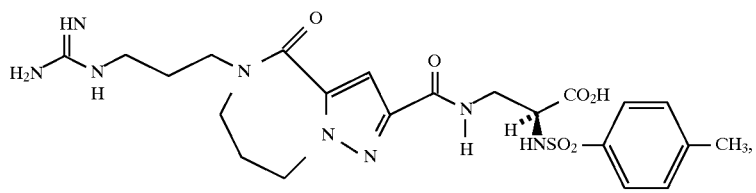
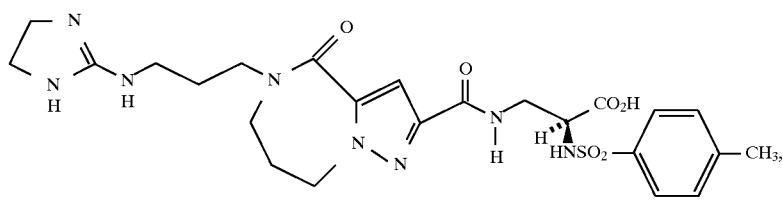
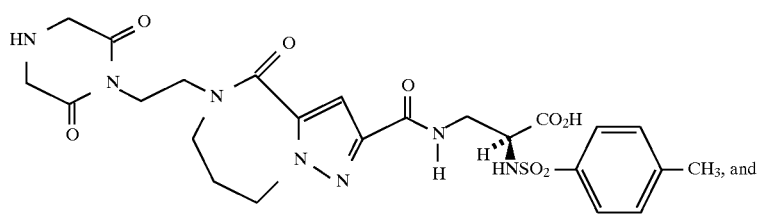
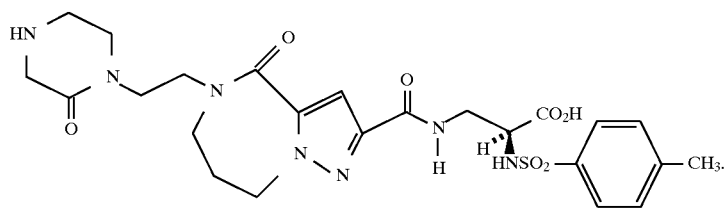

3. A compound of claim 2 selected from the group consisting of

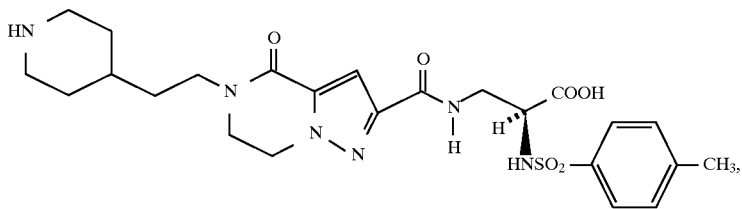

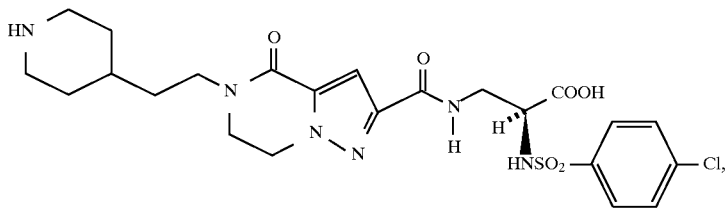

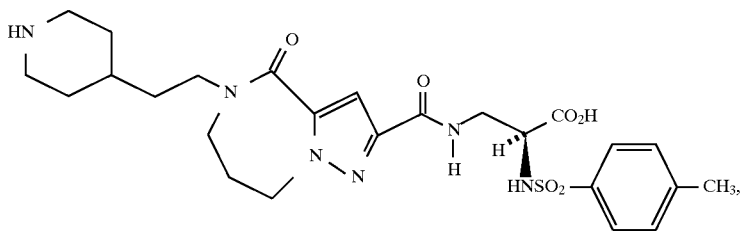

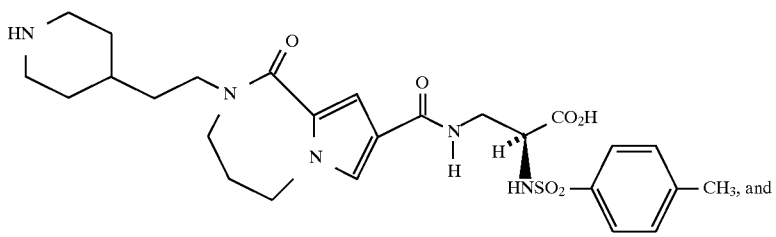

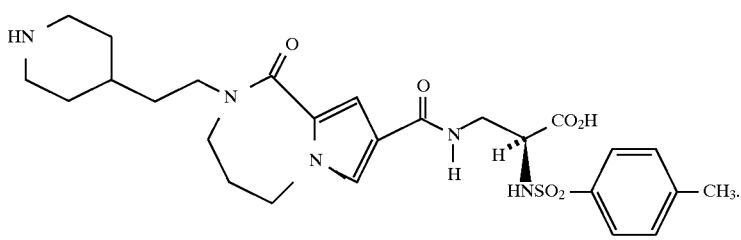

4. A compound having the formula

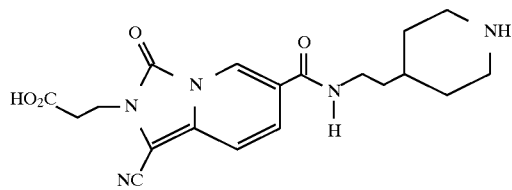

a pharmaceutically acceptable salts.

5. A composition for inhibiting the binding of fibrinogen to blood platelets in a mammal, comprising a compound of claim 1 and a pharmaceutically acceptable carrier.

6. A composition for inhibiting the aggregation of blood platelets in a mammal, comprising a compound of claim 1 and a pharmaceutically acceptable carrier.

7. A composition for preventing thrombus or embolus formation in a mammal, comprising a compound of claim 1 and a pharmaceutically acceptable carrier.

8. A composition for treating thrombus or embolus formation in a mammal, comprising a compound of claim 1 and a pharmaceutically acceptable carrier.

9. A method for inhibiting the binding of fibrinogen to blood platelets in a mammal, comprising administering to the mammal a pharmacologically effective amount of a composition of claim 5.

10. A method for inhibiting the aggregation of blood platelets in a mammal, comprising administering to the mammal a pharmacologically effective amount of a composition of claim 6.

11. A method for preventing thrombus or embolus formation in a mammal, comprising administering to the mammal a pharmacologically effective amount of a composition of claim 7.

12. A method for treating thrombus or embolus formation in a mammal, comprising administering to the mammal the composition of claim 8.

13. A method for inhibiting the aggregation of blood platelets in a mammal, comprising administering to the mammal pharmacologically effective amounts of a thrombolytic agent, a compound of claim 1, and an anticoagulant.

14. A method of claim 13 wherein the thrombolytic agent is tissue plasminogen activator or streptokinase and the anticoagulant is heparin.

15. A method for preventing or treating thrombus or embolus formation in a mammal, comprising administering to the mammal pharmacologically effective amounts of a thrombolytic agent, a compound of claim 1, and an anticoagulant.

16. A method of claim 15 wherein the thrombolytic agent is tissue plasminogen activator or streptokinase and the anticoagulant is heparin.

* * * * *